US005643563A

United States Patent [19]

Ladner et al.

[11] Patent Number: 5,643,563
[45] Date of Patent: Jul. 1, 1997

[54] N-∇3 DELETION MUTANTS OF THE SHORT FORM OF CSF-1

[75] Inventors: Martha B. Ladner, Oakland; Janelle A. Noble; George A. Martin, both of Berkeley, all of Calif.; Ernest S. Kawasaki, Waltham, Mass.; Mazie Y. Coyne, Danville, Calif.; Robert F. Halenbeck, San Rafael, Calif.; Kirston E. Koths, El Cerrito, Calif.

[73] Assignee: Chiron Corporation, Emeryville, Calif.

[21] Appl. No.: 426,036

[22] Filed: Apr. 21, 1995

Related U.S. Application Data

[60] Division of Ser. No. 999,280, Dec. 28, 1992, which is a continuation-in-part of Ser. No. 799,039, Nov. 27, 1991, abandoned, and Ser. No. 799,411, Nov. 27, 1991, abandoned, which is a continuation of Ser. No. 39,657, Apr. 16, 1987, abandoned, and Ser. No. 105,261, Oct. 13, 1987, abandoned, which is a continuation-in-part of Ser. No. 39,654, Apr. 16, 1987, which is a continuation-in-part of Ser. No. 39,657, which is a continuation-in-part of Ser. No. 923,067, Oct. 24, 1986, abandoned, which is a continuation-in-part of Ser. No. 876,819, Jun. 20, 1986, abandoned, which is a continuation-in-part of Ser. No. 821,068, Jan. 21, 1986, abandoned, which is a continuation-in-part of Ser. No. 756,814, Jul. 18, 1985, abandoned, which is a continuation-in-part of Ser. No. 744,924, Jun. 14, 1985, abandoned, which is a continuation-in-part of Ser. No. 728,834, Apr. 30, 1985, abandoned, which is a continuation-in-part of Ser. No. 698,359, Feb. 5, 1985, abandoned, said Ser. No. 799,039, is a continuation-in-part of Ser. No. 39,657, and Ser. No. 105,261.

[51] Int. Cl.[6] .................. A61K 38/19; C07K 14/53; C12N 15/27
[52] U.S. Cl. .................. 424/85.1; 530/351; 435/69.5
[58] Field of Search .................. 435/69.5, 172.3, 435/320, 320.1, 254, 252.33; 536/235; 930/140, 145; 530/351; 514/2, 12; 424/85.1

[56] References Cited

U.S. PATENT DOCUMENTS

| | | | |
|---|---|---|---|
| 4,230,697 | 10/1980 | Nishida et al. | 424/177 |
| 4,275,056 | 6/1981 | Takaku et al. | 424/99 |
| 4,342,828 | 8/1982 | Takaku et al. | 435/41 |
| 4,432,895 | 2/1984 | Tarnowski | 260/112 R |
| 4,438,032 | 3/1984 | Golde et al. | 260/112 R |
| 4,482,485 | 11/1984 | Funakoshi et al. | 260/112 R |
| 4,485,017 | 11/1984 | Tan et al. | 210/635 |
| 4,504,586 | 3/1985 | Nicolson | 436/518 |
| 4,601,978 | 7/1986 | Karen | 435/69.1 |
| 4,658,018 | 4/1987 | Urdal et al. | 530/351 |
| 4,847,201 | 7/1989 | Kawasaki et al. | 435/70 |
| 4,847,325 | 7/1989 | Shadle et al. | 525/54.1 |
| 4,868,119 | 9/1989 | Clark et al. | 435/240 |
| 4,879,227 | 11/1989 | Clark et al. | 435/70 |
| 4,929,700 | 5/1990 | Halenbeck et al. | 530/351 |
| 5,093,242 | 3/1992 | Bachmair et al. | 435/697 |
| 5,104,650 | 4/1992 | Ralph et al. | 424/85.1 |
| 5,171,675 | 12/1992 | Cerutte et al. | 435/695 |

FOREIGN PATENT DOCUMENTS

| | | | |
|---|---|---|---|
| 0169566 | 1/1986 | European Pat. Off. | C07K 15/00 |
| 0249477 | 12/1987 | European Pat. Off. | C12P 21/02 |
| 0261592 | 3/1988 | European Pat. Off. | C12N 15/00 |
| 0272779 | 6/1988 | European Pat. Off. | |
| 0315450 | 5/1989 | European Pat. Off. | |
| 058629 | 4/1982 | Japan | |
| 041615 | 3/1985 | Japan | |
| 09323 | 4/1987 | Japan | |
| 2092159 | 8/1982 | United Kingdom | C07G 7/00 |
| 2134528 | 8/1984 | United Kingdom | C07G 5/00 |
| 8604587 | 8/1986 | WIPO | C07K 3/12 |
| 8604607 | 8/1986 | WIPO | C12N 15/00 |
| 8703204 | 6/1987 | WIPO | A61K 37/02 |
| 8706954 | 11/1987 | WIPO | C12P 21/00 |
| 8803173 | 5/1988 | WIPO | |

OTHER PUBLICATIONS

Takahashi et al. Biochem. Biophys. Res. Comm. 161(2):892–901, 1989.
Ben–Bassat et al. J. Bacteriol. 169(2):751–757, 1987.
Sherman et al. BioEssays. 3(1):27–31, 1985.
Dalboge et al. FEBS. 266 (1,2): 1–3, 1990.
Dalboge, et al., "Cloning And Expression of an Interleukin–1β Precursor and Its Conversion to Interleukin–1β", FEB 246 (1):89–93 (1989).
Dalboge, et al., "A Novel Enzymatic Method For Production of Authentic hGH From An Escherichia coli Produced hGH–Precursor", Biotechnology, 5:161–164 (1987).
Kunitani, et al., "Reversed–Phase Chromatography of Interleukin–2 Muteins", Journal of Chromatography, 359:391–402 (1986).
Lahm, et al., "Characterization of Recombinant Human Interleukin–2 With Micromethods", Journal of Chromatography, 326:357–361 (1985).
Yamagishi, et al., "Determination of the Minimum Polypeptide Molecule With the Biological Activity of Human Tumor Necrosis Factor", Int'l J. of Immunopathology and Pharm., 2 (3):191–202 (1985).
Tsunasawa et al., J. of Biol. Chem. (1985) 260:5382–91.
Dalboge et al., FEBS Letters (1990) 266:1–3.
Dorland's Illustrated Medical Dictionary, 24th Edition, W.B. Saunders Co., Philadelphia (1965) at p. 1485.
Yamanishi et al, J. Biochem, v109, 1991, pp. 404–409.
Metcalf et al. Blood, (1986) 67(2):257–267.
Clark et al. Science (1987) 236:1229–1237.
DeLamarter et al. Nucleic Acids Res. (1987) 15(5):2389–2390.
Rajavashisth et al. PNAS(USA) (1987) 84:1157–1161.

(List continued on next page.)

Primary Examiner—V. Jaganathan
Assistant Examiner—Christine Saoud
Attorney, Agent, or Firm—Donald J. Pochopien; Philip L. McGarrigle, Jr.; Robert P. Blackburn

[57] ABSTRACT

New forms of CSF-1 are provided which relate to N-terminal truncations. Specifically, N-∇3 terminal truncations of the short form of CSF-1 have been found to be particularly advantageous. These forms may have a C-terminal truncation at a variety of different amino acids beyond position 150.

14 Claims, 3 Drawing Sheets

OTHER PUBLICATIONS

Csejtey et al. Biochem. Biophys. Res. Comm. (1986) 138:238–245.
Strickler et al. Biosis (1984) No. 28054134.
Kriegler et al. Exp. Hematol. (1984) 12:844–849.
Biological Abstract No. 29103717 (1985) Biological Abstracts/RRM vol. 5 No. 9 Genet. Technol. News (US) —Hester.
Biological Abstract No. 29077739 (1985) Biological Abstracts/RRM Vil. 5 No. 15 Genet. Eng. Lett. —Fishbein.
Ishizaka et al. Exp. Hematol. (1986) 14:1–8.
Motoyoshi et al. Blood (1978) 52:1012–1020.
Motoyoshi et al. Blood (1983) 62(3):685–688.
Warren et al. J. Immunol. (1985) 134(2):982–989.
Warren et al. J. Immunol. (1986) 137(7):2281–2285.
Ralph et al. Immunobiol. (1986) 172:194–204.
Nagata et al. Nature (1986) 319:415–418.
Nagata et al. J. Embo (1986) 5(3):575–581.
Souza et al. Science (1986) 232:61–65.
Cantrell et al. PNAS(USA) (1985) 82:6250–6256.
Dexter, Nature (1984) 309:746.
Vadas et al., J. Immunol. (1983) 130:793.
Metcalf, Science (1985) 229:16–22.
Das et al., Blood (1981) 58:630.
Stanley et al., J. Biol. Chem. (1977) 252:4305.
Waheed et al., Blood (1982) 60:238.
Ben-Avram et al. PNAS (USA) (1985) 82:7801.
Das et al., J. Biol. Chem. (1982) 257:13679.
Wang et al., J. Cell Biochem. (1983) 21:263.
Waheed et al., Exp. Hemat. (1984) 12:434.
Wu et al., J. Biol. Chem. (1979) 254:6226.
Fojo et al., Biochemistry (1978) 17:3109.
Burgess et al., J. Biol. Chem. (1977) 252:1998.
Lusis et al., Blood (1981) 57:13.
Wu et al., Biochemistry (1980) 19:3846.
Gough et al., Nature (1984) 309:763–767.
Fung et al., Nature (1984) 307:233.
Yang et al., Cell (1986) 47:3–10.
Dorssers et al., Gene (1987).
Yokota et al., PNAS (USA) (1984) 81:1070–1074.
Wong et al. Science (1985) 228:810–815.
Lee et al., PNAS (USA) (1985) 82:4360–4363.
Kawasaki et al., Science (1985) 230:292–296.
Wong et al., Science (1987) 235:1504–1509.
Ladner et al., J. of Embo (1987) 6:2693–2698.
Metcalf, D., J. Cell Physiol. (1970) 76:89.
Moore et al., Science (1984) 223:178.
Stanley, E.R., The Lymphokines (1981), Stewart W.E. et al., (eds) Humana Press, Clifton, N.J., pp. 102–132.
Byrne et al., Cell Biol. (1981) 91:848.
Fleit et al., J. Cell Physiol. (1981) 108:347.
Wing et al., J. Clin. Invest. (1982)69:270.
Ralph et al., Cell. Immunol. (1983) 76:10.
Nogawa et al., Cell Immunol. (1980) 53:116.
Bolivar et al., Gene (1977) 2:95.
Chang et al., Nature (1977) 198:1056.
Goeddel et al., Nucleic Acids Res. (1980) 8:4057.
Shimataka et al., Nature (1981) 292:128.
Broach J.R., Meth. Enz. (1983) 101:307.
Stinchcomb et al., Nature (1979) 282:39.
Tschempe et al., Gene (1980) 10:157.
Clarke et al., Meth. Enz. (1983) 101:300.
Hess et al., J. Adv. Enzyme Reg. (1968) 7:149.
Holland et al., Biochemistry (1978) 17:4900.

Hitzeman et al., J. Biol. Chem. (1980) 255:2073.
Holland et al. J. Biol. Chem. (1981) 256:1385.
Broach et al., Gene (1978) 8:121.
Tissue Culture, Academic Press, Cruz and Patterson (eds.) (1973).
Fiers et al., Nature (1978) 273:113.
Depicker et al., J. Mol. Appl. Gen. (1982) 1:561.
Miller et al., Genetic Engineering (1986) Setlow et al. (ed), Plenum Publishing, vol. 8 pp. 277–297.
Cohen S.N., PNAS (USA) (1972) 69:2110.
Shaw et al., Gene (1983) 23:315.
Graham et al., Virology (1978) 52:546.
Van Solingen et al., J. Bact. (1977) 130:946.
Hsiao et al., PNAS (USA) (1979) 76:3829.
Maniatis et al., Molecular Cloning (1982) Cold Spring Harbor Press, pp. 202–203.
Bailey et al., Anal. Biochem. (1976) 70:75–85.
Sehgal et al., Nature (1980) 288:95–97.
Methods in Enzymology (1980) 65:499–560.
Matteucci et al., J. Am. Chem. Sos. (1981) 103:3185–3191.
Clewell et al., PNAS (USA) (1969) 62:1159.
Clewell D.B., J. Bacteriol (1972) 110:667.
Sanger et al., PNAS (USA) (1977) 74:5463.
Messing et al., Nucleic Acids Res. (1981) 9:309.
Maxam et al., Methods in Enzymology (1980) 65:499.
Fleit et al., J. Cell. Physiol. (1981) 108:347.
Ralph et al., Cell Immunol. (1987)105:270–279.
Wing et al., J. Clin. Invest. (1982) 69:270.
Ralph et al., Cell Immunol. (1983) 76:10.
Stanley E.R., Methods Enzymol. (1985) 116:564.
Gluzman Y., Cell (1981) 23:175.
Ringold G., J. Mol. App. Genet. (1982) 1:165.
Berger et al., Biochemistry (1979) 18:5143.
Aviv et al., PNAS (USA) (1972) 69:1408–1412.
Moore et al., J. Immunol. (1983) 131:2374.
Prystowsky et al., DNA Cloning Techniques: A Practical Apprach (IRL Press, Oxford 1984) Glover, D. (ed.).
Okayama et al., Mol. Cell Biol. (1983) 3:280–289.
Wang A.M. et al., Science (1985) 228:149.
Stanley et al., J. Lab. Clin. Med. (1972) 79:657.
Gorman et al., Science (1983) 221:551–553.
Maxam et al., Methods in Enzymology (1980) 68:521, Academic Press.
Sherman et al., Bio. Essays (1985) 3(1):27–31.
Gonda et al. J. of Biological Chem. (1989) 264:16700–16712.
Cerretti et al., Mol. Immunol. (1988) 25:761–770.
Leatherbarrow et al., Protein Engineering (1986) 1:7–16.

HUMAN CSF-1 GENOMIC STRUCTURE

RP-HPLC ANALYSIS OF $ASP_{59}-SCSF/N^{\nabla}3C^{\nabla}150$ CSF-1

RP-HPLC ANALYSIS OF $ASP_{59}-SCSF/N^{\nabla}2C^{\nabla}150$ CSF-1

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 2302 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 3..1610

( i x ) FEATURE:
        ( A ) NAME/KEY: mat_peptide
        ( B ) LOCATION: 45..1610

( x i ) SEQUENCE DESCRIPTION: SEQ ID NO:1:

```
CC CTG CTG TTG TTG GTC TGT CTC CTG GCG AGC AGG AGT ATC ACC GAG        47
   Leu Leu Leu Leu Val Cys Leu Leu Ala Ser Arg Ser Ile Thr Glu
   -14          -10              -5                        1

GAG GTG TCG GAG TAC TGT AGC CAC ATG ATT GGG AGT GGA CAC CTG CAG       95
Glu Val Ser Glu Tyr Cys Ser His Met Ile Gly Ser Gly His Leu Gln
            5               10                  15

TCT CTG CAG CGG CTG ATT GAC AGT CAG ATG GAG ACC TCG TGC CAA ATT      143
Ser Leu Gln Arg Leu Ile Asp Ser Gln Met Glu Thr Ser Cys Gln Ile
        20              25                  30

ACA TTT GAG TTT GTA GAC CAG GAA CAG TTG AAA GAT CCA GTG TGC TAC      191
Thr Phe Glu Phe Val Asp Gln Glu Gln Leu Lys Asp Pro Val Cys Tyr
    35                  40                  45

CTT AAG AAG GCA TTT CTC CTG GTA CAA GAC ATA ATG GAG GAC ACC ATG      239
Leu Lys Lys Ala Phe Leu Leu Val Gln Asp Ile Met Glu Asp Thr Met
50              55                  60                  65

CGC TTC AGA GAT AAC ACC CCC AAT GCC ATC GCC ATT GTG CAG CTG CAG      287
Arg Phe Arg Asp Asn Thr Pro Asn Ala Ile Ala Ile Val Gln Leu Gln
                70                  75                  80

GAA CTC TCT TTG AGG CTG AAG AGC TGC TTC ACC AAG GAT TAT GAA GAG      335
Glu Leu Ser Leu Arg Leu Lys Ser Cys Phe Thr Lys Asp Tyr Glu Glu
            85                  90                  95

CAT GAC AAG GCC TGC GTC CGA ACT TTC TAT GAG ACA CCT CTC CAG TTG      383
His Asp Lys Ala Cys Val Arg Thr Phe Tyr Glu Thr Pro Leu Gln Leu
            100             105                 110

CTG GAG AAG GTC AAG AAT GTC TTT AAT GAA ACA AAG AAT CTC CTT GAC      431
Leu Glu Lys Val Lys Asn Val Phe Asn Glu Thr Lys Asn Leu Leu Asp
        115                 120                 125

AAG GAC TGG AAT ATT TTC AGC AAG AAC TGC AAC AAC AGC TTT GCT GAA      479
Lys Asp Trp Asn Ile Phe Ser Lys Asn Cys Asn Asn Ser Phe Ala Glu
130                 135                 140                 145

TGC TCC AGC CAA GAT GTG GTG ACC AAG CCT GAT TGC AAC TGC CTG TAC      527
Cys Ser Ser Gln Asp Val Val Thr Lys Pro Asp Cys Asn Cys Leu Tyr
                150                 155                 160

CCC AAA GCC ATC CCT AGC AGT GAC CCG GCC TCT GTC TCC CCT CAT CAG      575
Pro Lys Ala Ile Pro Ser Ser Asp Pro Ala Ser Val Ser Pro His Gln
```

|     |     |     | 165 |     |     |     |     | 170 |     |     |     |     | 175 |     |     |      |
|-----|-----|-----|-----|-----|-----|-----|-----|-----|-----|-----|-----|-----|-----|-----|-----|------|
| CCC | CTC | GCC | CCC | TCC | ATG | GCC | CCT | GTG | GCT | GGC | TTG | ACC | TGG | GAG | GAC | 623  |
| Pro | Leu | Ala | Pro | Ser | Met | Ala | Pro | Val | Ala | Gly | Leu | Thr | Trp | Glu | Asp |      |
|     |     | 180 |     |     |     |     | 185 |     |     |     |     | 190 |     |     |     |      |

```
TCT GAG GGA ACT GAG GGC AGC TCC CTC TTG CCT GGT GAG CAG CCC CTG    671
Ser Glu Gly Thr Glu Gly Ser Ser Leu Leu Pro Gly Glu Gln Pro Leu
    195             200                 205

CAC ACA GTG GAT CCA GGC AGT GCC AAG CAG CGG CCA CCC AGG AGC ACC    719
His Thr Val Asp Pro Gly Ser Ala Lys Gln Arg Pro Pro Arg Ser Thr
210             215                 220                 225

TGC CAG AGC TTT GAG CCG CCA GAG ACC CCA GTT GTC AAG GAC AGC ACC    767
Cys Gln Ser Phe Glu Pro Pro Glu Thr Pro Val Val Lys Asp Ser Thr
            230                 235                 240

ATC GGT GGC TCA CCA CAG CCT CGC CCC TCT GTC GGG GCC TTC AAC CCC    815
Ile Gly Gly Ser Pro Gln Pro Arg Pro Ser Val Gly Ala Phe Asn Pro
                245                 250                 255

GGG ATG GAG GAT ATT CTT GAC TCT GCA ATG GGC ACT AAT TGG GTC CCA    863
Gly Met Glu Asp Ile Leu Asp Ser Ala Met Gly Thr Asn Trp Val Pro
            260                 265                 270

GAA GAA GCC TCT GGA GAG GCC AGT GAG ATT CCC GTA CCC CAA GGG ACA    911
Glu Glu Ala Ser Gly Glu Ala Ser Glu Ile Pro Val Pro Gln Gly Thr
    275                 280                 285

GAG CTT TCC CCC TCC AGG CCA GGA GGG GGC AGC ATG CAG ACA GAG CCC    959
Glu Leu Ser Pro Ser Arg Pro Gly Gly Gly Ser Met Gln Thr Glu Pro
290                 295                 300                 305

GCC AGA CCC AGC AAC TTC CTC TCA GCA TCT TCT CCA CTC CCT GCA TCA   1007
Ala Arg Pro Ser Asn Phe Leu Ser Ala Ser Ser Pro Leu Pro Ala Ser
                310                 315                 320

GCA AAG GGC CAA CAG CCG GCA GAT GTA ACT GGT ACA GCC TTG CCC AGG   1055
Ala Lys Gly Gln Gln Pro Ala Asp Val Thr Gly Thr Ala Leu Pro Arg
                325                 330                 335

GTG GGC CCC GTG AGG CCC ACT GGC CAG GAC TGG AAT CAC ACC CCC CAG   1103
Val Gly Pro Val Arg Pro Thr Gly Gln Asp Trp Asn His Thr Pro Gln
            340                 345                 350

AAG ACA GAC CAT CCA TCT GCC CTG CTC AGA GAC CCC CCG GAG CCA GGC   1151
Lys Thr Asp His Pro Ser Ala Leu Leu Arg Asp Pro Pro Glu Pro Gly
    355                 360                 365

TCT CCC AGG ATC TCA TCA CTG CGC CCC CAG GGC CTC AGC AAC CCC TCC   1199
Ser Pro Arg Ile Ser Ser Leu Arg Pro Gln Gly Leu Ser Asn Pro Ser
370                 375                 380                 385

ACC CTC TCT GCT CAG CCA CAG CTT TCC AGA AGC CAC TCC TCG GGC AGC   1247
Thr Leu Ser Ala Gln Pro Gln Leu Ser Arg Ser His Ser Ser Gly Ser
                390                 395                 400

GTG CTG CCC CTT GGG GAG CTG GAG GGC AGG AGG AGC ACC AGG GAT CGG   1295
Val Leu Pro Leu Gly Glu Leu Glu Gly Arg Arg Ser Thr Arg Asp Arg
            405                 410                 415

AGG AGC CCC GCA GAG CCA GAA GGA GGA CCA GCA AGT GAA GGG GCA GCC   1343
Arg Ser Pro Ala Glu Pro Glu Gly Gly Pro Ala Ser Glu Gly Ala Ala
        420                 425                 430

AGG CCC CTG CCC CGT TTT AAC TCC GTT CCT TTG ACT GAC ACA GGC CAT   1391
Arg Pro Leu Pro Arg Phe Asn Ser Val Pro Leu Thr Asp Thr Gly His
        435                 440                 445

GAG AGG CAG TCC GAG GGA TCC TCC AGC CCG CAG CTC CAG GAG TCT GTC   1439
Glu Arg Gln Ser Glu Gly Ser Ser Ser Pro Gln Leu Gln Glu Ser Val
450                 455                 460                 465

TTC CAC CTG CTG GTG CCC AGT GTC ATC CTG GTC TTG CTG GCC GTC GGA   1487
Phe His Leu Leu Val Pro Ser Val Ile Leu Val Leu Leu Ala Val Gly
                470                 475                 480

GGC CTC TTG TTC TAC AGG TGG AGG CGG CGG AGC CAT CAA GAG CCT CAG   1535
Gly Leu Leu Phe Tyr Arg Trp Arg Arg Arg Ser His Gln Glu Pro Gln
```

```
                      485                         490                         495
AGA  GCG  GAT  TCT  CCC  TTG  GAG  CAA  CCA  GAG  GGC  AGC  CCC  CTG  ACT  CAG      1583
Arg  Ala  Asp  Ser  Pro  Leu  Glu  Gln  Pro  Glu  Gly  Ser  Pro  Leu  Thr  Gln
          500                      505                      510

GAT  GAC  AGA  CAG  GTG  GAA  CTG  CCA  GTG  TAGAGGGAAT  TCTAAGACCC                 1630
Asp  Asp  Arg  Gln  Val  Glu  Leu  Pro  Val
          515                      520

CTCACCATCC  TGGACACACT  CGTTTGTCAA  TGTCCCTCTG  AAAATGTGAC  GCCCAGCCCC              1690

GGACACAGTA  CTCCAGATGT  TGTCTGACCA  GCTCAGAGAG  AGTACAGTGG  GACTGTTACC              1750

TTCCTTGATA  TGGACAGTAT  TCTTCTATTT  GTGCAGATTA  AGATTGCATT  AGTTTTTTC               1810

TTAACAACTG  CATCATACTG  TTGTCATATG  TTGAGCCTGT  GGTCTATTAA  AACCCCTAGT              1870

TCCATTTCCC  ATAAACTTCT  GTCAAGCCAG  ACCATCTCTA  CCCTGTACTT  GGACAACTTA              1930

ACTTTTTTAA  CCAAAGTGCA  GTTTATGTTC  ACCTTTGTTA  AAGCCACCT̄T  GTGGTTTCTG              1990

CCCATCACCT  GAACCTACTG  AAGTTGTGTG  AAATCCTAAT  TCTGTCATCT  CCGTAGCCCT              2050

CCCAGTTGTG  CCTCCTGCAC  ATTGATGAGT  GCCTGCTGTT  GTCTTTGCCC  ATGTTGTTGA              2110

TGTAGCTGTG  ACCCTATTGT  TCCTCACCCC  TGCCCCCCGC  CAACCCCAGC  TGGCCCACCT              2170

CTTCCCCCTC  CCACCCAAGC  CCACAGCCAG  CCCATCAGGA  AGCCTTCCTG  GCTTCTCCAC              2230

AACCTTCTGA  CTGCTCTTTT  CAGTCATGCC  CCTCCTGCTC  TTTTGTATTT  GGCTAATAGT              2290

ATATCAATTT  GC                                                                     2302
```

( 2 ) INFORMATION FOR SEQ ID NO:2:

( i ) SEQUENCE CHARACTERISTICS:
        ( A ) LENGTH: 536 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Leu  Leu  Leu  Leu  Val  Cys  Leu  Leu  Ala  Ser  Arg  Ser  Ile  Thr  Glu  Glu
-14                 -10                      -5                            1

Val  Ser  Glu  Tyr  Cys  Ser  His  Met  Ile  Gly  Ser  Gly  His  Leu  Gln  Ser
               5                    10                      15

Leu  Gln  Arg  Leu  Ile  Asp  Ser  Gln  Met  Glu  Thr  Ser  Cys  Gln  Ile  Thr
          20                   25                      30

Phe  Glu  Phe  Val  Asp  Gln  Glu  Gln  Leu  Lys  Asp  Pro  Val  Cys  Tyr  Leu
35                       40                      45                         50

Lys  Lys  Ala  Phe  Leu  Leu  Val  Gln  Asp  Ile  Met  Glu  Asp  Thr  Met  Arg
                    55                        60                       65

Phe  Arg  Asp  Asn  Thr  Pro  Asn  Ala  Ile  Ala  Ile  Val  Gln  Leu  Gln  Glu
               70                        75                       80

Leu  Ser  Leu  Arg  Leu  Lys  Ser  Cys  Phe  Thr  Lys  Asp  Tyr  Glu  Glu  His
          85                        90                       95

Asp  Lys  Ala  Cys  Val  Arg  Thr  Phe  Tyr  Glu  Thr  Pro  Leu  Gln  Leu  Leu
     100                      105                      110

Glu  Lys  Val  Lys  Asn  Val  Phe  Asn  Glu  Thr  Lys  Asn  Leu  Leu  Asp  Lys
115                      120                      125                      130

Asp  Trp  Asn  Ile  Phe  Ser  Lys  Asn  Cys  Asn  Asn  Ser  Phe  Ala  Glu  Cys
                    135                      140                      145

Ser  Ser  Gln  Asp  Val  Val  Thr  Lys  Pro  Asp  Cys  Asn  Cys  Leu  Tyr  Pro
               150                      155                      160

Lys  Ala  Ile  Pro  Ser  Ser  Asp  Pro  Ala  Ser  Val  Ser  Pro  His  Gln  Pro
```

|         |         |         |         | 165     |         |         |         | 170     |         |         |         | 175     |         |         |
|---------|---------|---------|---------|---------|---------|---------|---------|---------|---------|---------|---------|---------|---------|---------|
| Leu     | Ala     | Pro     | Ser     | Met     | Ala     | Pro     | Val     | Ala     | Gly     | Leu     | Thr     | Trp     | Glu     | Asp     | Ser     |
|         | 180     |         |         |         |         | 185     |         |         |         | 190     |         |         |         |         |
| Glu     | Gly     | Thr     | Glu     | Gly     | Ser     | Ser     | Leu     | Leu     | Pro     | Gly     | Glu     | Gln     | Pro     | Leu     | His     |
| 195     |         |         |         |         | 200     |         |         |         |         | 205     |         |         |         |         | 210     |
| Thr     | Val     | Asp     | Pro     | Gly     | Ser     | Ala     | Lys     | Gln     | Arg     | Pro     | Pro     | Arg     | Ser     | Thr     | Cys     |
|         |         |         |         | 215     |         |         |         |         | 220     |         |         |         |         | 225     |         |
| Gln     | Ser     | Phe     | Glu     | Pro     | Pro     | Glu     | Thr     | Pro     | Val     | Val     | Lys     | Asp     | Ser     | Thr     | Ile     |
|         |         |         | 230     |         |         |         |         | 235     |         |         |         |         |         | 240     |         |
| Gly     | Gly     | Ser     | Pro     | Gln     | Pro     | Arg     | Pro     | Ser     | Val     | Gly     | Ala     | Phe     | Asn     | Pro     | Gly     |
|         |         | 245     |         |         |         |         | 250     |         |         |         |         | 255     |         |         |         |
| Met     | Glu     | Asp     | Ile     | Leu     | Asp     | Ser     | Ala     | Met     | Gly     | Thr     | Asn     | Trp     | Val     | Pro     | Glu     |
|         | 260     |         |         |         |         | 265     |         |         |         | 270     |         |         |         |         |         |
| Glu     | Ala     | Ser     | Gly     | Glu     | Ala     | Ser     | Glu     | Ile     | Pro     | Val     | Pro     | Gln     | Gly     | Thr     | Glu     |
| 275     |         |         |         | 280     |         |         |         |         |         | 285     |         |         |         |         | 290     |
| Leu     | Ser     | Pro     | Ser     | Arg     | Pro     | Gly     | Gly     | Gly     | Ser     | Met     | Gln     | Thr     | Glu     | Pro     | Ala     |
|         |         |         |         | 295     |         |         |         |         | 300     |         |         |         |         | 305     |         |
| Arg     | Pro     | Ser     | Asn     | Phe     | Leu     | Ser     | Ala     | Ser     | Ser     | Pro     | Leu     | Pro     | Ala     | Ser     | Ala     |
|         |         |         | 310     |         |         |         |         | 315     |         |         |         |         | 320     |         |         |
| Lys     | Gly     | Gln     | Gln     | Pro     | Ala     | Asp     | Val     | Thr     | Gly     | Thr     | Ala     | Leu     | Pro     | Arg     | Val     |
|         |         | 325     |         |         |         |         |         | 330     |         |         |         | 335     |         |         |         |
| Gly     | Pro     | Val     | Arg     | Pro     | Thr     | Gly     | Gln     | Asp     | Trp     | Asn     | His     | Thr     | Pro     | Gln     | Lys     |
|         | 340     |         |         |         |         | 345     |         |         |         |         | 350     |         |         |         |         |
| Thr     | Asp     | His     | Pro     | Ser     | Ala     | Leu     | Leu     | Arg     | Asp     | Pro     | Pro     | Glu     | Pro     | Gly     | Ser     |
| 355     |         |         |         |         | 360     |         |         |         |         | 365     |         |         |         |         | 370     |
| Pro     | Arg     | Ile     | Ser     | Ser     | Leu     | Arg     | Pro     | Gln     | Gly     | Leu     | Ser     | Asn     | Pro     | Ser     | Thr     |
|         |         |         |         | 375     |         |         |         |         | 380     |         |         |         |         | 385     |         |
| Leu     | Ser     | Ala     | Gln     | Pro     | Gln     | Leu     | Ser     | Arg     | Ser     | His     | Ser     | Ser     | Gly     | Ser     | Val     |
|         |         |         | 390     |         |         |         |         | 395     |         |         |         |         | 400     |         |         |
| Leu     | Pro     | Leu     | Gly     | Glu     | Leu     | Glu     | Gly     | Arg     | Arg     | Ser     | Thr     | Arg     | Asp     | Arg     | Arg     |
|         |         | 405     |         |         |         |         | 410     |         |         |         |         | 415     |         |         |         |
| Ser     | Pro     | Ala     | Glu     | Pro     | Glu     | Gly     | Gly     | Pro     | Ala     | Ser     | Glu     | Gly     | Ala     | Ala     | Arg     |
|         | 420     |         |         |         |         | 425     |         |         |         |         | 430     |         |         |         |         |
| Pro     | Leu     | Pro     | Arg     | Phe     | Asn     | Ser     | Val     | Pro     | Leu     | Thr     | Asp     | Thr     | Gly     | His     | Glu     |
| 435     |         |         |         |         | 440     |         |         |         |         | 445     |         |         |         |         | 450     |
| Arg     | Gln     | Ser     | Glu     | Gly     | Ser     | Ser     | Ser     | Pro     | Gln     | Leu     | Gln     | Glu     | Ser     | Val     | Phe     |
|         |         |         |         | 455     |         |         |         |         | 460     |         |         |         |         | 465     |         |
| His     | Leu     | Leu     | Val     | Pro     | Ser     | Val     | Ile     | Leu     | Val     | Leu     | Leu     | Ala     | Val     | Gly     | Gly     |
|         |         |         | 470     |         |         |         |         | 475     |         |         |         |         | 480     |         |         |
| Leu     | Leu     | Phe     | Tyr     | Arg     | Trp     | Arg     | Arg     | Arg     | Ser     | His     | Gln     | Glu     | Pro     | Gln     | Arg     |
|         |         | 485     |         |         |         |         |         | 490     |         |         |         |         | 495     |         |         |
| Ala     | Asp     | Ser     | Pro     | Leu     | Glu     | Gln     | Pro     | Glu     | Gly     | Ser     | Pro     | Leu     | Thr     | Gln     | Asp     |
|         |         |         | 500     |         |         |         |         | 505     |         |         |         | 510     |         |         |         |
| Asp     | Arg     | Gln     | Val     | Glu     | Leu     | Pro     | Val     |         |         |         |         |         |         |         |         |
| 515     |         |         |         |         | 520     |         |         |         |         |         |         |         |         |         |         |

( 2 ) INFORMATION FOR SEQ ID NO:3:

( i ) SEQUENCE CHARACTERISTICS:
        ( A ) LENGTH: 1642 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

( A ) NAME/KEY: CDS
( B ) LOCATION: 179..946

( i x ) FEATURE:
( A ) NAME/KEY: mat_peptide
( B ) LOCATION: 275..946

( i x ) FEATURE:
( A ) NAME/KEY: -
( B ) LOCATION: 340
( D ) OTHER INFORMATION: /note= "Intron Sequence"

( x i ) SEQUENCE DESCRIPTION: SEQ ID NO:3:

```
AGTGAGGCTC GGCCCGGGGA AAGTGAAAGT TTGCCTGGGT CCTCTCGGCG CCAGAGCCGC        60

TCTCCGCATC CCAGGACAGC GGTGCGGCCC TCGGCCGGGG CGCCCACTCC GCAGCAGCCA       120

GCGAGCGAGC GAGCGAGCGA GGGCGGCCGA CGCGCCCGGC CGGGACCCAG CTGCCCGT         178

ATG ACC GCG CCG GGC GCC GCC GGG CGC TGC CCT CCC ACG ACA TGG CTG        226
Met Thr Ala Pro Gly Ala Ala Gly Arg Cys Pro Pro Thr Thr Trp Leu
-32     -30             -25                 -20

GGC TCC CTG CTG TTG TTG GTC TGT CTC CTG GCG AGC AGG AGT ATC ACC        274
Gly Ser Leu Leu Leu Leu Val Cys Leu Leu Ala Ser Arg Ser Ile Thr
        -15                 -10                 -5

GAG GAG GTG TCG GAG TAC TGT AGC CAC ATG ATT GGG AGT GGA CAC CTG        322
Glu Glu Val Ser Glu Tyr Cys Ser His Met Ile Gly Ser Gly His Leu
 1               5                  10                  15

CAG TCT CTG CAG CGG CTG ATT GAC AGT CAG ATG GAG ACC TCG TGC CAA        370
Gln Ser Leu Gln Arg Leu Ile Asp Ser Gln Met Glu Thr Ser Cys Gln
            20                  25                  30

ATT ACA TTT GAG TTT GTA GAC CAG GAA CAG TTG AAA GAT CCA GTG TGC        418
Ile Thr Phe Glu Phe Val Asp Gln Glu Gln Leu Lys Asp Pro Val Cys
        35                  40                  45

TAC CTT AAG AAG GCA TTT CTC CTG GTA CAA TAC ATA ATG GAG GAC ACC        466
Tyr Leu Lys Lys Ala Phe Leu Leu Val Gln Tyr Ile Met Glu Asp Thr
    50                  55                  60

ATG CGC TTC AGA GAT AAC ACC CCC AAT GCC ATC GCC ATT GTG CAG CTG        514
Met Arg Phe Arg Asp Asn Thr Pro Asn Ala Ile Ala Ile Val Gln Leu
 65                  70                  75                  80

CAG GAA CTC TCT TTG AGG CTG AAG AGC TGC TTC ACC AAG GAT TAT GAA        562
Gln Glu Leu Ser Leu Arg Leu Lys Ser Cys Phe Thr Lys Asp Tyr Glu
                85                  90                  95

GAG CAT GAC AAG GCC TGC GTC CGA ACT TTC TAT GAG ACA CCT CTC CAG        610
Glu His Asp Lys Ala Cys Val Arg Thr Phe Tyr Glu Thr Pro Leu Gln
            100                 105                 110

TTG CTG GAG AAG GTC AAG AAT GTC TTT AAT GAA ACA AAG AAT CTC CTT        658
Leu Leu Glu Lys Val Lys Asn Val Phe Asn Glu Thr Lys Asn Leu Leu
        115                 120                 125

GAC AAG GAC TGG AAT ATT TTC AGC AAG AAC TGC AAC AAC AGC TTT GCT        706
Asp Lys Asp Trp Asn Ile Phe Ser Lys Asn Cys Asn Asn Ser Phe Ala
130                 135                 140

GAA TGC TCC AGC CAA GGC CAT GAG AGG CAG TCC GAG GGA TCC TCC AGC        754
Glu Cys Ser Ser Gln Gly His Glu Arg Gln Ser Glu Gly Ser Ser Ser
145                 150                 155                 160

CCG CAG CTC CAG GAG TCT GTC TTC CAC CTG CTG GTG CCC AGT GTC ATC        802
Pro Gln Leu Gln Glu Ser Val Phe His Leu Leu Val Pro Ser Val Ile
                165                 170                 175

CTG GTC TTG CTG GCC GTC GGA GGC CTC TTG TTC TAC AGG TGG AGG CGG        850
Leu Val Leu Leu Ala Val Gly Gly Leu Leu Phe Tyr Arg Trp Arg Arg
                180                 185                 190

CGG AGC CAT CAA GAG CCT CAG AGA GCG GAT TCT CCC TTG GAG CAA CCA        898
Arg Ser His Gln Glu Pro Gln Arg Ala Asp Ser Pro Leu Glu Gln Pro
        195                 200                 205
```

| | | | | | | | | | | | | | | |
|---|---|---|---|---|---|---|---|---|---|---|---|---|---|---|
| GAG | GGC | AGC | CCC | CTG | ACT | CAG | GAT | GAC | AGA | CAG | GTG | GAA | CTG | CCA | GTG | 946 |
| Glu | Gly | Ser | Pro | Leu | Thr | Gln | Asp | Asp | Arg | Gln | Val | Glu | Leu | Pro | Val |
| | 210 | | | | | 215 | | | | | 220 | | | | |

| | | | | |
|---|---|---|---|---|
| TAGAGGGAAT | TCTAAGACCC | CTCACCATCC | TGGACACACT | CGTTTGTCAA | TGTCCCTCTG | 1006 |
| AAAATGTGAC | GCCCAGCCCC | GGACACAGTA | CTCCAGATGT | TGTCTGACCA | GCTCAGAGAG | 1066 |
| AGTACAGTGG | GACTGTTACC | TTCCTTGATA | TGGACAGTAT | TCTTCTATTT | GTGCAGATTA | 1126 |
| AGATTGCATT | AGTTTTTTTC | TTAACAACTG | CATCATACTG | TTGTCATATG | TTGAGCCTGT | 1186 |
| GGTCTATTAA | AACCCCTAGT | TCCATTTCCC | ATAAACTTCT | GTCAAGCCAG | ACCATCTCTA | 1246 |
| CCCTGTACTT | GGACAACTTA | ACTTTTTTAA | CCAAAGTGCA | GTTTATGTTC | ACCTTTGTTA | 1306 |
| AAGCCACCTT | GTGGTTTCTG | CCCATCACCT | GAACCTACTG | AAGTTGTGTG | AAATCCTAAT | 1366 |
| TCTGTCATCT | CCGTAGCCCT | CCCAGTTGTG | CCTCCTGCAC | ATTGATGAGT | GCCTGCTGTT | 1426 |
| GTCTTTGCCC | ATGTTGTTGA | TGTAGCTGTG | ACCCTATTGT | TCCTCACCCC | TGCCCCCCGC | 1486 |
| CAACCCCAGC | TGGCCCACCT | CTTCCCCCTC | CCACCCAAGC | CCACAGCCAG | CCCATCAGGA | 1546 |
| AGCCTTCCTG | GCTTCTCCAC | AACCTTCTGA | CTGCTCTTTT | CAGTCATGCC | CCTCCTGCTC | 1606 |
| TTTTGTATTT | GGCTAATAGT | ATATCAATTT | GCACTT | | | 1642 |

( 2 ) INFORMATION FOR SEQ ID NO:4:

( i ) SEQUENCE CHARACTERISTICS:
        ( A ) LENGTH: 256 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Thr | Ala | Pro | Gly | Ala | Ala | Gly | Arg | Cys | Pro | Pro | Thr | Thr | Trp | Leu |
| -32 | | -30 | | | | -25 | | | | | -20 | | | | |
| Gly | Ser | Leu | Leu | Leu | Leu | Val | Cys | Leu | Leu | Ala | Ser | Arg | Ser | Ile | Thr |
| | -15 | | | | | -10 | | | | | -5 | | | | |
| Glu | Glu | Val | Ser | Glu | Tyr | Cys | Ser | His | Met | Ile | Gly | Ser | Gly | His | Leu |
| 1 | | | | 5 | | | | | 10 | | | | | 15 | |
| Gln | Ser | Leu | Gln | Arg | Leu | Ile | Asp | Ser | Gln | Met | Glu | Thr | Ser | Cys | Gln |
| | | | 20 | | | | | 25 | | | | | 30 | | |
| Ile | Thr | Phe | Glu | Phe | Val | Asp | Gln | Glu | Gln | Leu | Lys | Asp | Pro | Val | Cys |
| | | 35 | | | | | 40 | | | | | 45 | | | |
| Tyr | Leu | Lys | Lys | Ala | Phe | Leu | Leu | Val | Gln | Tyr | Ile | Met | Glu | Asp | Thr |
| | 50 | | | | | 55 | | | | | 60 | | | | |
| Met | Arg | Phe | Arg | Asp | Asn | Thr | Pro | Asn | Ala | Ile | Ala | Ile | Val | Gln | Leu |
| 65 | | | | | 70 | | | | | 75 | | | | | 80 |
| Gln | Glu | Leu | Ser | Leu | Arg | Leu | Lys | Ser | Cys | Phe | Thr | Lys | Asp | Tyr | Glu |
| | | | | 85 | | | | | 90 | | | | | 95 | |
| Glu | His | Asp | Lys | Ala | Cys | Val | Arg | Thr | Phe | Tyr | Glu | Thr | Pro | Leu | Gln |
| | | | 100 | | | | | 105 | | | | | 110 | | |
| Leu | Leu | Glu | Lys | Val | Lys | Asn | Val | Phe | Asn | Glu | Thr | Lys | Asn | Leu | Leu |
| | | 115 | | | | | 120 | | | | | 125 | | | |
| Asp | Lys | Asp | Trp | Asn | Ile | Phe | Ser | Lys | Asn | Cys | Asn | Asn | Ser | Phe | Ala |
| | 130 | | | | | 135 | | | | | 140 | | | | |
| Glu | Cys | Ser | Ser | Gln | Gly | His | Glu | Arg | Gln | Ser | Glu | Gly | Ser | Ser | Ser |
| 145 | | | | | 150 | | | | | 155 | | | | | 160 |
| Pro | Gln | Leu | Gln | Glu | Ser | Val | Phe | His | Leu | Leu | Val | Pro | Ser | Val | Ile |
| | | | | 165 | | | | | 170 | | | | | 175 | |
| Leu | Val | Leu | Leu | Ala | Val | Gly | Gly | Leu | Leu | Phe | Tyr | Arg | Trp | Arg | Arg |

```
                    180                     185                       190
Arg  Ser  His  Gln  Glu  Pro  Gln  Arg  Ala  Asp  Ser  Pro  Leu  Glu  Gln  Pro
              195                      200                     205

Glu  Gly  Ser  Pro  Leu  Thr  Gln  Asp  Asp  Arg  Gln  Val  Glu  Leu  Pro  Val
     210                     215                    220
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Val  Ser  Glu  Tyr  Cys  Ser
1                   5
```

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Ser  Glu  Tyr  Cys  Ser
1               5
```

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GAAGAAGTGT CGGAGTAC                                        18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GAGGAGGTGT CGGAGTAC                                        18

( 2 ) INFORMATION FOR SEQ ID NO:9:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GGTACAAGAT ATCATGGAAG ATACAATGCG CTTC   34

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CCGATCATGT GSKAGCASTA CTCGGACACC TCCTC   35

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GARTA Y TG YW SC- CA Y ATG   18

( 2 ) INFORMATION FOR SEQ ID NO:12:

( i ) SEQUENCE CHARACTERISTICS:
        ( A ) LENGTH: 106 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CTGCAGGAGC TCAGATCTTC TAGAGAATTC CGAGCGGCCG CATCGATGGT ACCGACGTCC   60

TCGAGTCTAG AAGATCTCTT AAGGCTCGCC GGCGTAGCTA CCATGG   106

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TACCTTAAAC CGGCATTTCT C   21

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TACCTTAAAC AGGCCTTTCT C    21

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GGTACAAGAT ATCATGGAG    19

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

Arg His Asp Lys Ile His
1               5

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GAGGGATCCT GATCACCGCA GCTCC    25

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AGCCAAGGCT GATCAAGGCA GTCC    24

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GAAGAAGTTT CTGAATAT    18

( 2 ) INFORMATION FOR SEQ ID NO:20:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

```
GGCTTGACCT GATCAGACTC TGAGG                                               25
```

( 2 ) INFORMATION FOR SEQ ID NO:21:

( i ) SEQUENCE CHARACTERISTICS:
    ( A ) LENGTH: 3931 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 160..1816

( i x ) FEATURE:
    ( A ) NAME/KEY: mat_peptide
    ( B ) LOCATION: 256..1816

( x i ) SEQUENCE DESCRIPTION: SEQ ID NO:21:

```
TGAAAGTTTG CCTCGGTGCT CTCGGTGTCG CTGCGGCTCT CTGCATCCCA GGACAGCGGC         60

GTGGCCCTCG ACCGGGCGC  GGGCTCTTCA GCCACTAGCG AGCAAGGGAG CGAGCGAACC        120

AGGGCGGCCA ACACGCCGTG CCGGGACCCA GCTGCCCGT ATG ACC GCG CGG GGC          174
                                           Met Thr Ala Arg Gly
                                           -32         -30

GCC GCG GGG CGC TGC CCT TCT TCG ACA TGG CTG GGC TCC CGG CTG CTG         222
Ala Ala Gly Arg Cys Pro Ser Ser Thr Trp Leu Gly Ser Arg Leu Leu
        -25             -20                     -15

CTG GTC TGT CTC CTC ATG AGC AGG AGT ATT GCC AAG GAG GTG TCA GAA         270
Leu Val Cys Leu Leu Met Ser Arg Ser Ile Ala Lys Glu Val Ser Glu
    -10             -5                   1                       5

CAC TGT AGC CAC ATG ATT GGG AAT GGA CAC CTG AAG GTC CTG CAG CAG         318
His Cys Ser His Met Ile Gly Asn Gly His Leu Lys Val Leu Gln Gln
                10                  15                  20

TTG ATC GAC AGT CAA ATG GAG ACT TCA TGC CAG ATT GCC TTT GAA TTT         366
Leu Ile Asp Ser Gln Met Glu Thr Ser Cys Gln Ile Ala Phe Glu Phe
            25                  30                  35

GTA GAC CAG GAA CAG CTG GAT GAT CCT GTT TGC TAC CTA AAG AAG GCC         414
Val Asp Gln Glu Gln Leu Asp Asp Pro Val Cys Tyr Leu Lys Lys Ala
        40                  45                  50

TTT TTT CTG GTA CAA GAC ATA ATA GAT GAG ACC ATG CGC TTT AAA GAC         462
Phe Phe Leu Val Gln Asp Ile Ile Asp Glu Thr Met Arg Phe Lys Asp
    55                  60                  65

AAC ACC CCC AAT GCT AAC GCC ACC GAG AGG CTC CAG GAA CTC TCC AAT         510
Asn Thr Pro Asn Ala Asn Ala Thr Glu Arg Leu Gln Glu Leu Ser Asn
70                  75                  80                  85

AAC CTG AAC AGC TGC TTC ACC AAG GAC TAT GAG GAG CAG AAC AAG GCC         558
Asn Leu Asn Ser Cys Phe Thr Lys Asp Tyr Glu Glu Gln Asn Lys Ala
                90                  95                  100

TGT GTC CGA ACT TTC CAT GAG ACT CCT CTC CAG CTG CTG GAG AAG ATC         606
Cys Val Arg Thr Phe His Glu Thr Pro Leu Gln Leu Leu Glu Lys Ile
            105                 110                 115

AAG AAC TTC TTT AAT GAA ACA AAG AAT CTC CTT GAA AAG GAC TGG AAC         654
```

| | | | | | | | | | | | | | | | |
|---|---|---|---|---|---|---|---|---|---|---|---|---|---|---|---|
| Lys | Asn | Phe 120 | Phe | Asn | Glu | Thr | Lys 125 | Asn | Leu | Leu | Glu | Lys 130 | Asp | Trp | Asn |

```
ATT  TTT  ACC  AAG  AAC  TGC  AAC  AAC  AGC  TTT  GCT  AAG  TGC  TCT  AGC  CGA     702
Ile  Phe  Thr  Lys  Asn  Cys  Asn  Asn  Ser  Phe  Ala  Lys  Cys  Ser  Ser  Arg
     135                      140                      145

GAT  GTG  GTG  ACC  AAG  CCT  GAT  TGC  AAC  TGC  CTG  TAC  CCT  AAA  GCC  ACC     750
Asp  Val  Val  Thr  Lys  Pro  Asp  Cys  Asn  Cys  Leu  Tyr  Pro  Lys  Ala  Thr
150                           155                      160                      165

CCT  AGC  AGT  GAC  CCG  GCC  TCT  GCC  TCC  CCT  CAC  CAG  CCC  CCC  GCC  CCC     798
Pro  Ser  Ser  Asp  Pro  Ala  Ser  Ala  Ser  Pro  His  Gln  Pro  Pro  Ala  Pro
               170                           175                           180

TCC  ATG  GCC  CCT  CTG  GCT  GGC  TTG  GCT  TGG  GAT  GAT  TCT  CAG  AGG  ACA     846
Ser  Met  Ala  Pro  Leu  Ala  Gly  Leu  Ala  Trp  Asp  Asp  Ser  Gln  Arg  Thr
               185                           190                           195

GAG  GGC  AGC  TCC  CTC  TTG  CCC  AGT  GAG  CTT  CCC  CTT  CGC  ATA  GAG  GAC     894
Glu  Gly  Ser  Ser  Leu  Leu  Pro  Ser  Glu  Leu  Pro  Leu  Arg  Ile  Glu  Asp
               200                           205                           210

CCA  GGC  AGT  GCC  AAG  CAG  CGA  CCA  CCC  AGG  AGT  ACC  TGC  CAG  ACC  CTC     942
Pro  Gly  Ser  Ala  Lys  Gln  Arg  Pro  Pro  Arg  Ser  Thr  Cys  Gln  Thr  Leu
     215                      220                      225

GAG  TCA  ACA  GAG  CAA  CCA  AAC  CAT  GGG  GAC  AGA  CTC  ACT  GAG  GAC  TCA     990
Glu  Ser  Thr  Glu  Gln  Pro  Asn  His  Gly  Asp  Arg  Leu  Thr  Glu  Asp  Ser
230                           235                      240                      245

CAA  CCT  CAT  CCT  TCT  GCG  GGG  GGG  CCC  GTC  CCT  GGG  GTG  GAA  GAC  ATT    1038
Gln  Pro  His  Pro  Ser  Ala  Gly  Gly  Pro  Val  Pro  Gly  Val  Glu  Asp  Ile
               250                           255                           260

CTT  GAA  TCT  TCA  CTG  GGC  ACT  AAC  TGG  GTC  CTA  GAA  GAA  GCT  TCT  GGA    1086
Leu  Glu  Ser  Ser  Leu  Gly  Thr  Asn  Trp  Val  Leu  Glu  Glu  Ala  Ser  Gly
               265                           270                           275

GAG  GCT  AGT  GAG  GGA  TTT  TTG  ACC  CAG  GAA  GCA  AAG  TTT  TCC  CCC  TCC    1134
Glu  Ala  Ser  Glu  Gly  Phe  Leu  Thr  Gln  Glu  Ala  Lys  Phe  Ser  Pro  Ser
               280                           285                           290

ACG  CCT  GTA  GGG  GGC  AGC  ATC  CAG  GCA  GAG  ACT  GAC  AGA  CCC  AGG  GCC    1182
Thr  Pro  Val  Gly  Gly  Ser  Ile  Gln  Ala  Glu  Thr  Asp  Arg  Pro  Arg  Ala
               295                           300                           305

CTC  TCA  GCA  TCT  CCA  TTC  CCT  AAA  TCA  ACA  GAG  GAC  CAA  AAG  CCA  GTG    1230
Leu  Ser  Ala  Ser  Pro  Phe  Pro  Lys  Ser  Thr  Glu  Asp  Gln  Lys  Pro  Val
310                           315                      320                      325

GAT  ATA  ACA  GAC  AGG  CCG  TTG  ACA  GAG  GTG  AAC  CCT  ATG  AGA  CCC  ATT    1278
Asp  Ile  Thr  Asp  Arg  Pro  Leu  Thr  Glu  Val  Asn  Pro  Met  Arg  Pro  Ile
               330                           335                           340

GGC  CAG  ACA  CAG  AAT  AAT  ACT  CCT  GAG  AAG  ACT  GAT  GGT  ACA  TCC  ACG    1326
Gly  Gln  Thr  Gln  Asn  Asn  Thr  Pro  Glu  Lys  Thr  Asp  Gly  Thr  Ser  Thr
               345                           350                           355

CTG  CGT  GAA  GAC  CAC  CAG  GAG  CCA  GGC  TCT  CCC  CAT  ATT  GCG  ACA  CCG    1374
Leu  Arg  Glu  Asp  His  Gln  Glu  Pro  Gly  Ser  Pro  His  Ile  Ala  Thr  Pro
          360                           365                           370

AAT  CCC  CAA  CGA  GTC  AGC  AAC  TCA  GCC  ACC  CCC  GTT  GCT  CAG  TTA  CTG    1422
Asn  Pro  Gln  Arg  Val  Ser  Asn  Ser  Ala  Thr  Pro  Val  Ala  Gln  Leu  Leu
     375                      380                      385

CTT  CCC  AAA  AGC  CAC  TCT  TGG  GGC  ATT  GTG  CTG  CCC  CTT  GGG  GAG  CTT    1470
Leu  Pro  Lys  Ser  His  Ser  Trp  Gly  Ile  Val  Leu  Pro  Leu  Gly  Glu  Leu
390                           395                      400                      405

GAG  GGC  AAG  AGA  AGT  ACC  AGG  GAT  CGA  AGG  AGC  CCC  GCA  GAG  CTG  GAA    1518
Glu  Gly  Lys  Arg  Ser  Thr  Arg  Asp  Arg  Arg  Ser  Pro  Ala  Glu  Leu  Glu
               410                           415                           420

GGA  GGA  TCA  GCA  AGT  GAG  GGG  GCA  GCC  AGG  CCT  GTG  GCC  CGT  TTT  AAT    1566
Gly  Gly  Ser  Ala  Ser  Glu  Gly  Ala  Ala  Arg  Pro  Val  Ala  Arg  Phe  Asn
               425                           430                           435

TCC  ATT  CCT  TTG  ACT  GAC  ACA  GGC  CAT  GTG  GAG  CAG  CAT  GAG  GGA  TCC    1614
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Ser | Ile | Pro | Leu | Thr | Asp | Thr | Gly | His | Val | Glu | Gln | His | Glu | Gly | Ser  |
|     |     | 440 |     |     |     |     |     | 445 |     |     |     |     | 450 |     |      |
| TCT | GAC | CCC | CAG | ATC | CCT | GAG | TCT | GTC | TTC | CAC | CTG | CTG | GTG | CCG | GGC  | 1662 |
| Ser | Asp | Pro | Gln | Ile | Pro | Glu | Ser | Val | Phe | His | Leu | Leu | Val | Pro | Gly  |
|     | 455 |     |     |     |     | 460 |     |     |     |     | 465 |     |     |     |      |
| ATC | ATC | CTA | GTC | TTG | CTG | ACT | GTT | GGG | GGC | CTC | CTG | TTC | TAC | AAG | TGG  | 1710 |
| Ile | Ile | Leu | Val | Leu | Leu | Thr | Val | Gly | Gly | Leu | Leu | Phe | Tyr | Lys | Trp  |
| 470 |     |     |     |     | 475 |     |     |     |     | 480 |     |     |     |     | 485  |
| AAG | TGG | AGG | AGC | CAT | CGA | GAC | CCT | CAG | ACA | TTG | GAT | TCT | TCT | GTG | GGG  | 1758 |
| Lys | Trp | Arg | Ser | His | Arg | Asp | Pro | Gln | Thr | Leu | Asp | Ser | Ser | Val | Gly  |
|     |     |     |     | 490 |     |     |     |     | 495 |     |     |     |     | 500 |      |
| CGA | CCA | GAG | GAC | AGC | TCC | CTG | ACC | CAG | GAT | GAG | GAC | AGA | CAG | GTG | GAA  | 1806 |
| Arg | Pro | Glu | Asp | Ser | Ser | Leu | Thr | Gln | Asp | Glu | Asp | Arg | Gln | Val | Glu  |
|     |     |     | 505 |     |     |     |     | 510 |     |     |     |     | 515 |     |      |
| CTG | CCA | GTA | T AGAAAGGATT CTATGCTGGG CACACAGGAC TATCTCTTTA | | | | | | | | | | | | 1856 |
| Leu | Pro | Val |     |     |     |     |     |     |     |     |     |     |     |     |      |
|     |     | 520 |     |     |     |     |     |     |     |     |     |     |     |     |      |

| | | | | |
|---|---|---|---|---|
| TGGAAGGAGA | CATATGGGAA | CATCCACCAC | TACCCTCTCC | TACCATCTTC CTGGGAATGT | 1916 |
| GGCCTACCAC | TACCAGAGCT | CCTGCCTACC | AAGACTGGAT | GAAAGAAGCA GCTTTGATGG | 1976 |
| GGTCTTTCCA | TCCTCACCCT | TAGACTCTCA | ACCAAAGAGA | AAGGGCTGGA GGATGCCCCC | 2036 |
| CACATACTGC | CACTATTTAT | TGTGGGCCCT | GGAGGCTCCC | TGCATTGGAG AAGGGCAGC | 2096 |
| TCAGCAGCTC | AGGACCCTTT | CCCTTAGGGG | CTGCTTCCTC | CCCTCAAAAC CAGAACCTGG | 2156 |
| CAAGGGACTC | ACTAGCCTGG | ATGGCCCATG | GGAGACCAGG | ACAGATGAGA AGGAGCAGAA | 2216 |
| GAGCCCTGTG | CCCAGAAGAC | CCAACTGGTG | CCAAGGAATC | CCAGCATGGA CAGGCAGGGA | 2276 |
| CCTGTTTCCC | AAGAAGAGAG | CCTGATATTC | AAAGGGTGGG | ACAGCATCTG CCCGACTTCC | 2336 |
| CGTAAAGGCA | TAAAGGCACG | CAGCCCAAAA | GACGGGAAGA | GGAGGCCTTT GGCTGCTTGT | 2396 |
| GTTGACAGCT | TAAAGGGGTC | TACACCCTCA | ACTTGCTTAA | GTGCCCTCTG CTGATAGCCA | 2456 |
| GGAAGGAGGG | AGACCAGCCC | TGCCCCTCAG | GACCTGACCT | GGCTCATGAT GCCAAGAGGA | 2516 |
| AGACAGAGCT | CTAGCCTCGT | CTTCTCCTGC | CCACAGCCCC | TGCCAGAGTT CTTTTGCCCA | 2576 |
| GCAGAGGCAC | CCCTCATGAA | GGAAGCCATT | GCACTGTGAA | TACTGAACCT GCCTGCTGAA | 2636 |
| CAGCCTGTCC | CATCCATCCC | TATGAGTGAC | CATCCGTCCG | AATGTTCTCC CACTTCCTTC | 2696 |
| AGCCTCTCCT | CGGCTTCTTG | CACTGAGCTG | GCCTCACGTG | TTGACTGAGG GAGCCCCTGA | 2756 |
| GCCCCAACCT | TCCCTGCCT | CAGCCTTTGA | TTGTCCAGGG | TGAAGCTGTG GGAGAAACGC | 2816 |
| CTGGGCTACC | AGTCAGAGCT | GGTCTTTGGG | CTGTGTTCCT | TGCCCAGGTT TCTGCATCTT | 2876 |
| GCACTTTGAC | ATTCCCAGGA | GGGAAGTGAC | TAGTGGAAGG | GAGAGAGGAA GGGGAGGCAG | 2936 |
| AGACAAAGGC | CACAGGCAGA | GCTATGAATG | AGAATGGGTC | TTGAAAATAT GTGTGCACCC | 2996 |
| CTAAGCTTGA | AATTGATCTC | TATACTCTAG | CCCCTCAGCC | AGCCTCCTTC CTGTTGTCTG | 3056 |
| AAACCTGGAG | CTAAGCAGGT | TGTCCTGTCA | CAAGCTCTGG | GGACTGAGCT CCATGCTCCA | 3116 |
| ACCCCACCCT | CTTCTGACCT | TTGTTCTCCA | GACCTGACCC | AGGTAGGCAA GGGTACCCTC | 3176 |
| CCAGTCTCAC | CTACCATACT | GTGCCATCTC | TAGCCAAGCA | AGCCAGGTTT AGAGAAGGGT | 3236 |
| CAAAAAAAA | AAAAAGGGT | TGTTTACTTC | CAACTTGTTC | TGATGCCCTC TGTTTCCCAG | 3296 |
| GCCAGGCTTG | TCTGTGGTGA | CCTGGGCATG | GGTGACAGGG | CTCTCATTTG CCCCTTGGTC | 3356 |
| TCTTTATGCT | GCTGAGTCCC | CCTTTCCTGC | CCTCCCTGGC | TACTGGGTCA ATAATCTTTC | 3416 |
| AGGCCATGAA | TCTGGGAGGA | GAGTGGTCTG | TAAGCTCCAT | CAGCCCTGTC CTGAGACAGC | 3476 |
| AGGGGGGAAG | GACACTGGAG | ACTTTCTTGT | GGGGCTTACT | TAGCCTTCTG GTTACAGACT | 3536 |
| ATTTCCATGC | TAGAAAATAC | ATATTTTAAA | ATAGAAGGAA | AAACACAGAA ACAAAACAAA | 3596 |

| | | | | |
|---|---|---|---|---|
| ACAAGGCATT | CTCTACCCCT | CCACCTTAAA | CATATATTAT | TAAAGACAGA | AGAGAAAATC | 3656 |
| CAACCCATTG | GCAAGAAGCT | CTTTGTGGGT | GCCTGGTTAC | ATCGGAGCAG | GGGAGCCTCA | 3716 |
| AATCCACCTT | TGGAGCCGCC | CCTGTGTGCA | TTAGGAACCC | TTCTCTCCTC | TGAGAAAGCT | 3776 |
| CAGAGGGAGC | ACTGCCTCAC | AAACTGTGAG | ACTGCGTTTT | TTATACTTGG | AAGTGGTGAA | 3836 |
| TTATTTATAT | AAGGTCATTT | AAATATCTAT | TTAAAAAATA | GGAAGCTGCT | TTTATATTTA | 3896 |
| ATAATAAAAG | AAGTGCACAA | GCTGCAAAAA | AAAAA | | | 3931 |

( 2 ) INFORMATION FOR SEQ ID NO:22:

( i ) SEQUENCE CHARACTERISTICS:
        ( A ) LENGTH: 552 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met  Thr  Ala  Arg  Gly  Ala  Ala  Gly  Arg  Cys  Pro  Ser  Ser  Thr  Trp  Leu
-32       -30                 -25                      -20

Gly  Ser  Arg  Leu  Leu  Leu  Val  Cys  Leu  Leu  Met  Ser  Arg  Ser  Ile  Ala
     -15                 -10                      -5

Lys  Glu  Val  Ser  Glu  His  Cys  Ser  His  Met  Ile  Gly  Asn  Gly  His  Leu
  1            5                      10                          15

Lys  Val  Leu  Gln  Gln  Leu  Ile  Asp  Ser  Gln  Met  Glu  Thr  Ser  Cys  Gln
              20                 25                      30

Ile  Ala  Phe  Glu  Phe  Val  Asp  Gln  Gln  Leu  Asp  Asp  Pro  Val  Cys
              35                 40                      45

Tyr  Leu  Lys  Lys  Ala  Phe  Phe  Leu  Val  Gln  Asp  Ile  Ile  Asp  Glu  Thr
          50                 55                      60

Met  Arg  Phe  Lys  Asp  Asn  Thr  Pro  Asn  Ala  Asn  Ala  Thr  Glu  Arg  Leu
  65                 70                      75                              80

Gln  Glu  Leu  Ser  Asn  Asn  Leu  Asn  Ser  Cys  Phe  Thr  Lys  Asp  Tyr  Glu
                    85                      90                     95

Glu  Gln  Asn  Lys  Ala  Cys  Val  Arg  Thr  Phe  His  Glu  Thr  Pro  Leu  Gln
               100                105                    110

Leu  Leu  Glu  Lys  Ile  Lys  Asn  Phe  Phe  Asn  Glu  Thr  Lys  Asn  Leu  Leu
               115                120                    125

Glu  Lys  Asp  Trp  Asn  Ile  Phe  Thr  Lys  Asn  Cys  Asn  Asn  Ser  Phe  Ala
     130                135                    140

Lys  Cys  Ser  Ser  Arg  Asp  Val  Val  Thr  Lys  Pro  Asp  Cys  Asn  Cys  Leu
145                150                     155                          160

Tyr  Pro  Lys  Ala  Thr  Pro  Ser  Ser  Asp  Pro  Ala  Ser  Ala  Ser  Pro  His
               165                     170                         175

Gln  Pro  Pro  Ala  Pro  Ser  Met  Ala  Pro  Leu  Ala  Gly  Leu  Ala  Trp  Asp
               180                     185                         190

Asp  Ser  Gln  Arg  Thr  Glu  Gly  Ser  Leu  Leu  Pro  Ser  Glu  Leu  Pro
               195                     200                         205

Leu  Arg  Ile  Glu  Asp  Pro  Gly  Ser  Ala  Lys  Gln  Arg  Pro  Pro  Arg  Ser
     210                     215                         220

Thr  Cys  Gln  Thr  Leu  Glu  Ser  Thr  Glu  Gln  Pro  Asn  His  Gly  Asp  Arg
225                     230                         235                    240

Leu  Thr  Glu  Asp  Ser  Gln  Pro  His  Pro  Ser  Ala  Gly  Gly  Pro  Val  Pro
                    245                     250                         255

Gly  Val  Glu  Asp  Ile  Leu  Glu  Ser  Ser  Leu  Gly  Thr  Asn  Trp  Val  Leu
```

|   | 260 |   |   |   |   | 265 |   |   |   |   | 270 |   |   |
|---|---|---|---|---|---|---|---|---|---|---|---|---|---|

Glu Glu Ala Ser Gly Glu Ala Ser Glu Gly Phe Leu Thr Gln Glu Ala
              275                 280                 285

Lys Phe Ser Pro Ser Thr Pro Val Gly Gly Ser Ile Gln Ala Glu Thr
    290                 295                 300

Asp Arg Pro Arg Ala Leu Ser Ala Ser Pro Phe Pro Lys Ser Thr Glu
305                 310                 315                 320

Asp Gln Lys Pro Val Asp Ile Thr Asp Arg Pro Leu Thr Glu Val Asn
                325                 330                 335

Pro Met Arg Pro Ile Gly Gln Thr Gln Asn Asn Thr Pro Glu Lys Thr
            340                 345                 350

Asp Gly Thr Ser Thr Leu Arg Glu Asp His Gln Glu Pro Gly Ser Pro
            355                 360                 365

His Ile Ala Thr Pro Asn Pro Gln Arg Val Ser Asn Ser Ala Thr Pro
        370                 375                 380

Val Ala Gln Leu Leu Leu Pro Lys Ser His Ser Trp Gly Ile Val Leu
385                 390                 395                 400

Pro Leu Gly Glu Leu Glu Gly Lys Arg Ser Thr Arg Asp Arg Arg Ser
                405                 410                 415

Pro Ala Glu Leu Glu Gly Gly Ser Ala Ser Glu Gly Ala Ala Arg Pro
                420                 425                 430

Val Ala Arg Phe Asn Ser Ile Pro Leu Thr Asp Thr Gly His Val Glu
            435                 440                 445

Gln His Glu Gly Ser Ser Asp Pro Gln Ile Pro Glu Ser Val Phe His
        450                 455                 460

Leu Leu Val Pro Gly Ile Ile Leu Val Leu Leu Thr Val Gly Gly Leu
465                 470                 475                 480

Leu Phe Tyr Lys Trp Lys Trp Arg Ser His Arg Asp Pro Gln Thr Leu
                485                 490                 495

Asp Ser Ser Val Gly Arg Pro Glu Asp Ser Ser Leu Thr Gln Asp Glu
            500                 505                 510

Asp Arg Gln Val Glu Leu Pro Val
        515                 520

( 2 ) INFORMATION FOR SEQ ID NO:23:

( i ) SEQUENCE CHARACTERISTICS:
    ( A ) LENGTH: 1987 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 70..1726

( i x ) FEATURE:
    ( A ) NAME/KEY: mat_peptide
    ( B ) LOCATION: 166..1726

( x i ) SEQUENCE DESCRIPTION: SEQ ID NO:23:

GCCACTAGCG AGCAAGGGAG CGAGCGAACC AGGGCGGCCA ACACGCCGTG CCGGGACCCA   60

GCTGCCCGT ATG ACC GCG CGG GGC GCC GCG GGG CGC TGC CCT TCT TCG   108
    Met Thr Ala Arg Gly Ala Ala Gly Arg Cys Pro Ser Ser
    -32         -30                  -25                  -20

ACA TGG CTG GGC TCC CGG CTG CTG CTG GTC TGT CTC CTC ATG AGC AGG   156
Thr Trp Leu Gly Ser Arg Leu Leu Leu Val Cys Leu Leu Met Ser Arg
    -15                 -10                  -5

| | | | | | | | | | | | | | | | | |
|---|---|---|---|---|---|---|---|---|---|---|---|---|---|---|---|---|
| AGT | ATT | GCC | AAG | GAG | GTG | TCA | GAA | CAC | TGT | AGC | CAC | ATG | ATT | GGG | AAT | 204 |
| Ser | Ile | Ala | Lys | Glu | Val | Ser | Glu | His | Cys | Ser | His | Met | Ile | Gly | Asn | |
| | 1 | | | | 5 | | | | | | | 10 | | | | |
| GGA | CAC | CTG | AAG | GTC | CTG | CAG | CAG | TTG | ATC | GAC | AGT | CAA | ATG | GAG | ACT | 252 |
| Gly | His | Leu | Lys | Val | Leu | Gln | Gln | Leu | Ile | Asp | Ser | Gln | Met | Glu | Thr | |
| | | 15 | | | | | 20 | | | | | 25 | | | | |
| TCA | TGC | CAG | ATT | GCC | TTT | GAA | TTT | GTA | GAC | CAG | GAA | CAG | CTG | GAT | GAT | 300 |
| Ser | Cys | Gln | Ile | Ala | Phe | Glu | Phe | Val | Asp | Gln | Glu | Gln | Leu | Asp | Asp | |
| 30 | | | | | 35 | | | | | 40 | | | | | 45 | |
| CCT | GTT | TGC | TAC | CTA | AAG | AAG | GCC | TTT | TTT | CTG | GTA | CAA | GAC | ATA | ATA | 348 |
| Pro | Val | Cys | Tyr | Leu | Lys | Lys | Ala | Phe | Phe | Leu | Val | Gln | Asp | Ile | Ile | |
| | | | | 50 | | | | | 55 | | | | | 60 | | |
| GAT | GAG | ACC | ATG | CGC | TTT | AAA | GAC | AAC | ACC | CCC | AAT | GCT | AAC | GCC | ACC | 396 |
| Asp | Glu | Thr | Met | Arg | Phe | Lys | Asp | Asn | Thr | Pro | Asn | Ala | Asn | Ala | Thr | |
| | | | 65 | | | | | 70 | | | | | 75 | | | |
| GAG | AGG | CTC | CAG | GAA | CTC | TCC | AAT | AAC | CTG | AAC | AGC | TGC | TTC | ACC | AAG | 444 |
| Glu | Arg | Leu | Gln | Glu | Leu | Ser | Asn | Asn | Leu | Asn | Ser | Cys | Phe | Thr | Lys | |
| | | 80 | | | | | 85 | | | | | 90 | | | | |
| GAC | TAT | GAG | GAG | CAG | AAC | AAG | GCC | TGT | GTC | CGA | ACT | TTC | CAT | GAG | ACT | 492 |
| Asp | Tyr | Glu | Glu | Gln | Asn | Lys | Ala | Cys | Val | Arg | Thr | Phe | His | Glu | Thr | |
| 95 | | | | | 100 | | | | | 105 | | | | | | |
| CCT | CTC | CAG | CTG | CTG | GAG | AAG | ATC | AAG | AAC | TTC | TTT | AAT | GAA | ACA | AAG | 540 |
| Pro | Leu | Gln | Leu | Leu | Glu | Lys | Ile | Lys | Asn | Phe | Phe | Asn | Glu | Thr | Lys | |
| 110 | | | | | 115 | | | | | 120 | | | | | 125 | |
| AAT | CTC | CTT | GAA | AAG | GAC | TGG | AAC | ATT | TTT | ACC | AAG | AAC | TGC | AAC | AAC | 588 |
| Asn | Leu | Leu | Glu | Lys | Asp | Trp | Asn | Ile | Phe | Thr | Lys | Asn | Cys | Asn | Asn | |
| | | | | 130 | | | | | 135 | | | | | 140 | | |
| AGC | TTT | GCT | AAG | TGC | TCT | AGC | CGA | GAT | GTG | GTG | ACC | AAG | CCT | GAT | TGC | 636 |
| Ser | Phe | Ala | Lys | Cys | Ser | Ser | Arg | Asp | Val | Val | Thr | Lys | Pro | Asp | Cys | |
| | | | 145 | | | | | 150 | | | | | 155 | | | |
| AAC | TGC | CTG | TAC | CCT | AAA | GCC | ACC | CCT | AGC | AGT | GAC | CCG | GCC | TCT | GCC | 684 |
| Asn | Cys | Leu | Tyr | Pro | Lys | Ala | Thr | Pro | Ser | Ser | Asp | Pro | Ala | Ser | Ala | |
| | | 160 | | | | | 165 | | | | | 170 | | | | |
| TCC | CCT | CAC | CAG | CCC | CCC | GCC | CCC | TCC | ATG | GCC | CCT | CTG | GCT | GGC | TTG | 732 |
| Ser | Pro | His | Gln | Pro | Pro | Ala | Pro | Ser | Met | Ala | Pro | Leu | Ala | Gly | Leu | |
| 175 | | | | | 180 | | | | | 185 | | | | | | |
| GCT | TGG | GAT | GAT | TCT | CAG | AGG | ACA | GAG | GGC | AGC | TCC | CTC | TTG | CCC | AGT | 780 |
| Ala | Trp | Asp | Asp | Ser | Gln | Arg | Thr | Glu | Gly | Ser | Ser | Leu | Leu | Pro | Ser | |
| 190 | | | | | 195 | | | | | 200 | | | | | 205 | |
| GAG | CTT | CCC | CTT | CGC | ATA | GAG | GAC | CCA | GGC | AGT | GCC | AAG | CAG | CGA | CCA | 828 |
| Glu | Leu | Pro | Leu | Arg | Ile | Glu | Asp | Pro | Gly | Ser | Ala | Lys | Gln | Arg | Pro | |
| | | | | 210 | | | | | 215 | | | | | 220 | | |
| CCC | AGG | AGT | ACC | TGC | CAG | ACC | CTC | GAG | TCA | ACA | GAG | CAA | CCA | AAC | CAT | 876 |
| Pro | Arg | Ser | Thr | Cys | Gln | Thr | Leu | Glu | Ser | Thr | Glu | Gln | Pro | Asn | His | |
| | | | 225 | | | | | 230 | | | | | 235 | | | |
| GGG | GAC | AGA | CTC | ACT | GAG | GAC | TCA | CAA | CCT | CAT | CCT | TCT | GCG | GGG | GGG | 924 |
| Gly | Asp | Arg | Leu | Thr | Glu | Asp | Ser | Gln | Pro | His | Pro | Ser | Ala | Gly | Gly | |
| | | 240 | | | | | 245 | | | | | 250 | | | | |
| CCC | GTC | CCT | GGG | GTG | GAA | GGC | ATT | CTT | GAA | TCT | TCA | CTG | GGC | ACT | AAC | 972 |
| Pro | Val | Pro | Gly | Val | Glu | Gly | Ile | Leu | Glu | Ser | Ser | Leu | Gly | Thr | Asn | |
| 255 | | | | | 260 | | | | | 265 | | | | | | |
| TGG | GTC | CTA | GAA | GAA | GCT | TCT | GGA | GAG | GCT | AGT | GAG | GGA | TTT | TTG | ACC | 1020 |
| Trp | Val | Leu | Glu | Glu | Ala | Ser | Gly | Glu | Ala | Ser | Glu | Gly | Phe | Leu | Thr | |
| 270 | | | | | 275 | | | | | 280 | | | | | 285 | |
| CAG | GAA | GCA | AAG | TTT | TCC | CCC | TCC | ACG | CCT | GTA | GGG | GGC | AGC | ATC | CAG | 1068 |
| Gln | Glu | Ala | Lys | Phe | Ser | Pro | Ser | Thr | Pro | Val | Gly | Gly | Ser | Ile | Gln | |
| | | | | 290 | | | | | 295 | | | | | 300 | | |
| GCA | GAG | ACT | GAC | AGA | CCC | AGG | GCC | CTC | TCA | GCA | CCT | CCA | TTC | CCT | AAA | 1116 |
| Ala | Glu | Thr | Asp | Arg | Pro | Arg | Ala | Leu | Ser | Ala | Pro | Pro | Phe | Pro | Lys | |
| | | | 305 | | | | | 310 | | | | | 315 | | | |

| | | | | | | | | | | | | | | | | |
|---|---|---|---|---|---|---|---|---|---|---|---|---|---|---|---|---|
| TCA | ACA | GAG | GAC | CAA | AAG | CCA | GTG | GAT | ATA | ACA | GAC | AGG | CCG | TTG | ACA | 1164 |
| Ser | Thr | Glu | Asp | Gln | Lys | Pro | Val | Asp | Ile | Thr | Asp | Arg | Pro | Leu | Thr | |
| | | 320 | | | | | 325 | | | | | 330 | | | | |
| GAG | GTG | AAC | CCT | ATG | AGA | CCC | ATT | GGC | CAG | ACA | CAG | AAT | AAT | ACT | CCT | 1212 |
| Glu | Val | Asn | Pro | Met | Arg | Pro | Ile | Gly | Gln | Thr | Gln | Asn | Asn | Thr | Pro | |
| | 335 | | | | | 340 | | | | | 345 | | | | | |
| GAG | AAG | ACT | GAT | GGT | ACA | TCC | ACG | CTG | CGT | GAA | GAC | CAC | CAG | GAG | CCA | 1260 |
| Glu | Lys | Thr | Asp | Gly | Thr | Ser | Thr | Leu | Arg | Glu | Asp | His | Gln | Glu | Pro | |
| 350 | | | | | 355 | | | | | 360 | | | | | 365 | |
| GGC | TCT | CCC | CAT | ATT | GCG | ACA | CCG | AAT | CCC | CAA | CGA | GTC | AGC | AAC | TCA | 1308 |
| Gly | Ser | Pro | His | Ile | Ala | Thr | Pro | Asn | Pro | Gln | Arg | Val | Ser | Asn | Ser | |
| | | | | 370 | | | | | 375 | | | | | 380 | | |
| GCC | ACC | CCC | GTT | GCT | CAG | TTA | CTG | CTT | CCC | AAA | AGC | CAC | TCT | TGG | GGC | 1356 |
| Ala | Thr | Pro | Val | Ala | Gln | Leu | Leu | Leu | Pro | Lys | Ser | His | Ser | Trp | Gly | |
| | | | 385 | | | | | | 390 | | | | | 395 | | |
| ATT | GTG | CTG | CCC | CTT | GGG | GAG | CTT | GAG | GGC | AAG | AGA | AGT | ACC | AGG | GAT | 1404 |
| Ile | Val | Leu | Pro | Leu | Gly | Glu | Leu | Glu | Gly | Lys | Arg | Ser | Thr | Arg | Asp | |
| | | | 400 | | | | | 405 | | | | | 410 | | | |
| CGA | AGG | AGC | CCC | GCA | GAG | CTG | GAA | GGA | GGA | TCA | GCA | AGT | GAG | GGG | GCA | 1452 |
| Arg | Arg | Ser | Pro | Ala | Glu | Leu | Glu | Gly | Gly | Ser | Ala | Ser | Glu | Gly | Ala | |
| | 415 | | | | | 420 | | | | | 425 | | | | | |
| GCC | AGG | CCT | GTG | GCC | CGT | TTT | AAT | TCC | ATT | CCT | TTG | ACT | GAC | ACA | GGC | 1500 |
| Ala | Arg | Pro | Val | Ala | Arg | Phe | Asn | Ser | Ile | Pro | Leu | Thr | Asp | Thr | Gly | |
| 430 | | | | | 435 | | | | | 440 | | | | | 445 | |
| CAT | GTG | GAG | CAG | CAT | GAG | GGA | TCC | TCT | GAC | CCC | CAG | ATC | CCT | GAG | TCT | 1548 |
| His | Val | Glu | Gln | His | Glu | Gly | Ser | Ser | Asp | Pro | Gln | Ile | Pro | Glu | Ser | |
| | | | | 450 | | | | | 455 | | | | | 460 | | |
| GTC | TTC | CAC | CTG | CTG | GTG | CCG | GGC | ATC | ATC | CTA | GTC | TTG | CTG | ACT | GTT | 1596 |
| Val | Phe | His | Leu | Leu | Val | Pro | Gly | Ile | Ile | Leu | Val | Leu | Leu | Thr | Val | |
| | | | 465 | | | | | 470 | | | | | 475 | | | |
| GGG | GGC | CTC | CTG | TTC | TAC | AAG | TGG | AAG | TGG | AGG | AGC | CAT | CGA | GAC | CCT | 1644 |
| Gly | Gly | Leu | Leu | Phe | Tyr | Lys | Trp | Lys | Trp | Arg | Ser | His | Arg | Asp | Pro | |
| | | | 480 | | | | | 485 | | | | | 490 | | | |
| CAG | ACA | TTG | GAT | TCT | TCT | GTG | GGG | CGA | CCA | GAG | GAC | AGC | TCC | CTG | ACC | 1692 |
| Gln | Thr | Leu | Asp | Ser | Ser | Val | Gly | Arg | Pro | Glu | Asp | Ser | Ser | Leu | Thr | |
| | | 495 | | | | | 500 | | | | | 505 | | | | |
| CAG | GAT | GAG | GAC | AGA | CAG | GTG | GAA | CTG | CCA | GTA | T AGAAAGGATT | | | | | 1736 |
| Gln | Asp | Glu | Asp | Arg | Gln | Val | Glu | Leu | Pro | Val | | | | | | |
| 510 | | | | | 515 | | | | | 520 | | | | | | |

| | | | |
|---|---|---|---|
| CTATGACCCC | TCACCATCCT | GGACACACTC | GTTTGTCAAT | GTCCCTCTGA AAATGTGGCG | 1796 |
| CCCAGCCCTG | GACACAGTAC | TCCAGATGTT | GTCTGACCAG | CTCAGAGTAC AGTGGGACGG | 1856 |
| TTGTCTTCCT | TGATCTGGAC | AGTACTCTTC | TACTCGTGCA | GATTAAGATC ACATTAGTTT | 1916 |
| TAACAGCTGC | ATCATATATT | GTCATATGTT | GAGCTTGTAG | TCTATTAAAA ACCCCAGTTC | 1976 |
| TAAAAAAAAA | A | | | | 1987 |

( 2 ) INFORMATION FOR SEQ ID NO:24:

( i ) SEQUENCE CHARACTERISTICS:
        ( A ) LENGTH: 552 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

| | | | | | | | | | | | | |
|---|---|---|---|---|---|---|---|---|---|---|---|---|
| Met | Thr | Ala | Arg | Gly | Ala | Ala | Gly | Arg | Cys | Pro | Ser | Ser | Thr | Trp | Leu |
| -32 | | -30 | | | | -25 | | | | | -20 | | | | |
| Gly | Ser | Arg | Leu | Leu | Leu | Val | Cys | Leu | Leu | Met | Ser | Arg | Ser | Ile | Ala |
| | -15 | | | | | -10 | | | | | -5 | | | | |

```
Lys Glu Val Ser Glu His Cys Ser His Met Ile Gly Asn Gly His Leu
 1               5                   10                  15
Lys Val Leu Gln Gln Leu Ile Asp Ser Gln Met Glu Thr Ser Cys Gln
             20                  25                  30
Ile Ala Phe Glu Phe Val Asp Gln Glu Gln Leu Asp Asp Pro Val Cys
         35                  40                  45
Tyr Leu Lys Lys Ala Phe Phe Leu Val Gln Asp Ile Ile Asp Glu Thr
     50                  55                  60
Met Arg Phe Lys Asp Asn Thr Pro Asn Ala Asn Ala Thr Glu Arg Leu
 65              70                  75                      80
Gln Glu Leu Ser Asn Asn Leu Asn Ser Cys Phe Thr Lys Asp Tyr Glu
             85                  90                  95
Glu Gln Asn Lys Ala Cys Val Arg Thr Phe His Glu Thr Pro Leu Gln
            100                 105                 110
Leu Leu Glu Lys Ile Lys Asn Phe Phe Asn Glu Thr Lys Asn Leu Leu
            115                 120                 125
Glu Lys Asp Trp Asn Ile Phe Thr Lys Asn Cys Asn Asn Ser Phe Ala
            130                 135                 140
Lys Cys Ser Ser Arg Asp Val Val Thr Lys Pro Asp Cys Asn Cys Leu
145                 150                 155                 160
Tyr Pro Lys Ala Thr Pro Ser Ser Asp Pro Ala Ser Ala Ser Pro His
                165                 170                 175
Gln Pro Pro Ala Pro Ser Met Ala Pro Leu Ala Gly Leu Ala Trp Asp
            180                 185                 190
Asp Ser Gln Arg Thr Glu Gly Ser Leu Leu Pro Ser Glu Leu Pro
            195                 200                 205
Leu Arg Ile Glu Asp Pro Gly Ser Ala Lys Gln Arg Pro Pro Arg Ser
210                 215                 220
Thr Cys Gln Thr Leu Glu Ser Thr Glu Gln Pro Asn His Gly Asp Arg
225                 230                 235                 240
Leu Thr Glu Asp Ser Gln Pro His Pro Ser Ala Gly Gly Pro Val Pro
                245                 250                 255
Gly Val Glu Gly Ile Leu Glu Ser Ser Leu Gly Thr Asn Trp Val Leu
                260                 265                 270
Glu Glu Ala Ser Gly Glu Ala Ser Glu Gly Phe Leu Thr Gln Glu Ala
            275                 280                 285
Lys Phe Ser Pro Ser Thr Pro Val Gly Gly Ser Ile Gln Ala Glu Thr
    290                 295                 300
Asp Arg Pro Arg Ala Leu Ser Ala Pro Pro Phe Pro Lys Ser Thr Glu
305                 310                 315                 320
Asp Gln Lys Pro Val Asp Ile Thr Asp Arg Pro Leu Thr Glu Val Asn
                325                 330                 335
Pro Met Arg Pro Ile Gly Gln Thr Gln Asn Asn Thr Pro Glu Lys Thr
            340                 345                 350
Asp Gly Thr Ser Thr Leu Arg Glu Asp His Gln Glu Pro Gly Ser Pro
            355                 360                 365
His Ile Ala Thr Pro Asn Pro Gln Arg Val Ser Asn Ser Ala Thr Pro
    370                 375                 380
Val Ala Gln Leu Leu Leu Pro Lys Ser His Ser Trp Gly Ile Val Leu
385                 390                 395                 400
Pro Leu Gly Glu Leu Glu Gly Lys Arg Ser Thr Arg Asp Arg Arg Ser
                405                 410                 415
Pro Ala Glu Leu Glu Gly Gly Ser Ala Ser Glu Gly Ala Ala Arg Pro
```

-continued

| | | | | | | | | | | | | | | | |
|---|---|---|---|---|---|---|---|---|---|---|---|---|---|---|---|
| | | | 420 | | | | | 425 | | | | | 430 | | |
| Val | Ala | Arg | Phe | Asn | Ser | Ile | Pro | Leu | Thr | Asp | Thr | Gly | His | Val | Glu |
| | | 435 | | | | | 440 | | | | | 445 | | | |
| Gln | His | Glu | Gly | Ser | Ser | Asp | Pro | Gln | Ile | Pro | Glu | Ser | Val | Phe | His |
| | 450 | | | | | 455 | | | | | 460 | | | | |
| Leu | Leu | Val | Pro | Gly | Ile | Ile | Leu | Val | Leu | Leu | Thr | Val | Gly | Gly | Leu |
| 465 | | | | | 470 | | | | | 475 | | | | | 480 |
| Leu | Phe | Tyr | Lys | Trp | Lys | Trp | Arg | Ser | His | Arg | Asp | Pro | Gln | Thr | Leu |
| | | | | 485 | | | | | 490 | | | | | 495 | |
| Asp | Ser | Ser | Val | Gly | Arg | Pro | Glu | Asp | Ser | Ser | Leu | Thr | Gln | Asp | Glu |
| | | | 500 | | | | | 505 | | | | | 510 | | |
| Asp | Arg | Gln | Val | Glu | Leu | Pro | Val | | | | | | | | |
| | | 515 | | | | | 520 | | | | | | | | |

N-∇3 DELETION MUTANTS OF THE SHORT FORM OF CSF-1

CROSS-REFERENCE TO RELATED APPLICATIONS

This is a divisional of U.S. Ser. No. 07/999,280, filed Dec. 28, 1992, which is a continuation-in-part of U.S. Ser. No. 07/799,039 and 07/799,411, both filed Nov. 27, 1991, both now abandoned, which are continuations of U.S. Ser. No. 07/039,657, filed Apr. 16, 1987 and U.S. Ser. No. 07/105,261, filed Oct. 13, 1987, both now abandoned, which Ser. No. 07/105,261 is also a continuation-in-part of U.S. Ser. No. 07/039,654, filed Apr. 16, 1987, now abandoned, which is a continuation-in-part of U.S. Ser. No. 07/039,657, filed Apr. 16, 1987, now abandoned, which is a continuation-in-part of U.S. Ser. No. 06/923,067, filed Oct. 24, 1986, now abandoned, which is a continuation-in-part of U.S. Ser. No. 06/876,819, filed Jun. 20, 1986, now abandoned, which is a continuation-in-part of U.S. Ser. No. 06/821,068, filed Jan. 21, 1986, now abandoned, which is a continuation-in-part of U.S. Ser. No. 06/756,814, filed Jul. 18, 1985, now abandoned, which is a continuation-in-part of U.S. Ser. No. 06/744,924, filed Jun. 14, 1985, now abandoned, which is a continuation-in-part of U.S. Ser. No. 06/728,834, filed Apr. 30, 1985, now abandoned, which is a continuation-in-part of U.S. Ser. No. 06/698,359, filed Feb. 5, 1985, now abandoned.

TECHNICAL FIELD

The present invention relates to the use of recombinant technology for production of lymphokines ordinarily produced in low concentration, and of novel lymphokines. More specifically, the invention relates to the cloning and expression of new DNA sequences encoding human colony stimulating factor-1 (CSF-1) and muteins thereof.

BACKGROUND ART

For convenience of the reader, the references referred to in the text are listed numerically in parentheses. These numbers correspond to the numerical references listed in the appended bibliography. By these references, they are hereby expressly incorporated by reference herein.

The ability of certain factors produced in very low concentration in a variety of tissues to stimulate the growth and development of bone marrow progenitor cells into granulocytes and/or macrophages has been known for nearly 15 years. The presence of such factors in sera, urine samples, and tissue extracts from a number of species is demonstrable using an in vitro assay which measures the stimulation of colony formation by bone marrow cells plated in semisolid culture medium. There is no reliable known in vivo assay. Because these factors induce the formation of such colonies, the factors collectively have been called Colony Stimulating Factors (CSF).

More recently, it has been shown that there are at least four subclasses of human CSF proteins which can be defined according to the types of cells found in the resultant colonies. One subclass, CSF-1 results in colonies containing predominantly macrophages. Other subclasses produce colonies which contain both neutrophilic granulocytes and macrophages; which contain exclusively neutrophilic granulocytes; and which contain neutrophilic and eosinophilic granulocytes and macrophages.

There are murine factors analogous to the first three of the above human CSFs. In addition, a murine factor called IL-3 induces colonies from murine bone marrow cells which contain all these cell types plus megakaryocytes, erythrocytes, and mast cells, in various combinations. Human IL-3 is also known. These CSFs have been reviewed by Dexter (1), Vadas (2), Metcalf (3) and Clark (4).

The invention herein is concerned with the recombinant production of proteins which are members of the first of these subclasses, CSF-1. This subclass has been further characterized and delineated by specific radioimmunoassays and radioreceptor assays—e.g., antibodies raised against purified CSF-1 are able to suppress specifically CSF-1 activity, without affecting the biological activities of the other subclasses, and macrophage cell line J774 contains receptors which bind CSF-1 specifically. The assays are described in (5).

Purification methods for various CSF proteins have been published. Purification has been reported for a CSF protein from murine L929 cells to a specific activity of about $1\times10^8$ units/mg, which also stimulated mainly macrophage production (6). Purification of mouse L-cell CSF-1 to apparent homogeneity using a rabbit antibody column has been done (7). The first 25 amino acids of the murine sequence have been reported (8).

Purification of the CSF-1 from human urine has been described (6), and a human urinary CSF-1 obtained at a specific activity of $5\times10^7$ units/mg which produced only macrophage colonies (5). The relationship of glycosylation of the CSF-1 proteins prepared from cultured mouse L-cells and from human urine to their activities was also described (9). Human urinary CSF-1 has been isolated to a specific activity of $10^8$ U/mg (10), and to a specific activity of $0.7–2.3\times10^7$ U/mg on a rabbit antibody column (11).

A CSF protein from cultured human pancreatic carcinoma (MIAPaCa) cells was prepared which resulted in the growth of murine granulocytic and macrophagic colonies. The resulting protein had a specific activity of approximately $7\times10^7$ units/mg (12).

Partially purified preparations of various CSFs have also been reported from human and mouse lung-cell conditioned media (13, 14); from human t-lymphoblast cells (15, 16); and from human placental conditioned medium to apparent homogeneity and a specific activity of $7\times10^7$ U/mg (17).

A significant difficulty in utilizing CSF proteins in general, and CSF-1 in particular, has been their unavailability in distinct and characterizable form in sufficient amounts to make their employment in therapeutic use practical or even possible. The present invention remedies these deficiencies by providing starting materials to obtain purified human and murine CSF-1 in useful mounts through recombinant techniques.

Human and murine GM-CSF, which is a CSF protein of a different subclass, has been purified and the cDNAs cloned. This protein was shown to be distinct from other CSFs, e.g., CSF-1 (18). This GM-CSF protein is further described in PCT No. WO87/02060, published Apr. 9, 1987, as being useful to treat cancer patients to regenerate leukocytes after traditional cancer treatment, and to reduce the likelihood of viral, bacterial, fungal, and parasitic infection, such as in acquired immune deficiency syndrome (AIDS).

Murine IL-3 has been cloned (19). Human and gibbon IL-3 have also been cloned (20, 21). See also (22, 23, 24, and 25).

The cloning of a cDNA encoding a 224 amino acid form of human CSF-1, specifically the clone designated hereinbelow as pcCSF-17, is also published ((26): hereinafter Kawasaki), and in PCT No. WO86/04607, published 14

Aug. 1986. Recovery of a clone encoding a "long form" of human CSF-1 of 522 amino acids has also been reported (27, 28).

DISCLOSURE OF THE INVENTION

The invention herein relates to previously undisclosed forms of the human CSF-1 and murine CSF-1 proteins. The invention relates to additional forms of the human CSF-1 proteins from those forms specifically disclosed in the parent applications and in the Kawasaki reference (26). In addition to the specific embodiments disclosed in the Kawasaki article, represented by the 224 amino acid CSF-1 encoded by pcCSF-17 and certain specific modifications and deleted forms thereof, additional muteins of this shorter CSF-1 (SCSF) are disclosed. Also, additional modifications of the "long form" of the human CSF-1 protein (LCSF) are disclosed.

Thus, in one aspect, the invention relates to a subset of human or murine CSF-1 proteins (huCSF-1 and muCSF-1) and to DNA encoding these proteins. Some of the specific embodiments of the proteins disclosed herein contain approximately 522 amino acids, or are fragments and/or muteins derived from the native sequences of this length; other are single or double replacement muteins of the pcCSF-17 encoded protein. The human proteins related to the long form are described relative to the amino acid sequence shown in (SEQ ID NO: 2), designated LCSF. (SEQ ID NO: 2) shows the cDNA and deduced amino acid sequence for a cDNA encoding a "long form" of huCSF1 (LCSF). Those related to the short form to that shown (SEQ ID NO: 3), designated SCSF. (SEQ ID NO: 3) shows the DNA and deduced amino acid sequences for a cDNA clone encoding a "short form" of human CSF-1 (SCSF), designated pcCSF-17.

In additional aspects, the invention herein relates to a subset of human CSF-1 proteins (huCSF-1) and to the DNA encoding them. Some of the proteins of the invention have deletions at the N-terminus, and thus have the N-terminal sequence (SEQ ID NO: 5) or (SEQ ID NO: 6). Deletions from the termini are noted by N$\nabla$ followed by the number of amino acids deleted from the N-terminal sequence, or by C$\nabla$ and the last position remaining when residues are deleted from the C-terminal sequence. Thus, "SCSF/N$\nabla$4" or the "N$\nabla$4 form of SCSF" refers to CSF-1 of (SEQ ID NO: 4) wherein the first four amino acids from the N-terminus have been deleted; "SCSF/C$\nabla$130" or the "C$\nabla$130 form of SCSF" refers to CSF-1 wherein the last 94 amino acids following amino acid 130 have been deleted. The N-terminal muteins of this form have marked advantages when the CSF-1 protein is produced in bacteria. Specifically, as compared to genes encoding the "mature" forms preceded by a met start codon, genes encoding these N-terminal deleted forms in bacteria give rise to expression products which are more efficiently processed to remove the N-terminal methionine, and which are comparatively homogeneous, as judged by reverse-phase HPLC (RP-HPLC). These N$\nabla$2 and N$\nabla$3 forms also include C-terminal truncated forms and substitution muteins.

In additional aspects, the invention relates to materials and methods useful in producing these proteins, to modified microorganisms and cell lines useful in their production, to improved methods of production, to compositions containing these materials useful in pharmaceutical and therapeutic applications, to compositions containing the materials useful in pharmaceutical and therapeutic applications, and to methods of use for these compositions.

Other aspects of the invention include genomic DNA encoding the N$\nabla$2 and N$\nabla$3 forms of CSF-1 and the expression constructs and products thereof.

MODES FOR CARRYING OUT THE INVENTION

A. Definitions

Figure 1:
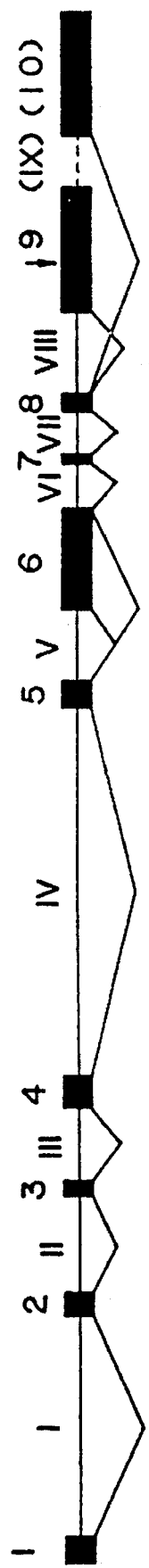
FIG. 1 is a diagram of the genome showing the origin of the short and long forms of human CSF-1.

By the term "a protein having colony stimulating factor-1 (CSF-1) activity" or grammatical equivalents herein (CSF-1 has been referred to as macrophage colony stimulating factor or "M-CSF," and it is the same molecule as "CSF-1" for the purpose of this definition) is meant a protein which exhibits the spectrum of activity understood in the art for CSF-1—i.e., when applied to the standard in vitro colony stimulating assay of Metcalf (29), it results in the formation of primarily macrophage colonies. Native CSF-1 is a glycosylated dimer; in some instances dimerization is thought to be necessary for activity. Contemplated within the scope of the invention and within the definition of CSF-1 are both the dimer and monomeric forms. The monomeric form may be converted to the dimer by in vitro provision of suitable conditions, and the monomer is per se useful as an antigen to produce anti-CSF-1 antibodies.

There appears to be some species specificity in CSF-1 proteins. Human CSF-1 is operative both on human and on murine bone marrow cells while murine CSF-1 does not show activity with human cells. Therefore, "human" CSF-1 should be positive in the specific murine radioreceptor assay of Das (5), although there is not necessarily a complete correlation. The biological activity of the protein will generally also be inhibited by neutralizing antiserum to human urinary CSF-1 (5). However, in certain special circumstances (such as, for example, where a particular antibody preparation recognizes a CSF-1 epitope not essential for biological function, and which epitope is not present in the particular CSF-1 mutein being tested) this criterion may not be met.

Certain other properties of CSF-1 have been recognized more recently, including the ability of this protein to stimulate the secretion of series E prostaglandins, intedeukin-1, and interferon from mature macrophages (30). The mechanism for these latter activities is not at present understood. Thus, for purposes of definition herein, the criterion for fulfillment of the definition resides in the ability to stimulate the formation of monocyte/macrophage colonies using bone marrow cells from the appropriate species as starting materials; and, under most circumstances (see above), the inhibition of this activity by neutralizing antiserum against purified human urinary CSF-1; and, where appropriate for species type, a positive response to the radioreceptor assay. (It is known that the proliferative effect of CSF-1 is restricted to cells of mononuclear phagocytic lineage (31), and that receptors for CSF-1 are restricted to these cell lines (32) and to placental tropoblast-related cells.

As is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Further, the primary amino acid sequence may, if such can be done without destroying activity, be modified by oxidation or reduction, or augmented by derivatization using sugar moieties (glycosylation) or by other supplementary molecules such as lipids, phosphate, acetyl groups and the like, more commonly by conjugation with saccharides.

The proteins encoded by the genes disclosed herein may also be processed by proteolysis. It is believed that CSF-1 may occur in nature in one or more C-terminally deleted forms.

The primary amino acid structure (whether clipped at the C-terminus or not) may also aggregate to form complexes, most frequently dimers. Native human urinary CSF-1 is isolated as a highly glycosylated dimer of 45–90 kd, depending on the method of measurement and identity of the reporter. Native human CSF-1 from other sources, such as monocytes, HL-60, and PanC cell lines have similar characteristics. For example, MIAPaCa-derived CSF-1 seems to be a complex mixture of glycosylated dimeric proteins with monomeric molecular weights of 70, 48, 40, 30, and 26 kd, as determined by immunoblots of SDS-PAGE. All variations of glycosylation of the monomeric and dimeric forms which retain activity are included in the definition; this includes variations in glycosylation as well as the absence of glycosylation.

Certain aspects of such augmentation are accomplished through post-translational processing systems of the producing host; other such modification may be introduced in vitro. In any event, such modifications are included in the definition so long as the activity of the protein, as defined above, is not destroyed. It is expected, of course, that such modifications may quantitatively or qualitatively affect the activity, either by enhancing or diminishing the activity of the protein in the various assays. It has been shown by applications, specifically, that the non-glycosylated monomer may have activity in some assays.

The molecular weight of the deglycosylated monomer has been studied, but definite conclusions could not be drawn in view of the difficulty of assuring lack of proteolysis during fermentation, purification, and in the deglycosylation reaction. Nevertheless, the molecular weight of this deglycosylated dimer was described to be only 14–17 kd (9). A recombinantly produced CSF-1 appears to have a molecular weight of approximately 21 kd (27). On the other hand, the molecular weight calculated on the basis of the amino acid sequence deduced for the shorter 224 amino acid form of CSF (SCSF) is on the order of 26 kd, while that of the longer form (LCSF) is calculated to be on the order of 55 kd. When deleted constructs of these genes are expressed in E. coli (where glycosylation does not occur), they, of course, give rise to proteins of considerably lower molecular weight— 17–18 kd for SCSF/C∇150, and about 30 kd for LCSF/C∇221. When LCSF or SCSF are expressed in mammalian or insect cells, higher molecular weights are obtained, but it is difficult to tell to what extent these are due to the primary amino acid sequence per se. As stated above, it appears that the natively produced protein may, in fact, contain C-terminal truncations.

It is, of course, well known that bacterially produced mature proteins which are immediately preceded by an ATG start codon may or may not include the N-terminal methionine in the form as produced and recovered. Accordingly, both forms are included. In addition, slight modification of the N-terminal sequence may aid in the processing of the N-terminal methionine, and it is shown hereinbelow that deletion of residues 1 and 2 (both glutamic acid) or residues 1–3 (glu-glu-val) aids in this manner. Accordingly, these forms are also clearly included in the definition, and form the basis for the invention.

In addition to giving expression products which are more efficiently processed at the N-terminus, the proteins produced in E. coli from genes encoding these N∇2 and N∇3 muteins are relatively homogeneous when assessed by RP-HPLC, as compared to the expression products from genes encoding forms which retain the two N-terminal glutamic acid residues. This heterogeneity may be a phenomenon associated with bacterial expression of these proteins since it does not arise when the genes are expressed in mammalian cells, such as CV-1 cells.

As to the effect of N-terminal modifications on N-terminal methionine processing, when constructs encoding the mature protein are expressed intracellularly in E. coli, it appears that essentially all of the protein produced has not been processed to remove the N-terminal methionine—i.e., all sequenceable material recovered after protein purification begins with met. However, if the corresponding constructs encoding N∇2CSF-1 muteins are expressed under similar conditions, 23% of the protein is in N-terminal met-less form. For N∇3 constructs, the percentage of protein which is processed at the N-terminus to remove the methionine increases to approximately 95%.

Figure 2:
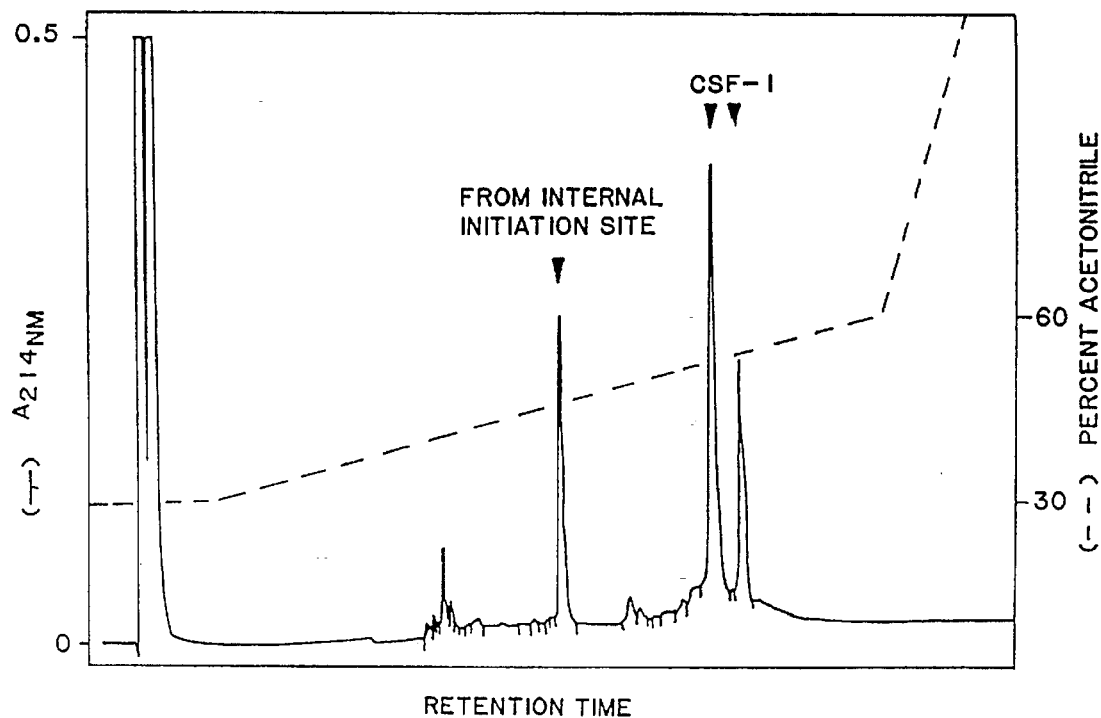
FIG. 2 shows the RP-HPLC of recombinant CSF-1 produced in E. coli from the expression of a gene encoding SCSF/C$\nabla$158.

With respect to heterogeneity, when reverse-phase HPLC analysis is performed on the reduced CSF-1 protein produced from various recombinant constructs in E. coli, constructs which encode the mature N-terminus show heterogeneity at two levels. First, there are two peaks of approximately the same molecular weight and the same apparent amino acid composition which bear approximately 70:30 area ratios. There is an additional peak resulting from an internal restart which occurs only in clones encoding tyrosine at residue 59, as shown in FIG. 2. This complication is removed by redesign of the gene upstream of position 65, as described below. Constructs encoding the N∇2 and N∇3 forms and encoding an asp at residue 59, preferably via a GAT codon, do not show the internal restart fragment and contain only protein having the retention time of the 70% peak of the mature protein compositions.

In summary, in addition to the N-terminal and C-terminal deletions and aggregations, individual amino acid residues in the chain may be modified by oxidation, reduction, or other derivatization, and these proteins may also be cleaved and/or aggregated to obtain fragments which retain activity. Such alterations which do not destroy activity do not remove the protein sequence from the definition, and are specifically included. CSF-1 derived from other species may fit the definition of a protein having activity of "human" CSF-1 by virtue of its display of the requisite pattern of activity as set forth above with regard to human substrate.

Thus, modifications to the primary structure itself by deletion, addition, or alteration of the amino acids incorporated into the sequence during translation can be made without destroying the activity of the protein. Such substitutions or other alterations result in proteins having an amino acid sequence which falls within the definition of proteins "having an amino acid sequence substantially eqiuvalent to that of CSF-1". Indeed, human and murine derived CSF-1 proteins have nonidentical but similar primary amino acid sequences which display high homology.

(SEQ ID NO: 4) shows the amino acid sequence for a particular form of human CSF-1 (SCSF) encoded by the recombinant cDNA clone pcCSF-17. This protein contains 224 amino acids in the mature sequence and a putative leader sequence of 32 amino acids which is presumably cleaved upon secretion from mammalian cells. As demonstrated herein, the protein produced as the expression product of this clone is active in assays specific for CSF-1, namely, the bone marrow proliferation assay (wherein the activity is destroyed by addition of anti-CSF-1 antibodies), colony stimulation assays, and a radioreceptor assay.

Specifically included in the definition of human CSF-1 besides SCSF are muteins which are monomers and dimers of SCSF, designated by their differences from SCSF. CSF-1 derived from other species may fit the definition of "human" CSF-1 by virtue of its display of the requisite pattern of activity as set forth above with regard to human substrate.

For convenience, with respect to the shorter form, the amino acid sequence of SCSF will be used as a reference and other sequences which are substantially equivalent to this in terms of CSF-1 activity will be designated by referring to the sequence shown in (SEQ ID NO: 2). Since the N-terminal methionine may or may not be present, both forms are included in all cases wherein the CSF-1 protein is produced in bacteria. The substitution of a particular amino acid will be noted by reference to the amino acid residue which it replaces. Thus, for example, $ser_{90}SCSF$ refers to the protein which has the sequence shown in (SEQ ID NO: 4) except that the amino acid at position 90 is serine rather than cysteine. Deletions from the termini are noted by N∇ followed by the number of amino acids deleted from the N-terminal sequence, or by C∇ and the position of the last amino acid remaining when residues are deleted from the C-terminal sequence. Thus, "SCSF/N∇4" or the "N∇4 form of SCSF" refers to CSF-1 of (SEQ ID NO: 2) wherein the first 4 amino acids from the native N-terminus have been deleted; "SCSF/C∇130" or the "C∇130 form of SCSF" refers to CSF-1 wherein the last 94 amino acids following amino acid 130 have been deleted. Illustrated below are, for example, $asp_{59}SCSF$ (which contains an aspartic acid residue encoded by the gene at position 59 rather than the tyrosine residue encoded by the cDNA) and SCSF/C∇158 which comprises only amino acids 1–158 of SCSF.

The CSF-1 proteins, which contain amino acid sequences related to those deduced from recovered long form cDNA— i.e., which include a 298 amino acid "extra" segment inserted at residue 150 of the pcCSF-17 encoded protein— are considered long forms of the protein, and the amino acid sequence shown as 1–522 in (SEQ ID NO: 2) is arbitrarily designated LCSF. Again, this may or may not be preceded by methionine when produced in *E. coli*. Notation with respect to muteins of LCSF is analogous to that described with respect to SCSF above.

The 522 amino acid sequence encoded in, for example, pcDBhuCSF4 and its corresponding clones is that of LCSF and can also be denoted huCSF-1. Expression of this cDNA results in CSF-1 activity in these specific CSF-1 assays, as well.

Thus, for convenience, the CSF-1 encoded by pcCSF-17 will be referred to as the "short form" of the protein, and the full length sequence referred to as SCSF. The 522 amino acid sequence encoded in, for example, pcDBhuCSF-4 (see below) and its corresponding clones will be referred to as the "long form", or LCSF. For the murine sequences, both recovered clones encode "long forms" containing 522 amino acids. These two closely homologous sequences are collectively designated muLCSF-1. The abbreviations used herein also include "huCSF-1" for all human forms of the protein and "muCSF-1" for murine forms thereof.

As used herein, "discrete peptide" or "mutein" refers to a particular primary amino acid sequence which is not part of a larger sequence. Thus, these terms refer to peptide molecules which do not have further N- and C- amino acid sequence extensions. The protein preparations having CSF-1 activity claimed herein may, however, be monomers, dimers, or other aggregates of these discrete peptides or muteins.

"Operably linked" refers to juxtaposition such that the normal function of the components can be performed. Thus, a coding sequence "operably linked" to control sequences refers to a configuration wherein the coding sequence can be expressed under the control Of these sequences.

"Control sequences" refers to DNA sequences necessary for the expression of an operably linked coding sequence in a particular host organism. The control sequences which are suitable for procaryotes, for example, include a promoter, optionally an operator sequence, a ribosome binding site, and possibly, other as yet poorly understood, sequences. Eucaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein, "cell", "cell line", and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell are included. Where distinct designations are intended, it will be clear from the context.

"Effective amount" signifies an amount effective to perform the function specified, such as to kill tumors or reduce tumor burden or prevent or cure infectious diseases.

B. General Description

The CSF-1 proteins of the invention are capable both of stimulating monocyte-precursor/macrophage cell production from progenitor marrow cells, thus enhancing the effectiveness of the immune system, and of stimulating such functions of these differentiated cells as the secretion of lymphokines in the mature macrophages.

In one application, these proteins are useful as adjuncts to chemotherapy. It is well understood that chemotherapeutic treatment results in suppression of the immune system. Often, although successful in destroying the tumor cells against which they are directed, chemotherapeutic treatments result in the death of the subject due to this side effect of the chemotoxic agents on the cells of the immune system.

Administration of CSF-1 to such patients, because of the ability of CSF-1 to mediate and enhance the growth and differentiation of bone marrow-derived precursors into macrophages, results in a restimulation of the immune system to prevent this side effect, and thus to prevent the propensity of the patient to succumb to secondary infection. Other patients who would be helped by such treatment include those being treated for leukemia through bone marrow transplants; they are often in an immunosuppressed state to prevent rejection. For these patients also, the immunosuppression could be reversed by administration of CSF-1.

In general, any subject suffering from immunosuppression whether due to chemotherapy, bone marrow transplantation, or other, accidental forms of immunosuppression such as disease (e.g. acquired immune deficiency syndrome) would benefit from the availability of CSF-1 for pharmacological use. In addition, subjects could be supplied enhanced amounts of previously differentiated macrophages to supplement those of the indigenous system, which macrophages are produced by in vitro culture of bone marrow or other suitable preparations treated with CSF-1. These preparations include those of the patient's own blood monocytes, which can be so cultured and returned for local or systemic therapy.

The ability of CSF-1 to stimulate production of lymphokines by macrophages and to enhance their ability to kill target cells also makes CSF-1 directly useful in treatment of neoplasms and infections.

CSF-1 stimulates the production of interferons by murine-derived macrophages (33) and human, partially purified, CSF-1 from MIAPaCa cells stimulates the poly IC-induced production of interferon and TNF from human monocytes as illustrated below. In addition, CSF-1 stimulates the production of myeloid CSF by human blood monocytes.

Also illustrated below is a demonstration of the ability of murine CSF-1 (from L-cell-conditioned medium) to stimulate normal C3H/HeN mouse peritoneal macrophages to kill murine sarcoma TU5 targets. This activity is most effective when the CSF-1 is used as pretreatment and during the effector phase. The ability of CSF-1 to do so is much greater than that exhibited by other colony stimulating factors. In addition, the ability of murine cells to attack viruses is enhanced by CSF-1.

Murine CSF-1 is inconsistently reported to stimulate murine macrophages to be cytostatic to P815 tumor cells (34) or not to kill other leukemia targets (35). CSF-1 may stimulate macrophage to ingest and kill yeast (36).

Thus, in addition to overcoming immunosuppression per se, CSF-1 can be used to destroy the invading organisms or malignant cells indirectly by stimulation of macrophage secretions and activity.

The CSF-1 of the invention may be formulated in conventional ways standard in the art for the administration of protein substances. Administration by injection is preferred; formulations include solutions or suspensions, emulsions, or solid composition for reconstitution into injectables. Suitable excipients include, for example, Ringer's solution, Hank's solution, water, saline, glycerol, dextrose solutions, and the like. In addition, the CSF-1 of the invention may be preincubated with preparations of cells in order to stimulate appropriate responses, and either the entire preparation or the supernatant therefrom introduced into the subject. As shown hereinbelow, the materials produced in response to CSF-1 stimulation by various types of blood cells are effective against desired targets, and the properties of these blood cells themselves to attack invading viruses or neoplasms may be enhanced. The subject's own cells may be withdrawn and used in this way, or, for example, monocytes or lymphokines from another compatible individual employed in the incubation.

It is preferred that the "human" forms of CSF-1 be used in pharmaceutical compositions; however, the murine forms of this protein are particularly useful in convenient model systems in mice to determine the complex pattern of CSF-1 activities.

C. Production of CSF-1 for Pharmaceutical Use

1. Retrieval of the Gene

Although the existence of a pattern of activity designated CSF-1 had been known for some time, the protein responsible had never been obtained in both sufficient purity and in sufficient amounts to permit sequence determination, nor in sufficient purity and quantity to provide a useful therapeutic function. Because neither completely pure practical amounts of the protein nor its encoding DNA have been available, it has not been possible to optimize modifications to structure by providing such alternatives as those set forth in paragraph A above, nor has it been possible to utilize this protein in a therapeutic context.

The use of recombinant techniques remedies these defects. As disclosed in PCT No. WO86/04607 (supra), probes based on the N-terminal sequences of isolated human urinary CSF-1 were used to probe the human genomic library to obtain the full-length gene. The human genomic cloned sequence can be expressed directly using its own control sequences, or in constructions appropriate to mammalian systems capable of processing introns. The genomic sequences were also used as probes for a human cDNA library obtained from a cell line which produces CSF-1 to obtain cDNA encoding this protein. The cDNA, when suitably prepared, can be expressed directly in COS or CV-1 cells and can be constructed into vectors suitable for expression in a wide range of hosts including bacteria and insect cells. As disclosed in the above application, certain modifications to primary structure also exhibit CSF-1 activity.

In addition, the human cDNA encoding the 224 amino acid form of the protein was used as a probe to recover the sequences encoding murine CSF-1 from a cDNA bank prepared in $\lambda$gt10 from L-929 mRNA which had been enriched for CSF-1 production capability. Two clones were recovered which encode similar 522 amino acid proteins. The clones diverge dramatically in the 3' untranslated region. In the longer 4 kb murine clone, the 3' untranslated region is more than 2 kb and bears little resemblance to the corresponding human sequence. The shorter 2 kb clone contains approximately 500 bp in the untranslated region and shows considerable homology to the corresponding human DNA.

These long forms of CSF-1 obtained from the murine library were then used as a basis to prepare probes to retrieve the corresponding long human sequences, whose primary structure is encoded in the genome. Based on comparison of the murine cDNAs to the human genomic sequence, a region of the gene which sometimes behaves as an intron region, was seen to encode an amino acid sequence showing considerable homology to the "extra" 298 amino acid segment contained in the murine sequence. This permitted construction of an oligonucleotide probe based on the "extra" DNA which had been, in the murine system, translated to protein. However, since the genomic sequence was available, the probe was designed to accommodate the precise human sequence.

pcCSF-17 had been prepared as an Okayama-Berg vector from MIAPaCa mRNA enriched for CSF-1-encoding materials; a subsequent cDNA library was prepared from total mRNA extracted from MIAPaCa cells and cloned into λgt10. The λgt10 library was first screened using pcCSF-17 sequences as probes, and selected probe-positive candidates were screened using an oligonucleotide probe based on the "extra" translated sequence of the murine cDNA, but modified to correspond to the related region in the human genome. Several clones encoding a corresponding "long form" of a human protein were obtained.

The "long" form apparently arises from a difference in mRNA splicing as shown in FIG. 1. The "extra" coding sequence in the mRNA arises from DNA residing at the upstream end of exon 6; it is spliced out in the short form. Various mRNA-encoded LCSFs also diverge at the 3' end (but not in protein sequence).

The cDNA encoding the "long form" of the protein from both the murine and the human systems can be expressed in manner similar to that discussed for the short form above. Suitable hosts include mammalian cells,. so as to obtain more efficient processing of the primary protein product, and, by virtue of ligation into expression vectors, bacteria, yeast, insect cells or other hosts.

Of course, the availability of DNA encoding each of these sequences provides the opportunity to modify the codon sequence so as to generate mutein forms also having CSF-1 activity.

Thus, these tools can provide the complete coding sequence for human or murine CSF-1 from which expression vectors applicable to a variety of host systems can be constructed and the coding sequence expressed. The variety of hosts available along with expression vectors suitable for such hosts permits a choice among posttranslational processing systems, and of environmental factors providing conformational regulation of the protein thus produced.

It is evident from the foregoing that portions of the CSF-1 encoding sequence are useful as probes to retrieve other CSF-1 encoding sequences in a variety of species. Accordingly, portions of the cDNA or genomic DNA encoding at least six amino acids can be replicated in *E. coli* and the denatured forms used as probes to retrieve additional DNAs encoding CSF-1. Because there may not be a precisely exact match between the nucleotide sequence in the human form and that of the corresponding potion of other species, oligomers containing approximately 18 nucleotides (encoding the 6 amino acid stretch) are probably necessary to obtain hybridization under conditions of sufficient stringency to eliminate false positives. The sequences encoding six amino acids would supply information sufficient for such probes.

D. Suitable Hosts, Control Systems and Methods

In general terms, the production of a recombinant form of CSF-1 typically involves the following:

First a DNA encoding the mature (used here to include all muteins) protein, the preprotein, or a fusion of the CSF-1 protein to an additional sequence which does not destroy its activity or to additional sequence cleavable under controlled conditions (such as treatment with peptidase) to give an active protein, is obtained. If the sequence is uninterrupted by introns it is suitable for expression in any host. If there are introns, expression is obtainable in mammalian or other eucaryotic systems capable of processing them. This sequence should be in excisable and recoverable form. The excised or recovered coding sequence is then preferably placed in operable linkage with suitable control sequences in a replicable expression vector. The vector is used to transform a suitable host and the transformed host cultured under favorable conditions to effect the production of the recombinant CSF-1. Optionally, the CSF-1 is isolated from the medium or from the cells; recovery and purification of the protein may not be necessary in some instances, where some impurities may be tolerated. For example, for in vitro cultivation of cells from which a lymphokine factor will be isolated for administration to a subject, complete purity is sometimes not required. However, direct use in therapy by administration to a subject would, of course, require purification of the CSF-1 produced.

Each of the foregoing steps can be done in a variety of ways. For example, the desired coding sequences can be obtained by preparing suitable cDNA from cellular messenger and manipulating the cDNA to obtain the complete sequence. Alternatively, genomic fragments may be obtained and used directly in appropriate hosts. The constructions for expression vectors operable in a variety of hosts are made using appropriate replication and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, insect or mammalian cells are presently useful as hosts. Since native CSF-1 is secreted as a glycosylated dimer, host systems which are capable of proper post-translational processing are preferred. While procaryotic hosts are not capable of effecting glycosylation or controlled dimerization, only if the unglycosylated form can be purified and processed to an active form would these hosts be convenient. This is, as it turns out, the case for CSF-1. CSF-1 can be produced efficiently as a monomer in *E. coli* and refolded using various techniques to an active, non-glycosylated dimeric form. Alternatively, although procaryotic hosts are in general the most efficient and convenient for the production of recombinant proteins, eucaryotic cells, and in particular, insect or mammalian cells may be preferred for their processing capacity, and for the potential recognition of the native signal sequence. For example, CSF-1 is stably produced in CHO cells, and can also be produced in stably transformed CV-1 cells and virus-infected insect cells.

In the particular case of human CSF-1, evidence now accumulating indicates that considerable deletion at the C-terminus of the protein may occur under both recombinant and native conditions, and that the in vitro activity of the protein is still retained. It appears that the native proteins isolated may be in some sort of C-terminal truncated form or mixtures thereof, and may exhibit variable C-terminal processing. The activity of these "truncated" forms is clearly established by their deliberate production. The mutein produced from DNA encoding SCSF/C∇150, for example, is fully active in assays for CSF-1, as is that produced from cDNA encoding LCSF/C∇190. The products of recombinant expression of both long and short forms of the genes seem to exhibit subunit molecular weights lower than would be expected from the full length sequence. It is believed that "natural" processing may occur at a variety of proteolytic sites, including, for example in the long form, at the arg residue at 223, the lys residue at 238, the arg residue at 249, or the arg at 411. Since it is clear that certain C terminal shortened forms are active, the constructs used may also include the corresponding shortened forms of the coding sequence.

D.1. Control Sequences and Corresponding Hosts

Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species (37). pBR322 contains genes for ampicillin and tetracycline resistance, and thus provides additional markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (38), the tryptophan (trp) promoter system (39), and the lambda derived $P_L$. promoter and N-gene ribosome binding site (40) which has been made useful as a portable control cassette, as set forth in U.S. Ser. No. 578,133, filed Feb. 8, 1984, and assigned to the same assignee. (A later filed continuation-in-part application matured into U.S. Pat. No. 4,711,845 on Dec. 8, 1987.) Also useful is the phosphotase A (phoA) system described by Chang, et at., in U.S. Ser. No. 715,653, filed Mar. 15, 1985, assigned to the same assignee and incorporated herein by reference. (U.S. Ser. No. 715,653 is now abandoned, but see EP No. 196,864 that published Oct. 8, 1986.) However, any available promoter system compatible with proearyotes can be used.

There was initially some reluctance to utilize bacterial systems in the particular case of CSF-1 in view of its high degree of posttranslational processing, which includes glycosylation and dimerization. In addition, there are a large number of cysteine residues, particularly in the N-terminal portion of the protein. There are, in fact, a total of 10 cysteine residues in the LCSF subunit, the last being at position 225; there are seven in SCSF. Both thus contain cysteine residues at positions 7, 31, 49, 90, 102, 139, 146; the long form has additional cysteines at 157, 159, and 225. It is believed that processing to form dimer includes formation of multiple intrachain and at least one interchain bond. Techniques are available, however, for refolding bacterially produced proteins of this type, and specific protocols which are surprisingly useful in preparing purified biologically active CSF-1 from bacteria are disclosed in U.S. Ser. No. 040,174, filed on Apr. 16, 1987, assigned to the same assignee; and incorporated herein by reference. (U.S. Ser. No. 040,174 is now abandoned, however, a CIP has issued as U.S. Pat. No. 4,929,700.)

In addition to bacteria, eucaryotic microbes, such as yeast, may also be used as hosts. Laboratory strains of *Saccharomyces cerevisiae*, Baker's yeast, are most used although a number of other strains are commonly available. While vectors employing the 2 micron origin of replication are illustrated (41), other plasmid vectors suitable for yeast expression are known (see, for example, (42), (43), and (44)). Control sequences for yeast vectors include promoters for the synthesis of glycolytic enzymes (45, 46). Additional promoters known in the art include the promoter for 3-phospho-glycerate kinase (47), and those for other glycolytic enzymes, such as glyceraldehyde-3-phosphate dehydrogenase, hexokinase, pyruvate decarboxylase, phosphofmctokinase, glucose-6-phosphate isomerase, 3-phosphoglycerate mutase, pymvate kinase, triosephosphate isomerase, phosphoglucose isomerase, and glucokinase. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for realrose and galactose utilization (46). It is also believed terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid pono46 (48) or the LEU2 gene obtained from YEp13 (49); however any vector containing a yeast compatible promoter, origin of replication and other control sequences is suitable.

It is also, of course, possible to express genes encoding polypeptides in eucaryofic host cell cultures derived from multicellular organisms. See, for example (50). Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (51 ), or other viral promoters such as those derived from polyoma, Adenovirus 2, bovine papilloma virus, avian sarcoma viruses, or immunoglobulin promoters and heat shock promoters. A system for expressing DNA in mammalian systems using the BPV as a vector, disclosed in U.S. Pat. No. 4,419,446, is particularly successful for CSF-1. A modification of this system is described in U.S. Pat. No. 4,601,978. General aspects of mammalian cell host system transformations have been described by Axel, U.S. Pat. No. 4,399,216, issued Aug. 16, 1983. It now also appears that "enhancer" regions are important in optimizing expression; these are, generally, sequences found upstream of the promoter region. Origins of replication may be obtained, if needed, from vital sources. However, integration into the chromosome is a common mechanism for DNA replication in eucaryotes.

Plant cells are also now available as hosts, and control sequences compatible with plant cells such as the nopaline synthase promoter and polyadenylation signal sequences (52) are available.

Recently, in addition, expression systems employing insect cells utilizing the control systems provided by baculovirus vectors have been described (53). These systems are also successful in producing CSF-1.

D.2. Transformations

Depending on the host cell used, transformation is done using standard techniques appropriate to such cells. The calcium treatment employing calcium chloride, (54), is used for procaryotes or other cells which contain substantial cell wall barriers. Infection with *Agrobacterium tumefaciens* (55) is used for certain plant cells. For mammalian cells without such cell walls, the calcium phosphate precipitation method of Graham and van der Eb (56) is preferred. Transformations into yeast are carried out according to the methods of (57) and (58).

D.3. Probing mRNA by Northern Blot; Probe of cDNA or Genomic Libraries

RNA is fractionated for Northern blot by agarose slab gel electrophoresis under fully denaturing conditions using formaldehyde (59) or 10 mM methyl mercury ($CH_3HgOH$)

(60, 61) as the denaturant. For methyl mercury gels, 1.5% gels are prepared by melting agarose in running buffer (100 mM boric acid, 6 mM sodium borate, 10 mM sodium sulfate, 1 mM EDTA, pH 8.2), cooling to 60° C. and adding 1/100 volume of 1M $CH_3HgOH$. The RNA is dissolved in 0.5×running buffer and denatured by incubation in 10 mM methyl mercury for 10 minutes at room temperature. Glycerol (20%) and bromophenol blue (0.05%) are added for loading the samples. Samples are electrophoresed for 500–600 volt-hr with recirculation of the buffer. After electrophoresis, the gel is washed for 40 minutes in 10 mM 2-mercaptoethanol to detoxify the methyl mercury, and Northern blots prepared by transferring the RNA from the gel to a membrane filter.

cDNA or genomic libraries are screened using the colony or plaque hybridization procedure. Bacterial colonies, or the plaques for phage are lifted onto duplicate nitrocellulose filter papers (S & S type BA-85). The plaques or colonies are lysed and DNA is fixed to the filter by sequential treatment for 5 minutes with 500 mM NaOH, 1.5M NaCl. The falters are washed twice for 5 min each time with 5×standard saline citrate (SSC) and are air dried and baked at 80° C. for 2 hours.

The gels for Northern blot or the duplicate filters for cDNA or genomic screening are prehybridized at 25°–42° C. for 6–8 hours with 10 ml per filter of DNA hybridization buffer without probe (0–50% formamide, 5–6×SSC, pH 7.0, 5×Denhardt's solution (polyvinylpyrrolidine, plus Ficoll and bovine serum albumin; 1×=0.02% of each), 20–50 mM sodium phosphate buffer at pH 7.0, 0.2% SDS, 20 µg/ml poly U (when probing cDNA), and 50 µg/ml denatured salmon sperm DNA). The samples are then hybridized by incubation at the appropriate temperature for about 24–36 hours using the hybridization buffer containing kinased probe (for oligomers). Longer cDNA or genomic fragment probes are labelled by nick transition or by primer extension.

The conditions of both prehybridization and hybridization depend on the stringency desired, and vary, for example, with probe length. Typical conditions for relatively long (e.g., more than 30–50 nucleotide) probes employ a temperature of 42°–55° C. and hybridization buffer containing about 20%–50% formamide. For the lower stringencies needed for oligomeric probes of about 15 nucleotides, lower temperatures of about 25°–42° C., and lower formamide concentrations (0%–20%) are employed. For longer probes, the filters may be washed, for example, four times for 30 minutes, each time at 40°–55° C. with 2×SSC, 0.2% SDS and 50 mM sodium phosphate buffer at pH 7, then washed twice with 0.2×SSC and 0.2% SDS, air dried, and are autoradiographed at −70° C. for 2 to 3 days. Washing conditions are somewhat less harsh for shorter probes.

D.4. Vector Construction

Construction of Suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution; in the examples herein, typically, an excess of restriction enzyme is used to insure complete digestion of the DNA substrate. Incubation times of about 1–2 hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in (62).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20°–25° C. in 50 mM Tris pH 7.6, 50 mM NaCl, 6 mM $MgCl_2$, 6 mM dTT and 5–10 µM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease results in hydrolysis of any single-stranded portion.

Synthetic oligonucleotides may be prepared by the triester method (63) or using automated synthesis methods. Kinasing of single strands prior to annealing or for labeling is achieved using an excess, e.g., approximately 10 units of polynucleotide kinase to 1 nM substrate in the presence of 50 mM Tris, pH 7.6, 10 mM $MgCl_2$, 5 mM dithiothreitol, 1–2 mM ATP. If kinasing is for labeling of probe, the ATP will contain high specific activity $^{32}\gamma P$.

Ligations are performed in 15–30 µl volumes under the following standard conditions and temperatures: 20 mM Tris-Cl pH 7, 10 mM $MgCl_2$, 10 mM dTT, 33 µg/ml BSA, 10 mM- 50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per µg of vector at 60° C. for about 1 hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

D.5. Modification of DNA Sequences

For portions of vectors derived from cDNA or genomic DNA which require sequence modifications, site specific primer directed mutagenesis is used. This technique is now standard in the art, and is conducted using a synthetic primer oligonucleotide complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The plaques are hybridized with kinased synthetic primer at a temperature which permits hybridization of an exact match, but which prevents hybridization when mismatches with the original strand are present. Plaques which hybridize with the probe are then picked, cultured, and the DNA recovered. Details of site specific mutation procedures are described below in specific examples.

D.6. Verification of Construction

In the constructions set forth below, correct ligations for plasmid construction are confirmed by fast transforming *E. coli* strain MM294, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to (64), optionally following chloramphenicol amplification (65). The isolated DNA is analyzed by restriction and/or sequenced by the dideoxy method of (66) as further described by (67), or by the method of (68).

D.7. Hosts Exemplified

Host strains used in cloning and expression herein are as follows:

For cloning and sequencing, and for expression of construction under control of most bacterial promoters, *E. coli* strain MM294 obtained from *E. coli* Genetic Stock Center GCSC #6135, was used as the host. For expression under control of the $P_L N_{RBS}$ promoter, *E. coli* strain K12 MC1000 lambda lysogen, $N_7 N_{53} cI857$ $SusP_{80}$, ATCC No. 39531 may be used. Used herein is *E. coli* DG116 (CMCC 2562), which is also deposited with ATCC (ATCC No. 53606).

For M13 phage recombinants, *E. coli* strains susceptible to phage infection, such as *E. coli* K12 strain dG98 are employed. The dG98 strain has been deposited with ATCC 13 Jul. 1984 and has accession No. 39768.

Mammalian expression has been accomplished in COS-7, COS-A2, CV-1, CHO cells and murine cells, and insect cell based expression in *Spodoptera frugipeida*.

E. Preferred Embodiment

The recombinant CSF-1 proteins of this invention can be considered a set of "basic" proteins and their muteins which have similar but not necessarily identical primary amino acid sequences, and various lengths, all of which exhibit, or are specifically cleavable to a mutein which exhibits, the activity pattern characteristics of CSF-1—i.e., they are capable of stimulating bone marrow cells to differentiate into monocytes, predominantly, and, within the limitations set forth in the Definitions section above, are immunoreactive with antibodies raised against native CSF-1 and with the receptors associated with CSF-1 activity.

Some specific embodiments of SCSF show that position 59 is variable between asp and tyr—i.e., in addition to the SCSF originally retrieved, included are muteins wherein the SCSF sequence is altered by substitution of asp for tyr at position 59 (i.e., $asp_{59}$ SCSF). Conversely, LCSF has asp at position 59 and can be substituted by tyr ($tyr_{59}$ LCSF).

The invention herein is directed to that class of muteins which lacks the N-terminal 2 (N∇72) or 3 (N∇73) residues from the mature sequence, and thus has an N-terminal sequence selected from the group consisting of (SEQ ID NO: 2) and (SEQ ID NO: 3). These N∇2 or N∇3 muteins may represent the corresponding N∇2, N∇3 muteins of the SCSF and LCSF mature forms—i.e., SCSF/N∇2, SCSF/N∇3, LCSF/N∇2, and LCSF/N∇3. In addition, however, the C-terminal truncated forms of these N∇2 and N∇3 mutations, as well as positionally substituted muteins, are included as further described below.

Also of particular interest are various C-terminal deletion muteins. Of particular interest are various C-terminal deletion muteins of N-terminal-deleted LCSF, $tyr_{59}$LCSF, SCSF and $asp_{59}$SCSF. It is not clear from the art to what extent the native proteins are processed from the C-terminus in vivo. It is now established that the C-terminal region at least back to amino acid 150 of SCSF can be deleted and the protein will retain in vitro CSF-1 activity in the bone marrow proliferation assay. Furthermore, it is believed that the 23 amino acid hydrophobic sequence which extends from position 166–188 in the short form and 464–486 in the long form may have a membrane anchor function and may be separated from the protein when it is transported through the membrane and secreted. This portion may also be responsible for membrane binding per se, and permit CSF-1, when bound to cell membranes to interact with other cells by binding to the CSF-1 receptor. These CSF-1 sequences independently may be dispensable in total or in part. In any event, it appears that forms of CSF-1 markedly shorter than either SCSF or LCSF are found following isolation of the native protein, and in the secreted proteins obtained from recombinant production in eucaryotic cells. Present data indicate that expression of constructs encoding SCSF in CV-1 cells may result in SCSF/C∇158 in the supernatant.

Accordingly, included within the invention are CSF-1 proteins which comprise the amino acid sequences containing only the first 150 amino acids of SCSF or LCSF or their interchangeable position 59 tyr or asp muteins as described above (which are therefore identical except for the last amino acid) or the N∇2 or N∇3 variations thereof, optionally extended by an arbitrary number of amino acids in further sequence. Among this group, particularly favored are C-terminal deletions corresponding to SCSF/C∇150, SCSF/C∇158, LCSF/C∇150, LCSF/C∇190, LCSF/C∇191, LCSF/C∇221, LCSF/C∇223, LCSF/C∇236, LCSF/C∇238, LCSF/C∇249, LCSF/C∇258, and LCSF/C∇411, and their corresponding N∇2 and N∇3 forms.

Also favored are constructions encoding above-mentioned C-terminal deletions wherein modifications of preferably 1–5 and more preferably 1–2 amino acids in the sequence from the "basic" sequence have been made.

Also preferred are the foregoing N∇2 and N∇3 C-terminal forms as well as the full-length forms wherein the lysine at position 52 is substituted by a glutamine residue—i.e. the $gln_{52}$ forms.

Thus, the various CSF-1 forms may also contain mutations which do not destroy functionality in regions which are not highly conserved among species. These are 1–5 amino acid deletions and/or substitutions in positions 15–20, 51–52, and/or 75–84. An additional such region is that of 191–193 in SCSF and 489–491 in LCSF. Specifically, it has been found that $glu_{52}$ forms of both SCSF and LCSF and their muteins are active.

It has also been shown herein that alteration of one or more glycosylation sites can result in active proteins. LCSF has four glycosylation sites—at 122–124, 140–142, 349–351, and at 383–385; SCSF has only the first two. Thus, also included is any mutein containing an inactivating mutation at one or more of these sites.

In addition, the cysteine at position 90 has been shown to be dispensable to immunoreactivity. Accordingly, muteins which are $ala_{90}$ or $ser_{90}$ are included when the purpose intended relies only on antigenicity. It is also believed that the putative membrane anchor regions of both LCSF and SCSF are dispensable for some types of CSF-1 activity.

Additional preferred forms of the invention include muteins corresponding to those set forth for the human LCSF.

E.1. Preferred Embodiments of CSF-1-Encoding DNA

In addition to modifying the amino acid sequences, the DNA sequence encoding the protein can be modified to assist expression in particular systems. In *E. coli,* for example, alterations of the codons for the first six amino acids of the native sequence to those favored in bacteria results in higher levels of production for both LCSF and SCSF and for their truncated forms. Thus, vectors (designated O/E below for "over expressing") contain DNAs of the N-terminal coding (SEQ ID NO: 2) or its N$\nabla$ or N$\nabla$3 truncaations. This is supplied as a synthetic HindIII/BstXI fragment, and differs from the native (SEQ ID NO: 8) in the underlined positions shown GAGGAGGTGT CGGAGTA C. One aspect of the invention includes providing the CSF-1-encoding DNA, when it is to be expressed intracellularly in bacteria, in a form wherein an appropriate number of codons at the N-terminus are chosen according to the rules for bacteria-preferred codons.

Also with regard to bacterial expression, the DNA sequences upstream of the ATG at position 65 can be modified to prevent use of this ATG as an internal start site. This is a more serious problem for $tyr_{59}$ than for $asp_{59}$ constructs. A primer of the sequence 5'–3' (SEQ ID NO: 9) is used in site specific mutagenesis to make the starred alterations in the native gene. No change in the amino acids encoded results.

Also favored are constructions encoding above-mentioned C-terminal deletions wherein modifications of one or more amino acids in the sequence from the "basic" sequence has been made.

Thus, also preferred are the foregoing N$\nabla$2 and N$\nabla$3 C-terminal forms as well as the full-length forms wherein the lys at position 52 is substituted by a glutamine residue—i.e., the $gln_{52}$ forms.

F. Utility and Administration

The CSF-1 proteins of the invention are capable both of stimulating monocyte-precursor/macrophage cell production from progenitor marrow cells, thus enhancing the effectiveness of the immune system, and of stimulating such functions of these differentiated cells as the secretion of lymphokines in the mature macrophages. They are also useful anti-infective agents, especially as antiviral and antimicrobial agents.

In one application, these proteins are useful as adjuncts to chemotherapy. It is well understood that chemotherapeutic treatment results in suppression of the immune system. Often, although successful in destroying the tumor cells against which they are directed, chemotherapeutic treatments result in the death of the subject due to this side effect of the chemotoxic agents on the cells of the immune system. Administration of CSF-1 to such patients, because of the ability of CSF-1 to mediate and enhance the growth and differentiation of bone marrow-derived precursors into macrophages, results in a restimulation of the immune system to prevent this side effect, and thus to prevent the propensity of the patient to Succumb to secondary infection. Other patients who would be helped by such treatment include those being treated for leukemia through bone marrow transplants; they are often in an immunosuppressed state to prevent rejection. For these patients also, the immunosuppression could be reversed by administration of CSF-1.

In general, any subject suffering from immunosuppression whether due to chemotherapy, bone marrow transplantation, or other, accidental forms of immunosuppression such as disease (e.g., acquired immune deficiency syndrome) would benefit from the availability of CSF-1 for pharmacological use. In addition, subjects could be supplied enhanced amounts of previously differentiated macrophages to supplement those of the indigenous system, which macrophages are produced by in vitro culture of bone marrow or other suitable preparations treated with CSF-1. These preparations include those of the patient's own blood monocytes, which can be so cultured and returned for local or systemic therapy.

The ability of CSF-1 to stimulate production of lymphokines by macrophages and to enhance their ability to kill target cells also makes CSF-1 directly useful in treatment of neoplasms and infections.

CSF-1 stimulates the production of interferons by murine-derived macrophage (69), and human, partially purified, CSF-1 from MIAPaCa cells stimulates the poly IC-induced production of interferon and TNF from human monocytes. CSF-1 from MIAPaCa cells stimulates the poly IC-induced production of interferon and TNF from human monocytes as illustrated below. In addition, CSF-1 stimulates the production of myeloid CSF by human blood monocytes.

Treatment of patients suffering from AIDS with CSF-1, alone or together with erythropoietin and/or an antiviral agent and/or IL-2 is reported in PCT No. WO87/03204, published Jun. 4, 1987. U.S. Pat. No. 4,482,485, issued Nov. 13, 1984, states that CSF-1 can be used in a supporting role in the treatment of cancer. In addition, EP No. 118,915, published Sep. 19, 1984, reports use of CSF-1 for preventing and treating granulocytopenia and macrophagocytopenia in patients receiving cancer therapy, for preventing infections, and for treating patients with implanted bone marrow. There is an added tumoricidal effect of a combination of CSF-1 and lymphokine on murine sarcoma TU5 targets (70).

Also illustrated below is a demonstration of the ability of murine CSF-1 (from L-cell-conditioned medium) to stimulate normal C3H/HeN mouse peritoneal macrophages to kill murine sarcoma TU5 targets. This activity is most effective when the CSF-1 is used as pretreatment and during the effector phase. The ability of CSF-1 to do so is much greater than that exhibited by other colony stimulating factors, as shown in FIG. 2 hereinbelow. In addition, the ability of murine cells to attack viruses is enhanced by CSF-1.

(Murine CSF-1 is inconsistently reported to stimulate murine macrophage to be cytostatic to P815 tumor cells (71) or not to kill other leukemia targets (72). CSF-1 may stimulate macrophage to ingest and kill yeast (73)).

Thus, in addition to overcoming immunosuppression per se, CSF-1 can be used to destroy the invading organisms or malignant cells indirectly by stimulation of macrophage secretions and activity.

CSF-1 can be employed in conjunction with another lymphokine or cytokine such as, e.g., α-IFN, β-IFN, γ-IFN, IL-1, IL-2, IL-3, IL-4, or TNF to treat tumors.

The CSF-1 of the invention may be formulated in a conventional way standard in the art for the administration of protein substances. Administration by injection is preferred; formulations include solutions or suspensions, emulsions, or solid composition for reconstitution into injectables. Suitable excipients include, for example, Ringer's solution, Hank's solution, water, saline, glycerol, dextrose solutions, and the like. In addition, the CSF-1 of the invention may be preincubated with preparations of cells in order to stimulate appropriate responses, and either the entire preparation or the supernatant therefrom introduced into the subject. As shown hereinbelow, the materials produced in response to CSF-1 stimulation by various types of blood cells are effective against desired targets, and the properties of these blood cells themselves to attack invading viruses or neoplasms may be enhanced. The subject's own cells may be withdrawn and used in this way, or, for example, monocytes or lymphocytes from another compatible individual employed in the incubation.

It is preferred that the "human" forms of CSF-1 be used in pharmaceutical compositions; however, the murine forms of this protein are particularly useful in convenient model systems in mice to determine the complex pattern of CSF-1 activities.

G. Cloning and Expression of Human CSF-1

The following illustrates the methods used in obtaining the coding sequence for human CSF-1, for disposing this sequence in expression vectors, and for obtaining expression of the desired protein. Of course, retrieval of the DNA need not be repeated; the disclosed sequences may be obtained partially or totally by synthesis.

G.1. Purification of Native Human CSF-1 and Probe Design

Human urinary CSF-1 was partially purified by methods as described in (5), followed by an affinity purification step using a rat monoclonal antibody to murine CSF-1, designated YYG106, attached to a Sepharose 4 B column (74). The final step in purification was reverse phase HPLC in a 0.1% TFA/30% acetonitrile—0.% TFA/30% acetonitrile—0.1% TFA/60% acetonitrile buffer system. The details and results of purification and design of probes are described in PCT No. WO86/04607 (supra).

For MIAPaCa CSF-1, which was produced serum-free by induction with phorbol myristic acetate, the cell supernatant was subjected to calcium phosphate gel chromatography (according to (5)), followed by affinity chromatography using lentil lectin (in place of the ConA affinity step of (5)), and then to the immunoaffinity step employing the YYG106 monoclonal antibody conjugated to Sepharose B and to the reverse phase HPLC, both as above described.

The urinary and MIAPaCa proteins, having been purified to homogeneity, were subjected to amino acid sequencing using Edman degradation on an automated sequencer. Sufficient N-terminal sequence of human CSF was determined to permit construction of probes.

In addition, the amino acid composition of the purified MIAPaCa protein was determined. Results were compared to ratios of residues/150 calculated from the SCSF encoded by pcCSF-17 designated "theoretical" in the table below. The results are as follows:

TABLE 1

| Theoretical Amino Acid Residues/150 | Mole % | Observed Residues/150 | |
|---|---|---|---|
| Cys | 4.7 | 7.2 | 7 |
| Asx | 12.5 | 19.0 | 18 |
| Thr | 5.3 | 8.1 | 8 |
| Ser | 6.6 | 10.0[1] | 12 |
| Glx | 16.6 | 25.2 | 25 |
| Pro | 3.7 | 5.6[2] | 3 |
| Gly | 2.0 | 3.1 | 3 |
| Ala | 3.4 | 5.1 | 5 |
| Val | 4.5 | 6.8[3] | 8 |
| Met | 2.4 | _3.7_ | 4[5] |
| Ile | 4.4 | 6.7 | 7 |
| Leu | 10.4 | 15.8 | 16 |
| Tyr | 4.7 | 7.2[4] | 5 |
| Phe | 5.2 | 7.9[4] | 9 |
| His | 2.1 | 3.2 | 3 |
| Lys | 7.3 | _11.1_ | _11_[5] |
| Trp | 0.5 | 0.8 | 1 |
| Arg | 3.5 | 5.3 | 5 |
| Total | 49.8 | 151.8 | 150 |

[1]10% destruction after acid hydrolysis was corrected for.
[2]Pro value was obtained from the performic acid oxidized sample.
[3]Lower valine value probably due to the sequence of Phe-Val.
[4]There was a second component coeluted with Tyr, probably galactosamine, thus interfering with the value of Tyr and Phe.
[5]Based on the human cDNA, excluding a 32 amino acid signal peptide (SEQ ID NO: 4).

G.2. Preparation of the Human Genomic Sequence

A human genomic sequence encoding CSF-1 was obtained from the Maniatis human genomic library in λphage Charon 4 using probes designed to encode the N-terminal sequence of human protein, as described in PCT No. WO86/04607 (supra). The library was constructed using partial HaeIII/AluI digestion of the human genome, ligation to EcoRI linkers, and insertion of the fragments into EcoRI digested Charon 4 phage. A Charon 4A phage containing the CSF-1 sequence as judged by hybridization to probe as described below, and designated phCSF-1, was deposited with the American Type Culture Collection (ATCC) on 2 Apr. 1985, and has accession No. 40177. Upon later study of this phage, it was found that rearrangements and/or deletions had occurred and the correct sequences were not maintained. Therefore, an alternative colony obtained from the genomic library in identical fashion, and propagated to confirm stability through replication, was designated phCSF-1a and was deposited with ATCC on 21 May 1985, and given accession No. 40185. phCSF-1a contained an 18 kb insert and was capable of generating restriction enzyme digests which also hybridized to probe, and it was used for sequence determination and additional probe construction.

If the CSF-1 encoding sequence is present in its entirety its presence can be demonstrated by expression in COS-7 cells, as described in (75). The test fragment is cloned into a plasmid derived from pBR322 which has been modified to contain the SV40 origin of replication (76). The resulting high copy number vectors are transformed into COS-7 cells and expression of the CSF-1 gene assayed after 24, 48 and 72 hours by the radioreceptor assay method described in (5). Expression is under control of the native CSF-1 control sequences. The HindIII digests of the approximately 18 kb insert of phCSF-1a tested in this manner failed to express, thus indicating that HindIII digests into the gene. This was confirmed by subsequent mapping.

For initial sequencing, a 3.9 kb HindIII fragment was partially sequenced, and the results compared to those obtained from the known protein sequence. From the genomic sequence encoding amino acids 24–34 (SEQ ID NO: 3)), a 32-mer probe for the cDNA library was constructed and employed as described below.

To obtain the genomic clone, the Maniatis library was probed using two mixtures of oligomers, EK14 and EK15:

EK14 (SEQ ID NO: 10)
EK15 (SEQ ID NO: 11)

A "full-length" probe for the N-terminal sequence, (SEQ ID NO: 10) EK14, was used as a mixture of (16) 35-mers. A shorter oligomer (SEQ ID NO: 11) EK15, was employed as a mixture of (64) 18-mers. Phage hybridizing to both Based probes were picked and cultured by infection of E. coli dG98 or other competent strain.

Specific conditions for probing with (SEQ ID NO: 10) EK14 and (SEQ ID NO: 11) EK15 are as follows: for (SEQ ID NO: 10) EK14, the buffer contained 15% formamide, 6×SSC, pH 7.0; 5×Derthardt's, 20 mM sodium phosphate, 0.2% SDS and 50 µg/ml denatured salmon sperm DNA. For EK15, similar conditions were used for hybridization and prehybridization except for the formamide concentration, which was 0%; washing was at a slightly lower temperature, 42° C.

The approximately 18 kb DNA insert isolated from the positively hybridizing phage phCSF-1a was treated with HindIII and the fragments were subjected to electrophoresis on agarose gel according to the method of Southern. The gels were replicated onto nitrocellulose filters and the filters were probed again with (SEQ ID NO: 10) EK14 and (SEQ 11) NO: 9) EK15. Both probed hybridized to a 3.9 kb fragment.

(An additional M13 subclone was obtained from the genome by digestion of the HindIII 3.9 kb fragment with PstI to generate a 1 kb PstI/PstI fragment which includes the known N-terminal sequence and about 1 kb of additional upstream sequence.)

The positive 3.9 kb fragment was excised from the gel, eluted, and subcloned into HindIII-treated M13mp19 for dideoxy sequencing.

Subsequently, the entire 18 kb gene contained in phCSF-1a was sequenced. The gene contains 9 exons separated by 8 introns when compared to the pcCSF-17 sequences of FIG. 1. The regions of the mature protein cDNA correspond exactly to the genomic exon codons except for codon 59; the "long form" of the human CSF-1 protein shows an extended coding region at the 5' end of the exon 6, as further described below.

FIG. 1 represents a schematic of the genomic structure for human CSF-1. The first exon contains untranslated 5' sequence and the first 13 amino acid residues of the signal sequence. The remaining 19 amino acids of the signal sequence and first 22 amino acids of the mature CSF protein are encoded in the second exon. The stop codon appears in exon 8, which also includes 9 bp of the 3' untranslated sequence. The gene spans approximately 18 kb and contains at least 9 exons, most likely 10, ranging in size from 63 bp to a presumed maximum of 2–3 kb. It is believed that the 3' untranslated sequence can be completed either with exon 9 or exon 10. Although two separate exons are shown, it is not clear whether there is a 9th intron and 10th exon or whether an alternative splice site is within exon 9. As will be described further below, the short form of CSF-1 results from the utilization of the splice site toward the 3' end of exon 6; the long form results from the splice site at what is shown in FIG. 1 as the beginning of that exon.

The sizes of the exons and introns illustrated in FIG. 1 are as follows:

| EXON | SIZE (bp) | INTRON | SIZE (kb) |
|---|---|---|---|
| 1 | 217 | I | 3.1 |
| 2 | 123 | II | 1.3 |
| 3 | 63 | III | 1.3 |
| 4 | 171 | IV | 4.6 |
| 5 | 148 | V | 1.2 or 2.1 |
| 6 | 1025 or 131 | VI | 0.6 |
| 7 | 49 | VII | 0.3 |
| 8 | 60 | VIII | 0.8 |
| 9 | 1400 (?) | (IX) | ? |
| (10) | ? | | |

That the genomic clone is transcribed into a number of RNA transcripts depending on the splice sites is verified by Northern analysis. MIAPaCa cells were induced under serum free conditions with 50 ng/ml PMA and 10 µM retinoic acid for 3 days in three successive inductions and mRNA was isolated after the third induction according to the general procedure described below. The mRNA isolate was electrophoresed on a 1% agarose gel containing 2.5M formaldehyde, blotted onto nitrocellulose and probed with the appropriate oligonucleotide. A number of bands, corresponding to mRNAs of 16S, 18S, 26S, 28S, and a pool at 22–25S are obtained.

MLO6, a 20-mer which corresponds to the coding sequence in exon 8 of the genome, hybridizes to the transcripts of all of these; thus verifying that all encode CSF-1. The sequences of exon 8 are, of course, common to both long and short forms. (An additional probe, GM15, a 21-mer which matches one of the murine 3' untranslated sequences that does not show homology to the human clones, does not hybridize to any of the MIAPaCa transcripts.)

GM11, a 40-mer which resides at the 5' end of long exon 6, and thus corresponds to the "extra" insert containing 894 bp in the long form sequence, hybridizes to the transcripts at 28S and the cluster at 22–25S, but not to the remaining three. Thus, apparently, these are transcripts corresponding to the long form.

A 20-mer, JV30, which matches the 5' end of exon 9 of the genome, hybridizes to the 22–25S cluster and to the 16S and 18S mRNAs, but not to the 26S or 28S. Therefore, 268 and 28S appear to result from the processing shown to include putative exon 10 in FIG. 1. An additional probe, a 4.2 kb probe made from a human CSF-1 genomic fragment which begins 1500 bp into exon 9, hybridizes only to the 26S and 28S transcripts.

The genomic fragment encoding CSF-1 can be used for expression in eucaryotic cells capable of processing introns. In order to express the genomic fragment, the insert is ligated into a suitable host vector such as a bovine papilloma virus or other mammalian virus vector immediately downstream from a suitable promoter such as the murine or human metallothionein promoter.

G.3. Retrieval of cDNA Encoding Human CSF-1pcCSF-17 (SCSF)

The human derived pancreatic carcinoma cell line MIAPaCa-2 was used as a source of mRNA to validate probes and for the formation of a cDNA library containing an intronless form of the human CSF-1 coding sequence. The MIAPaCa cell line produces CSF-1 at a level approximately 10-fold below that of the murine L-929 cells. pcCSF-17 was obtained from this library as described in PCT No. WO86/04607 and below.

Negative control mRNA was prepared from MIAPaCa cells maintained in serum-free medium, i.e., under conditions wherein they do not produce CSF-1. Cells producing CSF-1 were obtained by reinducing CSF-1 production after removal of the serum.

Cells were grown to confluence in roller bottles using Dulbecco's Modified Eagles' Medium (DMEM) containing 10% fetal calf serum, and produce CSF-1 at 2000–6000 units/ml. The cell cultures were washed, and reincubated serum-free to suppress CSF-1 formation. For negative controls, no detectable CSF-1 was produced after a day or two. Reinduced cells were obtained by addition of phorrbol myristic acetate (100 ng/ml) to obtain production after several days of 1000–2000 units/mi.

The mRNA was isolated by lysis of the cell in isotonic buffer with 0.5% NP-40 in the presence of ribonucleoside vanadyl complex (77) followed by phenol chloroform extraction, ethanol precipitation, and oligo dT chromatography, and an enriched mRNA preparation obtained. In more detail, cells are washed twice in PBS (phosphate buffered saline) and are resuspended in IHB (140 mM NACl, 10 mM Tris, 1.5 mM $MgCl_2$, pH 8) containing 10 mM vanadyl adenosine complex (77).

A nonionic detergent of the ethylene oxide polymer type (NP-40) is added to 0.5% to lyse the cellular, but not nuclear membranes. Nuclei are removed by centrifugation at 1,000×g for 10 min. The postnuclear supernatant is added to two volumes of TE (10 mM Tris, 1 mM ethylenediamine-tetraacefic acid (EDTA), pH 7.5) saturated phenol chloroform (1:1) and adjusted to 0.5% sodium dodecyl sulfate (SDS) and 10 mM EDTA. The supernatant is reextracted 4 times and phase separated by centrifugation at 2,000×g for 10 minutes. The RNA is precipitated by adjusting the sample to 0.25M NaCl, adding 2 volumes of 100% ethanol and storing at –20° C. The RNA is pelleted at 5,000×g for 30 minutes, is washed with 70% and 100% ethanol, and is then dried. Polyadenylated (poly $A^+$) messenger RNA (mRNA) is obtained from the total cytoplasmic RNA by chromatography on oligo dT cellulose (78). The RNA is dissolved in ETS (10 mM Tris, 1 mM EDTA, 0.5% SDS, pH 7.5) at a concentration of 2 mg/ml. This solution is heated to 65° C. for 5 minutes, then quickly chilled to 4° C. After bringing the RNA solution to room temperature, it is adjusted to 0.4M NaCl and is slowly passed through an oligo dT cellulose column previously equilibrated with binding buffer (500 mM NACl, 10 mM Tris, 1 mM EDTA, pH 7.5 0.05% SDS). The flowthrough is passed over the column twice more. The column is then washed with 10 volumes of binding buffer. Poly $A^+$ mRNA is eluted with aliquots of ETS, extracted once with TE-saturated phenol chloroform and is precipitated by the addition of NaCl to 0.2M and 2 volumes of 100% ethanol. The RNA is reprecipitated twice, is washed once in 70% and then in 100% ethanol prior to drying.

Total mRNA was subjected to 5–20% by weight sucrose gradient centrifugation in 10 mM Tris HCl, pH 7.4, 1 mM EDTA, and 0.5% SDS using a Beckman SW40 rotor at 20° C. and 27,000 rpm for 17 hours. The mRNA fractions were then recovered from the gradient by ethanol precipitation, and injected into Xenopus oocytes in the standard translation assay. The oocyte products of the RNa fractions were assayed in the bone marrow proliferation assay (79, 80) and the fractions themselves were assayed by dot blot hybridization to a 32-mer probe corresponding to the DNA in the second exon of the genomic sequence (exon II probe). (SEQ ID NO: 3) shows the exon II probe.)

The bone marrow proliferation assay of the supernatants from the Xenopus ooeytes did not correlate exactly with the dot-blot results. The most strongly hybridizing fraction, 11, corresponds to 18S, while the most active fractions 8 and 9 correspond to 14–16S. Fractions 8, 9, and 11 were used to form an enriched cDNA library as described below.

(The mRNA was also fractionated on a denaturing formaldehyde gel, transferred to nitrocellulose, and probed with exon II probe. Several distinct species ranging in size from 1.5 kb to 4.5 kb were found, even under stringent hybridization conditions. To eliminate the possibility of multiple genes encoding CSF-1, digests of genomic DNA with various restriction enzymes were subjected to Southern blot and probed using pcCSF-17 DNA. The restriction pattern was consistent with the presence of only one gene encoding CSF-1.)

The enriched mRNA pool was prepared by combining the mRNA from the gradient fractions having the highest bone marrow proliferative activity, although their ability to hybridize to probe is relatively low (14S-16S) with the fractions hybridizing most intensely to probe (18S). Higher molecular weight fractions which also hybridized to exon II probe were not included because corresponding mRNA from uninduced MIAPaCa cells also hybridized to exon II probe.

cDNA libraries were prepared from total or enriched human mRNA in two ways. One method uses λgt10 phage vectors and is described in (81).

Another method uses oligo dT priming of the poly A tails and AMV reverse transcriptase employing the method of (82), incorporated herein by reference. This method results in a higher proportion of full length clones than does poly dG tailing and effectively uses as host vector potions of two vectors therein described, and readily obtainable from the authors, pcDV1 and pL1. The resulting vector contain the insert between vector fragments containing proximal BamHI and XhoI restriction sites; the vector contains the pBR322 original of replication, and Amp resistance gene and SV40 control elements which result in the ability of the vector to effect expression of the inserted sequences in COS-7 cells.

A 300,000 clone library obtained from an enriched MIAPaCa mRNA by the Okayama and Berg method was then probed under conditions of high stringency, using the exon II probe derived from the genomic DNA. Ten colonies hybridizing to the probe were picked and colony purified. These clones were assayed for the presence of CSF-1 encoding sequences by transient expression in COS-7 cells. The cloning vector, which contains the SV40 promoter was used per se in the transformation of COS-7 cells.

Plasmid DNA was purified from 10 positive clones using a CsCl gradient, and COS-7 cells were transfected using a modification (83) of the calcium phosphate coprecipitation technique. After incubation for 3 days, CSF-1 production was assayed by subjecting the culture supernatants to the radioreceptor assay performed substantially as disclosed in (5), and to a colony stimulation (bone marrow proliferation) assay performed substantially as disclosed in (80). Nine of the ten clones picked failed to show transient CSF-1 production in COS-7 cells. One clone, which did show expression, was cultured, the plasmid DNA was isolated, and the insert was sequenced. The DNA sequence, along with the deduced amino acid sequence, is shown in (SEQ ID NO: 3) and (SEQ ID NO: 4), respectively. The full length cDNA is 1.64 kb and encodes a mature CSF-1 protein of 224 amino acids (SCSF), as shown in (SEQ ID NO: 4). The clone was designated CSF-17 with Cetus Depository No. CMCC 2347 and was deposited with the American Type Culture Collection on 14 Jun. 1985, as Accession No. 53149. The plasmid bearing the CSF-1 encoding DNA was designated pcCSF-17.

G.4. Clones Encoding LCSF pcCSF-17, prepared as described above, was used as a probe to obtain additional CSF-1 encoding clones from a human cDNA library. Total mRNA was prepared from MIAPaCa cells exactly as described in PCT No. WO86/04607 (supra) and used to obtain a cDNA library in λgt10 phage vectors by ligating the reverse transcripts to EcoRI linkers and inserting the EcoRI digest of the cDNA thus provided into the EcoRI site of λgt10, as described in (81).

Over one million phage were screened using a single-stranded highly labelled probe derived from CSF-17 using standard procedures, which are briefly summarized as follows.

An EcoRI fragment of pcCSF-17 DNA, which includes the entire coding sequence for CSF-1 (there is an EcoRI site immediately following the stop codon of the coding sequence in pcCSF-17) was inserted into M13, and a labelled second strand synthesized as follows: Approximately 1 pmol of M13 containing the single-stranded EcoRI-digested pcCSF-17 was annealed with 10 pmol of sequencing primer in 20 mM Tris, pH 7.9, 20 mM $MgCl_2$, 100 mM NaCl, and 20 mM β-mercaptoethanol at 67° C. for 5 minutes and then transferred to 42° C. for 45 minutes. The annealed preparation was supplied with 100 μmol each of dATP, dCTP, and dTTP, and 2.5 μmol $P^{32}$-labelled (α) dGTP, along with 5 U Klenow fragment. The reaction was incubated at 37° C. for 20 minutes, and the DNA recovered on a P-6 dG (Bio-Rad) Spin column and boiled for 10 minutes to separate the strands.

The probes, thus prepared, were used to screen the plaques (which had been transferred to nitrocellulose) by hybridization under stringent conditions (50% formamide, 5×SSC, 5×Denhardt's) at 42° C. for 18 hours.

Approximately 150 phage plaques were positive. Five of these 150 prove-positive plaques were further probe positive using the oligonucleotide JD11, a 14-mer that is complementary to the bases in the region of the exon 2 and 3 splice junction, when hybridized at 45° C. overnight in 5×SSC, 5×Denhardt's.

The 5 JD11 positive clones were then subjected to hybridization to the oligonucleotide GM11, which has the sequence complementary nucleotides 506–545 in (SEQ ID NO: 1). As described above, this sequence is an exact match to that portion of the human genomic sequence which corresponds to the "extra" portion of the murine cDNA, described in U.S. Ser. No. 923,067 (supra), that encodes the "extra" 298 amino acid segment in the "long forms" of the murine CSF-1 protein. Hybridization wa in 20% formamide, 5×SSC, 5×Denhardt's at 45° C. for 18 hours. Three clones were positive, including the relevant clones 4 and 25.

The complete DNA sequence for the pertinent coding regions of the cDNA inserts in clones 4 and 25, along with the deduced amino acid sequence, are shown in (SEQ ID NO: 1). The sequence was derived by integrating the known sequence of the genomic clone, phCSF-1a, described above, using the 298 amino acid "extra" insert of the murine sequences described below as a guide to deduce the complete sequence shown. The sequence depicted shows the splicing of the "extra" segment, sufficient to encode 298 "extra" amino acids contained in the gene at the 5' side of exon 6, in to the sequence of pcCSF-17 between the first nucleotide of the codon for the gly residue at amino acid position 150 into reading frame with the remaining CSF-17 sequence. The insert changes the codon at 150 to a codon for aspartic acid, the subsequent codon at the end of the insert is reconstituted to a gly, and the remaining sequence of residues continuing with his-glu-arg etc. down to the C-terminal val residue remain the same as in pcCSF-17. LCSF-1 is otherwise identical in sequence to SCSF-1 up to residue 150, except that it has asp rather than tyr at position 59.

Two of the clones, 4 and 25, were cloned into M13mp18 or M13mp19 for sequencing to confirm the results shown in FIG. 2 (SEQ ID NO: 1) using the EcoRI restriction sites. These two clones appeared identical from restriction enzyme analysis. The complete sequence of clone 4 was determined and is that shown in (SEQ ID NO: 1); partial sequencing of clone 25 gives consistent results. They were then subcloned into the modified Okayarea-Berg vector pcDB, which was prepared from the published Okayama-Berg vectors pcDV1 and pL1 (84) as follows:

pcDV1 was digested with HindIII and KpnI and the large fragment, providing $Amp^R$, the pBR322 origin of replication, and a polyadenylation site, was isolated. pL1 was digested with HindIII and PstI and the small fragment, providing the SV40 promoter and origin of replication, was isolated. These fragments were religated in a three-way ligation with the synthetic, KpnI/PstI-digested oligonucleotide fragment (SEQ ID NO: 12) to obtain pcDb, a plasmid corresponding to pcD-x shown in the reference, wherein "x" is replaced by a polylinker. Thus, pcDB contains the SV40 early promoter and an immediately downstream linker followed by a polyadenylation site. Sequences ligated into the polylinker region should be expressed under the control of the SV40 early promoter.

Before testing expression, because clones 4 and 25 appeared to be missing some 5' end sequences as compared to CSF-17, the upstream portions from pcCSF-17 were substituted for those of clones 4 and 25.

The protocol for this substitution was as follows: pcCSF-$asp_{59}$-BamBcl (see below) was digested with SmaI, which cuts at the extreme 5' end of the untranslated sequence (see (SEQ ID NO: 3)) and the linearized plasmid was ligated to EcoRI linkers and resealed. The religated plasmid was then digested with EcoRI, which removes the entire coding region from the SmaI site at the extreme 5' end to the EcoRI site immediately downstream of the stop codon. This was ligated into the polylinker of pcDB at the EcoRI site. The coding sequences downstream of the BstXI site, which site is located at approximately the codon for amino acid 8 of the CSF-17 mature protein sequence (see (SEQ ID NO: 3)) was removed by digestion with BstXI and KpnI. (KpnI cuts into the linker slightly downstream of the EcoRI site past the stop codon.) This deleted downstream sequence was replaced by the analogous BstI/KpnI fragment from pM13–4 and pM13–25. The resulting clones, pcDBhuCSF-4 and pcDBhuCSF-25 thus contained the coding sequences downstream of the codon for approximately amino acid 8 from clones 4 and 25, respectively, and the upstream sequences from pCSF-17. The ligated sequences are in reading frame and under control of the SV40 early promoter.

H. Mutein-Encoding Sequences/Eucaryotic Expression Vectors

Modifications were made of the pcCSF-17 inserts to provide corresponding plasmids encoding muteins of the SCSF protein. For site-specific mutagenesis, pcCSF-17 and M13mp18 were digested with the same restriction enzyme excising the appropriate region of the CSF-1 coding sequence, and the excised sequence ligated into the M13 vector. Second strand synthesis and recovery of the desired mutated DNA used the following oligonucleotide primers: for $pro_{52}$SCSF, (SEQ ID NO: 13), which creates a new HpaII site at codons 52–53; for $gln_{52}$SCSF, (SEQ ID NO: 14), which creates a new SmI site at codons 52–53; for $asp_{59}$SCSF, (SEQ ID NO: 15), which creates a new EcoRV site at codons 59–60.

After second strand extension using Klenow, the phage were transformed into *E. coli* DG98 and the resulting plaques screened with kinased labelled probe. After plaque purification, the desired mutated inserts were returned to replace the unmutated inserts in pcCSF-1, yielding pCSF-$pro_{52}$, pCSF-$gln_{52}$, and pCSF-$asp_{59}$, respectively.

Plasmids containing three deletion mutants which encode C-terminal deleted SCSF/C$\nabla$158 were also prepared: pCSF-Bam, pCSF-BamBcl, and pCSF-BamTGA. For pCSF-Bam, pcCSF-17 was digested with BamHI, and the upstream BamHI/BamHI fragment of the coding region was isolated and religated to the vector fragment. The ligation mixture was transformed into *E. coli* and the upstream BamHI/BamHI fragment of the coding region was isolated and relegated to the vector fragment. The ligation mixture was transformed into *E. coli* MM294 and plasmids with the correct orientation isolated. The resulting pCSF-Bam encodes 158 amino acids of the CSF-1 protein fused to six residues derived from the vector at the C-terminus: (SEQ ID NO: 16).

For pCSF-BamBcl, which contains the entire CSF-1 encoding sequence, except that the serine at position 159 is mutated to a stop codon, the coding sequence was excised from pcCSF-17 and ligated into M13 for site-specific mutagenesis using the primer: (SEQ ID NO: 17). This results in a new BclI site at codons 159–160. The mutated DNA was excised with BstXI/EcoRI and ligated into the BstX/EcoRI digested pcCSF-17, the ligation mixture was transformed into *E. coli* DG105, a dam host, and the plasmid DNA isolated.

For pCSF-BamTGA, in which the codons downstream of the stop at 159 are deleted, pCSF-BamBcl was digested with XhoI and BclI, and the insert ligated into XhoI/BamHI digested pcCSF-17.

In addition, pCSF-Gly$_{150}$, which contains a TGA stop codon instead of histidine at position 151 was prepared from the pcCSF-17 insert by site-specific mutagenesis using the appropriate primer, as described above. The appropriate primer is (SEQ ID NO: 18). Thus, the downstream portion of the coding sequence was excised from pcCSF-17 with BstXI/EcoRI into M13 vectors for mutagenesis, and returned after plaque purification as a BstXI/EcoRI insert.

"Double" muteins were prepared in a similar manner. Thus, for example, for pCSF-$asp_{59}$-gly$_{150}$, which encodes $asp_{59}$SCSF/C$\nabla$150, pcCSF-asp59 was digested with BstXI/EcoRI to place the C-terminal fragment into M13 for site-specific mutagenesis with the same primer as above for generation of pCSF-gly$_{150}$. The mutated fragment was then returned to the vector to obtain pCSF-1-$asp_{59}$-gly$_{150}$.

Similarly, the procedure for preparation of pCSF-BamBcl was repeated (except that pCSF-$asp_{59}$ was used instead of pcCSF as a starting plasmid) to obtain pCSF-$asp_{59}$-BamBclI.

Using the analogous techniques to those described above for preparation of pCSF-$gln_{52}$ and pCSF-$asp_{59}$, the corresponding plasmids containing the long forms of the corresponding muteins, pLCSF-$gln_{52}$ and pLCSF-$tyr_{59}$, are prepared. The procedure is as described above except that wherever pcCSF-17 is used in that procedure, pcDBhuCSF-4 or its equivalent plasmid is substituted, and the appropriate changes in primer for the $tyr_{59}$ mutein is made.

Site specific mutagenesis is also used to obtain the desired mutations at glycosylation sites of both proteins and for the replacement of cysteine at position 90; it can also be used to obtain various C-terminal deletions of the LCSF-encoding DNA.

I. Expression of pcCSF-17

The expression of plasmid DNA from CSF-17 (pcCSF-17) in COS-7 cells was confirmed and quantitated using the bone marrow proliferation assay, the colony stimulation assay and the radioreceptor assay. It will be recalled that the specificity of the bone marrow proliferation assay for CSF-1 resides only in the ability of CSF-1 antiserum to diminish activity; that for the colony stimulation assay, in the nature of the colonies obtained. Both assays showed CSF-1 production to be of the order of several thousand units per ml.

I.1. Bone Marrow Proliferation

For the bone marrow stimulation assay, which measures biological activity of the protein, bone marrow cells from Balb/C mice were treated with serial dilutions of the 72 hour supernatants and proliferation of the cells was measured by uptake of labelled thymidine, essentially as described in (79, 80). The medium from induced MIAPaCa cells was used as control. Specificity for CSF-1 was confirmed by the ability of rabbit antisera raised against human urinary CSF-1 to suppress thymidine uptake. The results for COS-7 cell supernatants transfected with pcCSF-17 (CSF-17 supernatant) at a 1:16 dilution are shown in Table 2.

TABLE 2

| | $^3$H-thymidine incorporation | | |
|---|---|---|---|
| | | (cpm) | |
| | no add'ns | normal serum | anti-human CSF-1* |
| Serum | | | |
| Medium | 861 | 786 | 2682 |
| MIAPaCa | 12255 | 16498 | 3302 |
| CSF-17 supernate | 16685 | 21996 | 2324 |

*The anti-human CSF-1 serum was prepared as described in (5).

The MIAPaCa supernatant (at the 1:16 dilution used above) contained 125 U/ml CSF activity corresponding to 2000 U/ml in the undiluted supernatant, where 1 unit of colony stimulating activity is defined as the amount of CSF needed to produce one colony from $10_5$ bone marrow cells/ml in the assay of (85).

These data show that the bone marrow stimulating activity is associated with CSF-1, since thymidine uptake is inhibited by anti-CSF-1 serum. Regression of results in this bone marrow proliferation assay obtained at four dilutions ranging from 1:8 to 1:64 gave an estimated activity for CSF-1 in CSF-17 supernatants of 2358 U/ml, which was diminished to 424 U/ml in the presence of antiserum, but showed an apparent increase to 3693 U/ml in the presence of nonimmune serum. This was comparable to the levels shown in the radioreceptor assay below.

I.2. Colony Stimulation

Direct assay of the CSF-17 supernatants for colony stimulation (87) showed 4287 U/ml, which was substantially unaffected by the presence of nonimmune serum but reduced to 0 U/ml in the presence of rabbit antihuman CSF-1. This compares to 2562 U/ml in the MIAPaCa supernatants. 85% of the pcCSF-17 transformed COS-7 supernatant induced colonies had mononuclear morphology; MIAPaCa supernatant induced colonies showed a 94% macrophage–6% granulocyte ratio.

I.3. Radioreceptor Assay

The radioreceptor assay measures competition between $^{125}$I-labelled CSF-1 and the test compound for specific receptors on J774.2 mouse macrophage cells. MIAPaCa supernatant, assayed for colony stimulating activity as above, was used as a standard (2000 U/ml). The CSF-1 concentration of the pcCSF-17 transformed COS-7 supernatant was found to be 2470 U/ml based on a 1:10 dilution and 3239 U/ml based on a 1:5 dilution.

Thus, comparable values for CSF-1 concentration in the media of COS-7 cells transformed with pcCSF-17 were found in all assays.

J. Expression of Muteins

In a similar manner to that described above for pcCSF-17, the mutein-encoding plasmids were transfected into COS-A2 cells and transient expression of CSF-1 activity assayed by the bone marrow proliferation assay and by radioimmunoassay using anti-CSF antibodies. The expression product of pCSF-pro$_{52}$ was inactive, indicating that, as expected, substitution by proline is not conservative. All other muteins showed activity in both assays as shown by the results below in Table 3.

TABLE 3

Expression of CSF-1 Constructs in COS Cells

| CSF-1 Plasmid | Radio-immunoassay (units/ml) | Bone Marrow Assay Proliferation (units/ml) | Colony (units/ml) |
|---|---|---|---|
| pcCSF-17 | 3130 | 2798 | 11,100 |
|  | 3080 | 3487 | 9,750 |
|  | 3540 | 3334 | 11,500 |
| pCSF-pro$_{52}$ | 54.8 | <25 | <100 |
|  | 51.9 | <25 | <100 |
|  | 45.3 | <25 | <100 |
| pCSF-gln$_{52}$ | 1890 | 2969 | 6200 |
|  | 2250 | 2308 | 5500 |
|  | 1910 | 2229 | 4400 |
| pCSF-asp$_{59}$ | 3210 | 3381 | 9000 |
|  | 4680 | 3417 | 6800 |
|  | 3470 | 2812 | 10,600 |
| pCSF-Bam | 9600 | 8048 | 22,600 |
|  | 8750 | 8441 | 21,900 |
|  | 8400 | 10,995 | 21,700 |
| pCSF-BamBcl | 8800 |  | 26,000 |
|  | 10,700 |  | 21,600 |
|  | 15,450 |  | 24,200 |
| pCSF-BamTGA | 8450 |  | 22,600 |
|  | 7550 |  | 23,200 |
|  | 9700 |  | 20,000 |
| pCSF-Gly$_{150}$ | 26,850 |  | 55,710 |

TABLE 4

Mouse Bone Marrow Colony Assay

| CSF-1 Plasmid |  | Colony Forming Units/ml |
|---|---|---|
| pCSF-17 | 1 | 25,000 |
|  | 2 | 25,000 |
|  | 3 | 23,500 |
| pCSF-asp$_{59}$gly$_{150}$ | 1 | 131,000 |
|  | 2 | 125,000 |
|  | 3 | 132,000 |
| pCSF-asp$_{159}$BamBcl | 1 | 72,000 |
|  | 2 | 78,000 |

J.1. Expression of pcDBhuCSF-4 and pcDBhuCSF-25

The OkayamaJBerg-type vectors containing the long form of the human CSF-1-encoding DNA (pcDBhuCSF-4 and pcDBhuCSF-25) were transfected into COS-A2 cells in a manner precisely analogous to that described for the transfection of COS-7 cells with pCSF-17 above. The supernatants of the transfected cells were analyzed for CSF-1 using radioimmunoassay with antiserum raised against CSF-1 prepared as described in (5), and also in the bone marrow proliferation assay described above. The results, in units of CSF-1 per ml, are shown in Table 5.

TABLE 5

Expression of pcDBhuCSF-4 and -25 in COS-A2 Cells

| Sample | RIA (Units/ml) | BM Assay (Units/ml) |
|---|---|---|
| pcDBhuCSF-4 | 16,979 | 9,200 |
| pcDBhuCSF-25 | 15,926 | 8,000 |
| medium | 12.5 | <50 |
| Mock infection | 25.0 | <50 |

As indicated, the supernatant of the cells transfected with either vector contained protein with CSF-1 activity.

In a similar manner, the mutein forms of these specific LCSF long form proteins are obtained.

J.2. Eucaryotic Expression of CSF-1 in Stably Transformed Cells

The COS-7 or COS-A2 systems provide recombinant CSF-1 by permitting replication of and expression from the Okayarea-Berg-type vector sequences. It is a transient expression system.

The human or murine CSF-1 sequences can also be stably expressed in procaryotic or eucaryotic systems. In general, procaryotic hosts offer ease of production, while eucaryotes permit the use of the native signal sequence to effect secretion and carry out any desired posttranslational processing. This may be important in the case of CSF-1 since the native protein is a dimer. Bacteria would produce CSF-1 as a monomer, which could then be subjected to dimerizing conditions after extraction, if needed.

The Okayarea-Berg plasmid pcCSF-17, or the analogous vectors containing the DNA encoding muteins, e.g., pCSF-asp$_{59}$-gly$_{150}$ and pCSF-asp$_{59}$-BamBcl, or the analogous vectors pcDBhuCSF4, pcDBhuCSF-25, pcDBmuCSF-L, and pcDBmuCSF-S, or other vectors encoding muteins of LCSF, containing the cDNA encoding CSF-1 under control of the SV40 promoter, can also be used to effect stable expression in monkey CV-1 cells, the parent cell line from which the COS-7 line was derived. The host monkey CV-1 cells are grown to confluence and then cotransformed using 10 µg pcCSF-17 or the analogous vectors set forth above, and various amounts (1, 2, 5, and 10 µg) of pRSV-NEO2 (86) per 500,000 cells. The transformants are grown in DMEM with 10% FBS medium containing 100 µg/ml of G418 antibiotic; to which the pRSV-NEO2 plasmid confers resistance. The CV-1 cell line shows a G418 transformations frequency of about $10_{-5,12}$ colonies per $10^6$ cells per µg DNA.

The CV-1 cells are cotransformed as described above and selected in G418-containing medium. Resistant clones are tested for stability of the G418-resistant phenotype by growth in G418-free medium and then returned to G418-containing medium. The ability of these cultures to survive when returned to antibiotic-containing medium suggests that the pRSV-NEO2 DNA is integrated permanently into the cell genome. Since cells stably transformed with a marker plasmid have about 50% probability of having integrated the DNA of a cotransfecting plasmid, about half of these cells will also contain pcCSF-17, or analogous CSF-1 "long form" encoding vector DNA, in their chromosomal DNA.

Several clones of the G418-resistant pools of CV-1 cells which are demonstrated to be stably transformed as above are picked and grown in duplicate flasks to near confluence. One flask of each duplicate is infected with SV40 virus at a multiplicity of infection of 5, and the medium is harvested 6 days after infection for assay for CSF-1 using a radioimmunoassay. The immunoassay is based on competition of $^{125}$I-labelled MIAPaCa CSF-1 for "Rabbit 52" polyclonal antiserum raised against purified human urinary CSF-1.

One of the selected CV-1 clones from transfection with pcCSF-17 showed 2335 U/ml production of CSF-1, according to this assay, whereas cells not infected with SV40 slowed less than 20 U/ml. Controls using COS-7 cells transformed with 10 µg pcCSF-17 showed 2400 U/ml CSF-1 production without SV40 infection.

The CSF-1 producing CV-1 cell line contains the pcCSF-17, or analogous long form CSF-1 DNA or muteins thereof, stably integrated into its genome, and thus can be used for stable production of CSF-1 upon infection with SV40. Infection is presumed to "rescue" the pcCSF-17, or long form CSF-1 DNA, from the genome, and provide the SV40 T-antigen necessary for replication of the rescued DNA. Without SV40 infection, the integrated pcCSF-17, or long form CSF-1 DNA, is not effectively expressed.

Optimization of the expression of the CSF-1 encoding sequence by the CV-1 (CSF-17) cell line showed 6500–8000 U/ml when measured by the radioimmunoassay six days after SV40 infection using a multiplicity of infection of at least 1, and a 10% FBS medium. Studies on expression levels at a multiplicity of 10 showed comparable production, but production was reduced upon removal of the FBS from the medium on the second day after infection.

In the alternative, appropriate control systems and host vectors permitting expression in other eucaryotic hosts may be used to receive the CSF-1 encoding inserts. For example, CHO cells and suitable vectors may be used, as described in U.S. Ser. No. 438,991, filed Nov. 1, 1982, assigned to the same assignee and incorporated herein by reference. (U.S. Ser. No. 438,991 is now abandoned, however, a CIP issued Oct. 30, 1990 as U.S. Pat. No. 4,966,843.) In addition, baculovirus vectors containing these sequences are transformed into insect cells for production of protein as described in (89).

J.3. procaryotic Expression of CSF-1

For procaryotic expression as a mature protein, the cDNA clone, or the genomic sequence with introns excised by, for example, site-specific mutagenesis, is altered to place an ATG start codon immediately upstream of the glutamic acid at the N-terminus, and a HindIII site immediately upstream of the ATG in order to provide a convenient site for insertion into the standard host expression vectors below. This was done directly using insertion site-specific mutagenesis with a synthetic oligomer containing a new sequence complementary to the desired AAGCTTATG, flanked by nucleotide sequences complementary to the native leader and N-terminal coding sequences.

The DNA fragment containing the entire coding sequence was excised from pcCSF-17, or from pcDBhuCSF-4, by digestion with EcoRI, isolated by agarose gel electrophoresis, and recovered by electroelution. To carry out the mutagenesis, the host bacteriophage M13mp18 DNA was also treated with EcoRI and ligated with the purified fragment under standard conditions and transfected into frozen competent E. coli K12 strain DG98. The cells were plated on media containing $5\times10^{-4}$M isopropyl thiogalactoside (IPTG) obtained from Sigma Chem. (St. Louis, Mo.) and 40 µg/ml X-gal. Noncomplementing white plaques were picked into fresh media. Mini-cultures were screened for recombinant single strand phage DNA of the expected size, and the structure of the desired recombinant phage was confused using restriction analysis.

A 34-mer complementary to the N-terminal and leader encoding portions of the CSF-1 sequence, but containing the complement to the desired AAGCTTATG sequence was synthesized and purified. In the alternative, when negative sense strand M13 was used, the positive sense 34-mer was employed. A portion of this 34-mer preparation to be later used as probe was radiolabelled according to a modification of the technique of Maxam and Gilbert (87) as set forth above.

To perform the mutagenesis the above prepared recombinant bacteriophage was prepared in E. coli K12 strain DG98 and the single strand phage DNA purified. One pmol of single strand phage DNA and 10 pmol of the above synthetic nucleotide primer (not kinased) was annealed by heating for 1 minute at 67° C., and then 30 minutes at 37° C. in 15 µl 20 mM Tris-Cl, pH 8, 20 mM MgCl$_2$, 100 mM NaCl, 20 mM 2-mercaptoethanol. The annealed DNA was incubated with DNA polymerase I (Klenow) and 500 µmol dNTPs for 30 minutes, 0° C. and then brought to 37° C. Aliquots (0.05 or 0.25 pmol) were removed after 5 minutes, 20 minutes, and 45 minutes, transformed into E. coli K12 strain DG98 and plated.

After growth, the plates were chilled at 4° C. and plaques lifted with PalI membranes obtained from Biodyne or S&S filters (1–2 minutes in the first filter, more than 10 minutes for the second filter. The filters are denatured in 2.5M NaCl, 0.5M NaOH (5 min). The denaturing medium is neutralized with 3M sodium acetate to pH 5.5 or with 1M Tris-Cl, pH 7.5 containing 1M NaCl, the filters baked at 80° C. in vacuo for 1 hour, and then prehybridized at high stringency. The filters are then probed with the kinased synthetic 34-mer prepared above at high stringency, washed, and autoradiographed overnight at −70° C. and autoradiographed overnight at −70° C.

The RF form of each desired mutated phage was treated with EcoRI, blunted with Klenow, and then digested with HindIII to excise the gene as a HindIII/blunt fragment.

The plasmid pFC54.t (ATCC No. 39789), which contains the P$_L$ promoter and the Bacillis thuringiensis positive retroregulatory sequence (as described in EP No. 717,331, published 29 Mar. 1985), was used as a host vector. pFC54.t was digested with HindIII/BamHI (blunt), and the desired coding sequences were ligated into the vector using the HindIII/EcoRI (blunt) excised fragment from the mutated M13 derived from pcCSF-17 or pcDBhuCSF-4. After transformation into $E.\ coli$ MC1000 λ lysogen, and induction, CSF-1 production, putatively of SCSF and LCSF, respectively, was obtained and verified as described above.

Thus, for example, the HindIII/EcoRI blunt fragment from the M13 substrate mutated from pcCSF-17 was ligated into pFC54.t as described above to obtain $pP_LCSF$-17. $pP_LCSF$-17 was then digested with BamHI and religated to obtain $pP_LCSF$-17/C∇158, which contains the coding sequence for mature SCSF preceded by an ATG start codon, and truncated so as to encode a protein having the first 158 amino acids of the SCSF sequence, followed by an in-reading-frame proline and stop codon from the retroregulatory sequence of pFC54.t. $pP_LCSF$-17/C∇158 was further modified by site-specific mutagenesis. The HindIII/BamHI coding sequence was excised and ligated into M13. An appropriate primer was used to place a stop codon immediately after the codon encoding amino acid 158, and to follow it by TGA. This creates a BamHI/BclI site for further manipulation. The mutated fragment was then excised from M13 and religated into HindIII/BamHI-digested pPLCSF-17/C∇158 to obtain $pP_LCSF$-17/C∇158TGA.

Other constructs having codons for substitute amino acids include modifications replacing lys at position 52 by gln or pro and/or tyr at 59 by asp in SCSF. These constructs were made analogously by site-directed mutagenesis of M13 inserts containing the HindIII/EcoRI (blunt) fragment from the original $pP_LCSF$-17. HindIII/EcoRI fragments from these mutated phages are then used in place of the original HindIII/EcoRI insert in construction of corresponding vectors. In general, desired mutations in selected locations can be made according to variations of this standard technique.

It is possible to improve the level of CSF-1 production from any of the foregoing constructs by altering the third nucleotide in each of the first six codons of the N-terminus. pFC54.t containing the CSF-1-encoding fragment of any mutein is digested with HindIII/BstXI, and the excised fragment (which contains the ATG and a short portion of the subsequent coding sequence) is replaced by a synthetic HindIII/BstXI segment wherein the first six codons have the sequence: (SEQ ID NO: 19). The resulting analogous expression vector represents no change in the amino acid sequence encoded; however, the levels of expression were improved when this modified vector was used. The corresponding vectors are prefixed by O/E (over-expression). Thus, for example, O/E $pP_LCSF$-17, O/E $pP_LCSF$-17/C∇158, and O/E $pP_LCSF$-17/C∇158TGA are formed.

The corresponding vector, O/E $pP_LCSF$-17asp$_{59}$/C∇158TGA was synthesized as described above except that the M13 containing the original EcoRI insert was doubly mutated to place a HindIII site and ATG start codon immediately before amino acid 1 of the mature protein, and to replace the tyrosine codon at residue 59 by a codon representing aspartic acid. The corresponding vectors OE $pP_LCSF$-17asp$_{59}$/C∇158, and O/E $pp_LCSF$-17asp$_{59}$/C∇158TGA are thus correspondingly formed. In all of the foregoing cases, each of the intermediate vectors can be digested with HindIII and BstXI and the synthetic DNA fragment containing preferred codons substituted for the native sequence encoding the first six amino acids.

In addition, all of the foregoing vectors are modified to encode proteins with N-terminal deletions by substitution of the appropriate synthetic fragment for the excised HindIII/BstXI DNA. In this manner, the corresponding vectors encoding CSF/N∇2 and N∇3, lacking glu-glu and glu-glu-val were constructed.

Analogous vectors were also constructed containing a termination codon immediately after the glycine residue at position 150 of the SCSF protein. These vectors were obtained by mutagenesis of the HindIII/EcoRI fragment from $pP_LCSF$-17 or $pP_LCSF$-17asp$_{59}$ or their corresponding muteins into HindIII/SmaI-digested M13. The resulting vectors, for example, $pP_LCSF$-17/C∇150 and $pP_LCSF$-17asp$_{59}$/C∇150 encode, therefore, the first 150 amino acid residues of the mature SCSF protein.

The foregoing vectors when transformed into $E.\ coli$ λ lysogen host, such as DG116, and induced at high temperature (approximately 42° C.) produce CSF-1 and muteins thereof in monomeric or aggregated deglycosylated form. The production of this protein can be detected by the use of standard radioimmunoassay or other CSF-1 specific assays. The activity of the protein can be measurably improved by the use of refolding procedures described and claimed in U.S. Ser. No. 040,174, filed on Apr. 16, 1987, assigned to the same assignee, and incorporated herein by reference.

Constructs have also been made using the phosphatase A promoter and secretory leader sequence in place of the $P_L$ promoter. These regulatory signals are derived from pSYC1089,which is extensively described and claimed in U.S. Ser. No. 715,653, filed 25 Mar. 1985, assigned to the same assignee and incorporated herein by reference. (U.S. Ser. No. 715,653 is now abandoned, but see EP No. 196,864 which published Oct. 8, 1986.) The control sequences, including the 3' retroregulatory sequences corresponding to those in pFC54.t are provided by inserting the desired coding sequence into NarI/BamHI digested pSYC1089, a host vector which contains these controls.

In order to utilize this vector, the relevant CSF-encoding sequences are religated into M13 to change the HindIII site immediately preceding the ATG to a ClaI site. The mutated sequence is then excised as a ClaI/BclII fragment and ligated into the digested pSYC1089 vector as described. The products of this construct, corresponding to the short forms produced under the control of the $P_L$ promoter in the $P_L$ vector series are secreted into the piroplasmic space when expressed in $E.\ coli$ and are relatively soluble as compared to products of genes expressed under $P_L$ control. Vectors which can be constructed using the phoA system here described include pPhoA-LCSF/C∇158 and pPhoA/N∇3C∇150. These vectors are transformed for expression into a non-λ lysogen host, such as $E.\ coli$ MM294.

Vectors were also constructed using DNA derived from the long form clone. O/E $pP_LCSF$-17asp$_5$/C∇150; described above, was used as the host vector for constructs of the long form and of various C-terminal truncations in the coding sequence for the long form. Because the sequences upstream from the BstXI site are common to both the short and long forms, vectors containing the short form and its muteins can be converted to long form vectors by interchanging the BstXI to BamHI fragment of this vector, which excises the downstream portions of the sequence through and including the TGA stop codon with the BstXI to BamHI fragment of M13 containing the long-form coding sequence from clone 4, or its C-terminal truncations.

Accordingly, the M13 clone containing the clone 4 insert was mutagenized with appropriate oligomers to insert stop codons after the residues at positions after 150, 190, 191, 221,223,236, 238, 249, 258, and 411. For example, the reverse strand M13 containing the clone 4 insert was primed with the oligonucleotide (SEQ ID NO: 18) in order to place a stop codon after the threonine residue at position 191 and provide a unique BclI site immediately thereafter. The mutagenized RF form of the phage was digested with BstXI and BamHI and ligated into BstXI/BamHI-digested O/E pP$_L$CSF-17asp$_{59}$/C∇150 to give O/E pP$_L$LCSFasp$_{59}$/C∇150.

The mutated long form can be used to replace the corresponding short form fragments from vectors encoding CSF-1 proteins with N-terminal deletions, as well as from the corresponding constructions in the phoA-controlled vectors. For example, pPhoA-LCSF/N▽3C▽221 and pPhoA-LCSF/C▽221 were constructed and transformed into *E. coli* MM294. Of course, more than one mutation of the long form can be effected; also, amino acid substitutions, such as $gly_{52}$ or $tyr_{95}$, can be made.

Additional constructs have been made for muteins encoding SCSF, LCSF and their muteins wherein the glycosylation sites at positions 122–124 and 140–142, common to both proteins have been replaced with amino acids not subject to glycosylation. The CSF proteins produced from bacterial expression of these constructions are active in biological assays; this substantiates the proposition that glycosylation is not necessary for activity. However, replacement of any of the cysteine residues between positions 1–150 by serine or alanine results in inactive proteins, except that muteins having a substitution at position 90 have activity. Evidently all seven of these cysteines are required, or at least desirable, for proper refolding.

Construction of N▽2 and N▽3 muteins of the invention from any of the above vectors is extremely straightforward, and simply involves deleting the HindIII/BstXI fragment and replacing it with a synthetic fragment which does not include the codons for the first two or three amino acids, as the case may be. Thus, each of the foregoing vectors can be modified to obtain a vector encoding the muteins of the invention by this simple substitution procedure.

Included in the recombinant organisms prepared are *E. coli* DG116 λ lysogen transformed with the following plasmids, which are constructs for the expression of the indicated short form-derived CSF-1 mutein forms:

| Construct | Encoded Protein |
|---|---|
| $pP_LCSF$-17 | SCSF |
| $pP_LCSF$-17$gln_{52}$ | $gln_{52}$SCSF |
| $pP_LCSF$-17$pro_{52}$ | $pro_{52}$SCSF |
| $pP_LCSF$-17/C▽158 | SCSF/C▽159-pro |
| $pP_LCSF$-17$gln_{52}$/C▽158 | $gln_{52}$SCSF/C▽158-pro |
| $pP_LCSF$-17$pro_{52}$/C▽158 | $pro_{52}$SCSF/C▽158-pro |
| $pP_LCSF$-17$asp_{59}$ | $asp_{59}$SCSF |
| $pP_LCSF$-17/C▽158TGA | SCSF/C▽158 |
| O/E $pP_LCSF$-17/C▽158TGA | SCSF/C▽158 |
| $pP_LCSF$-17$pro_{52}$/C▽158TGA | $pro_{52}$SCSF/C▽158 |
| $pP_LCSF$-17$asp_{59}$/C▽158TGA | $asp_{59}$SCSF/C▽158 |
| O/E $pP_LCSF$-17$asp_{59}$/C▽158TGA | $asp_{59}$SCSF/C▽158 |
| $pP_LCSF$-17/C▽150 | SCSF/C▽150 |
| O/E $pP_LCSF$-17/C▽150 | SCSF/C▽150 |
| $pP_LCSF$-17$asp_{59}$/C▽150 | $asp_{59}$SCSF/C▽150 |
| O/E $pP_LCSF$-17$asp_{59}$/C▽150 | $asp_{59}$SCSF/C▽150 |
| O/E $pP_LCSF$-17$asp_{59}$/N▽2C▽150 | $asp_{59}$SCSF/N▽2C▽150 |
| O/E $pP_LCSF$-17$asp_{59}$/N▽3C▽150 | $asp_{59}$SCSF/N▽3C▽150 |

The following analogous recombinant organisms encoding variations of the long form are constructed:

| | |
|---|---|
| O/E $pP_LLCSF$/C▽150 | LCSF/C▽1/C▽150 |
| O/E $pP_LLCSFgln_{52}$/C▽150 | $gln_{52}$LCSF/C▽150 |
| O/E $pP_LLCSFtyr_{59}$/C▽190 | $tyr_{59}$LCSF/C▽190 |
| O/E $pP_LLCSF$/C▽191 | LCSF/C▽191 |
| O/E $pP_LLCSF$/N▽2C▽191 | LCSF/N▽2C▽190 |
| O/E $pP_LLCSF$/C▽221 | LCSF/C▽221 |
| O/E $pP_LLCSF$/N▽3C▽221 | LCSF/N▽3C▽221 |
| O/E $pP_LLCSF$/C▽223 | LCSF/C▽223 |
| O/E $pP_LLCSF$/C▽236 | LCSF/C▽236 |
| O/E $pP_LLCSF$/C▽238 | LCSF/C▽238 |
| O/E $pP_LLCSF$/C▽249 | LCSF/C▽249 |
| O/E $pP_LLCSF$/C▽250 | LCSF/C▽250 |
| O/E $pP_LLCSF$/C▽411 | LCSF/C▽411 |
| phoA-LCSF/C▽221 | LCSF/C▽221 |
| phoA-LCSF/N▽3C▽221 | LCSF/N▽3C▽221 |
| O/E phoA-LCSF/C▽221 | LCSF/C▽221 |
| O/E phoA-LCSF/N▽3C▽221 | LCSF/N▽3C▽221 |

For expression of the constructions, suitably transformed *E. coli* (λ lysogen, e.g., DG116 for the $P_L$ constructs, non-lysogen, e.g., MM294 for PhoA) are grown to the desired cell density and then production of the encoded protein induced. If expressed under control of the $P_L$ promoter, an increase in temperature to 37° C. or 42° C. induces expression. The addition of about 0.5–2% casamino acids to the medium is also helpful in increasing expression. The constructs described above result in the formation of CSF-1 as an insoluble intracellular protein which can be recovered from the lysed cells, purified and refolded according to the procedures set forth in U.S. Ser. No. 040,174 (supra) and described below. Similar procedures can be used to puffy and refold the CSF-1 secreted to the periplasmic space of *E. coli* transformed with the phoA-controlled genes.

In general, the refolding begins with the solubilized monomer in a chaotropic environment, which is maintained under reducing conditions. Such maintenance may involve the use of a suitable reducing agent such as β-mercaptoethanol or dithiothreitol (DTT) but the CSF-1 may already be reduced, and exclusion of oxidizing agents may be sufficient. The solubilized protein is typically maintained in, for example, 8M tires or 7M guanidinium hydrochloride, at a pH of about 7–8.5, in the presence of about 25–100 mM thiol compound. Starting with this solubilized form, the monomer may either be refolded directly or purified from remaining proteins by a suitable purification procedure such as chromatography on an adsorbent gel or gel-permeation chromatography prior to refolding. Gel-permeation chromatography is preferred, as it permits an easy size separation of the desired monomer length, which is generally known in advance, from impurities of differing molecular weights. It is required that the purification be conducted under reducing conditions in order to prevent the formation of disulfide-linked aggregates. Thus, regardless of the chromatographic procedure used, a suitable reducing agent is preferably included in the solutions used to load the chromatographic columns or batches and in the eluting solutions. In some instances, low pH may be substituted for reducing agent, as low pH will prevent disulfide bond formation in some chromatographic systems, even in the absence of reducing agent.

The partially purified monomer is then subjected to refolding conditions for the formation of the dimer. The protein concentration during this step is of considerable importance. Generally, yields are increased if the protein concentration is less than 2 mg/ml of the CSF-1 protein (we have refolded at 0.7 mg/ml and 1 mg/ml with good results). The refolding conditions may include gradual removal of the chaotropic environment over an appropriate time period, usually several hours. One easy method is dilution of the sample to the desired concentration of the chaotropic agent, but this may not in certain instances be preferred, since the protein also becomes diluted. More preferred are methods which provide a constant protein concentration, such as dialysis or hollow fiber diafiltration. At the end of the process, when the chaotropic environment is depleted, a nondenaturing level is reached. For example, if guanidine hydrochloride is used as chaotropic agent, a final concentration of less than about 2M, and preferably 0.5–1M is attained.

The refolding during removal of chaotropic environment is conducted in a manner so as to permit oxidation of the sulfhydryl groups to disulfides in order to establish the resultant biologically active dimeric configuration which, in the case of CSF-1 is stabilized by the formation of disulfides, one or more of which may link the two chains. Intrachain disulfides are also formed. Suitable redox conditions which encourage this formation of dimer include the SH/disulfide reagent combinations, such as oxidized and reduced glutathione. The ratio of reduced to oxidized glutathione or other sulfhydryl/disulfide combination is typically from about 2 mM/0.1 mM to 0.5 mM/1.0 mM. Alternative methods for providing this oxidation are also acceptable. Simple removal of the reducing agent without precautions to exclude air and metal ions may suffice to effect formation of some correct disulfide linkages, but this is less preferred. In any event, the pH of the solution during the refolding process should be maintained at about pH 7.5–9.0. It is clear that in the process of refolding, the reducing conditions under which the initial purification was conducted are no longer employed.

During the refolding process, aggregates of the monomer, which are insoluble, may form. This is minimized through temperature control, wherein low temperatures of about 0.4° C. are preferable to higher temperatures of 25°–37° C. After refolding is completed, the dimer is purified from other proteins using standard procedures.

When constructs encoding the N-terminal depleted muteins are expressed in *E. coli*, as mentioned above, the methionine at the N-terminus is processed more efficiently than is the case for the corresponding mature sequences. Specifically, expression of $pP_LCSF-17/C\nabla150$ results in protein wherein most, if not all of the sequenceable molecules contain N-terminal methionine; corresponding expression of $pP_LCSF-17/N\nabla2C\nabla150$ results in protein wherein only 78% of the molecules retain the N-terminal methionine. Expression of $pP_LCSF-17/N\nabla3C\nabla150$ gives protein wherein less than or equal to about 5% of the product contains methionine at the N-terminus.

Figure 3:
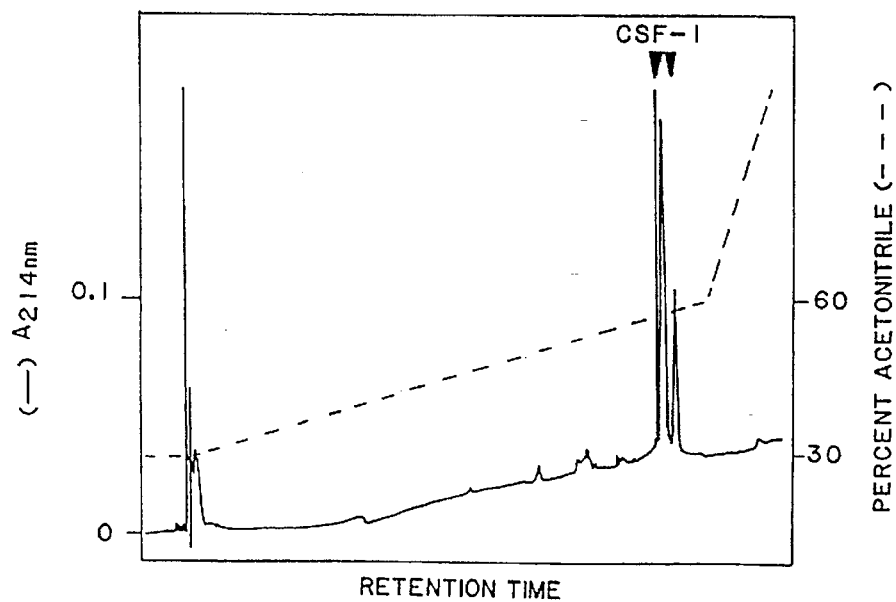
FIG. 3 shows RP-HPLC of recombinant CSF-1 produced in E. coli from a gene encoding asp$_{59}$ SCSF/C$\nabla$150.
Figure 5:
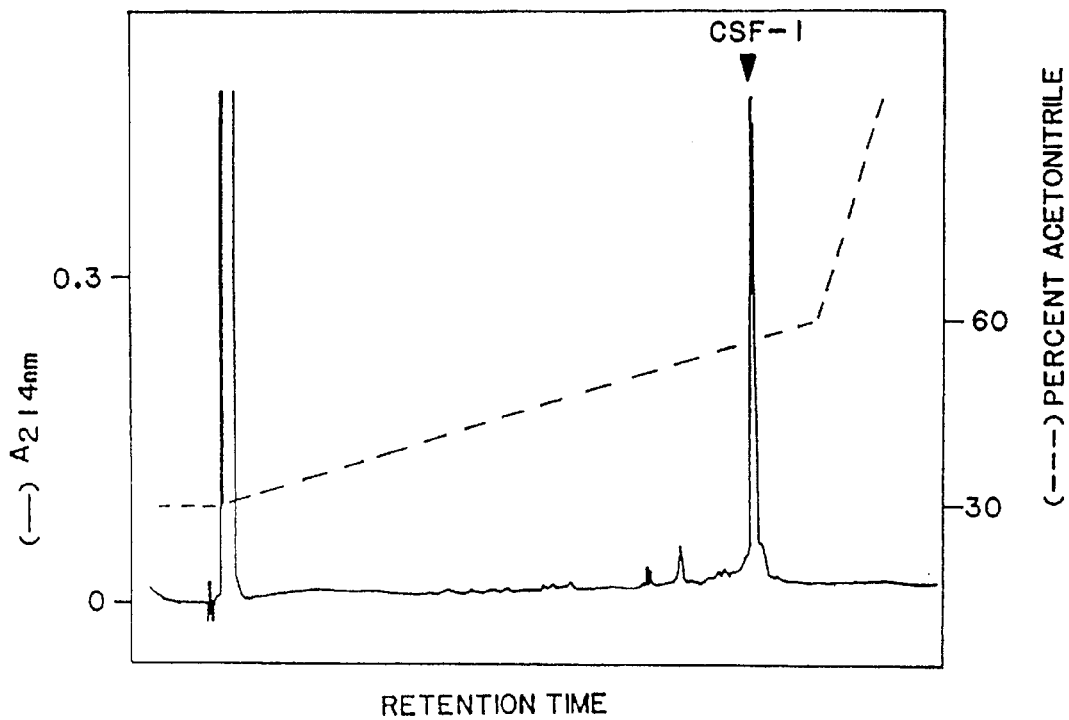
FIG. 5 shows RP-HPLC analysis of the corresponding N-terminal deleted form, asp$_{59}$ SCSF/N$\nabla$3C$\nabla$150.
Figure 4:
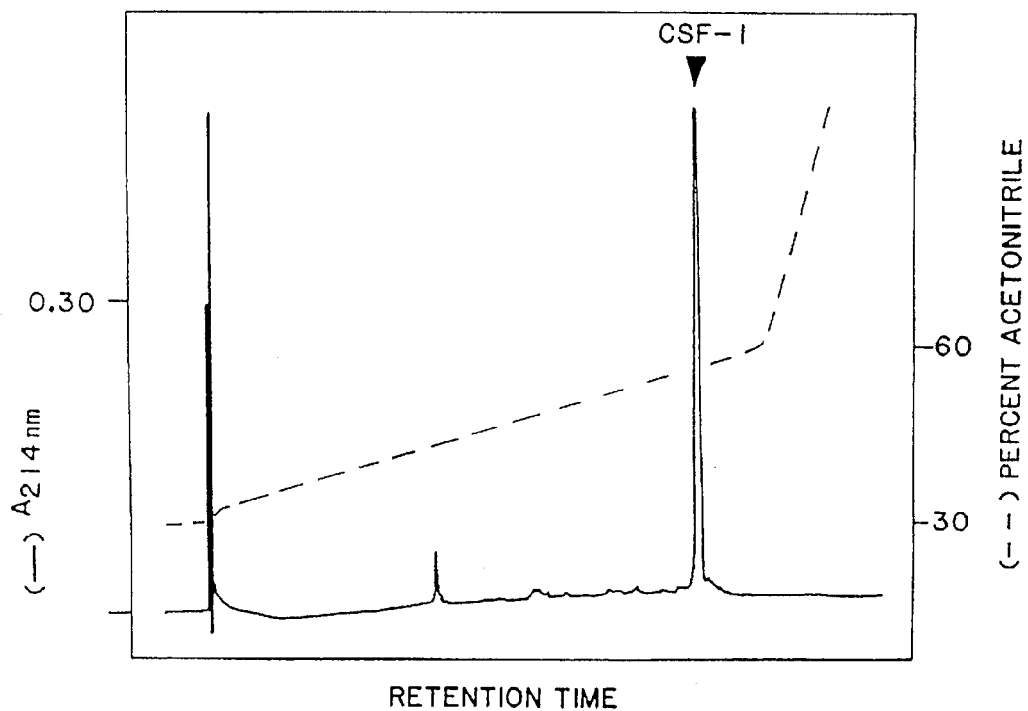
FIG. 4 shows RP-HPLC analysis of the corresponding N-terminal deleted form, asp$_{59}$-SCSF/N$\nabla$2C$\nabla$150.

FIGS. 4–5 show the effect of N-terminal deletions on resulting protein heterogeneity. FIGS. 2 and 5 show the RP-HPLC analyses of purified CSF-1 expressed in *E. coli* using $pP_LCSP-17/C\nabla158$ ($tyr_{59}$) and $pP_LCSF-17/C\nabla150$ ($asp_{59}$), respectively. As shown in both figures, there are two major peaks at approximately 18 kd in the reducing conditions under which these analyses were run. The leading peak, labelled 18 K-A in FIG. 2 (and the corresponding peak in FIG. 3) comprises approximately 70% of the total of the 18 kd protein, and has essentially the same amino acid composition and SDS-PAGE subunit molecular weight as the trailing peak (labelled 18 K-B). In addition, the 158 codon construct results in a major impurity in the form of a 15 kd protein, which is evidently the product of an internal restart. This peak seems to be missing from the product of the 150 codon ($asp_{59}$) construct, shown in FIG. 3.

The results in FIG. 3 should properly be compared with those of FIGS. 4 and 5, which represent RP-HPLC analysis from the expression of $pP_LCSF-17/N\nabla2C\nabla150$ and $pP_LCSF-17/N\nabla3C\nabla150$. In both cases, the significant heterogeneity seen on RP-HPLC has disappeared, and a single peak corresponding to the leading 70% peak of FIG. 3 is obtained.

K. Preparation of Murine CSF-1 cDNA

An intronless DNA sequence encoding murine CSF-1 was prepared using a murine fibroblast cell line which produces large amounts of CSF-1. The L-929 line, obtainable from ATCC, was used as a source for mRNA in order to produce a cDNA library. Two clones encoding the "long form" of CSF-1 were recovered using the human "short form" cDNA as probe. Murine CSF-1 is believed to be approximately 80% homologous to the human material because of the homology of the N-terminal sequences, the ability of both human and murine CSF-1 preparations to stimulate macrophage colonies from bone marrow cells, and limited cross-reactivity with respect to radioreceptor and radioimmunoassays (5).

The recovered cDNA was sequenced and found to encode a long form of CSF-1; analogy to the human sequence provided information which permitted construction of a probe for human CSF-1 containing the extra 894 bp sequence described above, based on the 5' end of the 6th exon.

The murine CSF-1 protein is particularly useful in model systems to elucidate the activity profile of CSF-1.

K.1. Use of CSF-17 Probe

Total messenger RNA was extracted and purified from murine L-929 cells. Murine 1–929 cells were cultured for 8 days on DME medium an then harvested by centrifugation. Total cytoplasmic messenger RNA was isolated from the cells by the same protocol as set forth above for MIAPaCa mRNA.

The total mRNA preparation was run on sucrose gradients, as described in PCT No. WO86/04607 (supra), in connection with the preparation of mRNA from MIAPaCa cells, except that a 5–25% sucrose gradient was used in place of the 5–20% gradient there set forth.

Aliquots from each fraction in the gradient were injected into *Xenopus laevis* oocytes and the products were assayed by radioimmunoassay against anti-CSF-1 antibodies prepared according to (5). There were two mRNA peaks at fractions 17–20 and at 23–26 which showed translated product immunoreactive with CSF-1.

Fractions 19–20 and 24–25 were pooled and used to construct a cDNA library in λgt10, as described in (82). Before insertion, the crude cDNA preparation was ligated to EcoRI linkers, digested with EcoRI, and the double-stranded cDNA electrophoresed on a 5% acrylamide gel. Only DNA containing more than 800 bp was eluted, then ligated with the λgt10 arms, and packaged using Vector Cloning Systems (Strategene) Gigapak.

Approximately 1 million phage plaques were probed with a $_{32}$P-labelled single-stranded CSF-17 DNA prepared as described in connection with the isolation of the long form human CSF-1 above.

A number of phage plaques which hybridized to probe were purified, and two clones, one with a 2 kb insert and the other with a 4 kb insert, were selected for further study. Restriction mapping showed these clones to have a large region in common, and both clones were subcloned into M13mp18 and M! 3mp19 for dideoxy sequencing; the clones were sequenced on both strands. The nucleotide sequences for both clones and the deduced amino acid sequence encoded by them are shown in (SEQ ID NO: 21) and (SEQ ID 23).

(SEQ ID NO: 21) and (SEQ ID NO: 22), respectively show the cDNA and deduced amino acid sequence for a murine 4 kb clone encoding muCSF-1. As shown in (SEQ ID NO: 22), the longer, 4 kb clone begins at nucleotide 24 relative to the human CSF-17 shown in (SEQ ID NO: 3) and has 159 bp untranslated 5' sequence, followed by 96 bp of DNA encoding the leader. The coding sequence for the mature protein begins at nucleotide 256 of this clone and continues for another 1560 nucleotides, thus encoding a 520 amino acid protein. There is considerable sequence homology with the human "long form" CSF-1-encoding sequence. After the stop codon at nucleotide 1816, however, the nucleotide sequence diverges widely from the human 3' untranslated sequence in pcCSF-17 and in the "long form" clones.

The shorter 2 kb clone has approximately 500 bp of 3' untranslated sequence, which is considerably more homologous to the 3' untranslated sequence found in CSF-17. The DNA sequence for the shorter, 2 kb clone is shown in (SEQ ID NO: 22). (SEQ ID NO: 22) shows the cDNA and deduced amino acid sequence for a murine cDNA 2 kb clone encoding a similar muCSF-1. This is 90 bp shorter at the 5' end, but contains the same coding sequence as the 4 kb clone except for 2 nucleotide changes, both resulting in changes in amino acid sequence. The relevant positions are 1034 in the longer (944 in the shorter) clone, and 1192 in the longer (1102 in the shorter) clone. The G in position 944 of the shorter clone results in a gly at position 259 of the mature protein; the corresponding A of the longer clone results in Asp in this position. The second change, from T in the longer to C in the shorter clone, results in a change from serine at position 312 to proline in the shorter clone.

Thus, as shown in (SEQ ID NO: 22) and (SEQ ID NO: 24), the murine CSF protein (SEQ ID NO: 2), is roughly homologous to the long form of the human protein, and apparently contains a 296 amino acid segment corresponding to the "extra" peptide sequence "inserted into" the peptide encoded by CSF-17 DNA.

The longer and shorter clones encoding murine CSF-1, described above and in (SEQ ID NO: 22) and (SEQ ID NO: 24), respectively and FIG. 2, were excised from λgt10 by EcoRI digestion and cloned into the modified Okayama-JBerg cloning vector pcDB, thus placing them under the control of the SV40 early promoter, and to obtain pcDBmuCSF-L and pcDBmuCSF-S, respectively.

K.2. Mutein Forms

In a manner precisely similar to that described above in connection with the human sequence mutated forms of the murine sequence are now available by virtue of the isolated DNA. In particular, the $tyr_{59}$ and $gln_{52}$ and $tyr_{59}gln_{52}$ forms may be obtained by modifying the DNA inserts of pcDBmuCSF-L and pcDBmuCSF-S in a manner precisely similar to that described for pcCSF-17 above. The modified vectors then encode the mutein forms of the protein designated $asp_{59}$-muLCSF, $gln_{52}$-muLCSF, and $tyr_{59}gln_{52}$-muLCSF, respectively.

K.3. Expression of Murine CSF-1 DNA

The expression vectors pcDBmuCSF-L and pcDBmuCSF-S were transfected into COS-A2 cells using DEAE dextran with the addition of chloroquine, as described above.

The supernatants were collected after 72 hours and tested for CSF-1 activity using the use bone marrow proliferation assay described above. The supernatants both contained CSF-1 activity, according to this assay, as shown by the results in Table 6.

TABLE 6

| Expression of pcDBmuCSF-L and pcDBmuCSF-S in COS-A2 Cells | |
|---|---|
| Sample | BM Assay (Units/ml) |
| (2 kb mouse clone) pcDBmuCSF-S | 11,533 |
| (4 kb mouse clone) pcDBmuCSF-L | 5,033 |

In a similar manner, the mutein forms of the murine sequence are obtained.

L. Formulation of CSF-1

The recombinantly produced human CSF-1 short or long form may be formulated for administration using standard pharmaceutical procedures. Ordinarily CSF-1 will be prepared in injectable form, and may be used either as the sole active ingredient, or in combination with other proteins or other compounds having complementary or similar activity. Such other compounds may include alternative antitumor agents such as adriamycin, or lymphokines, such as IL-1, IL-2, and IL-3, α-, β-, and γ-interferons and tumor necrosis factor. The effect of the CSF-1 active ingredient may be augmented or improved by the presence of such additional components. As described above, the CSF-1 may interact in beneficial ways with appropriate blood cells, and the compositions of the invention therefore include incubation mixtures of such cells with CSF-1, optionally in the presence of additional lymphokines. Either the supernatant fractions of such incubation mixtures, or the entire mixture containing the cells as well may be used.

M. Deposits

On Apr. 2, 1985, Applicants deposited with the American Type Culture Collection, Rockville, Md., USA (ATCC) the phage phCSF-1 in *E. coli* DG98, Accession No. 40177. On May 21, 1985, phCSF-1, designated CMCC 2312 in the Cetus collection and phCSF-1a λ Charon 4A for deposit, was deposited with ATCC and has Accession No. 40185. On Jun. 14, 1985, pcCSF-17 in *E. coli* MM294, designated CMCC 2347, was deposited with ATCC and has Accession No. 53149. In addition, pcDBCSF4, designated herein pcdBhuCSF-4 (CMCC 2894), was deposited with ATCC on Oct. 24, 1986, and has ATCC Accession No. 67250. On Apr. 7, 1987, pP$_L$CSF-17asp$_{59}$/CV150 in DG116 (CMCC 2946) was deposited at ATCC and has Accession No. 67,383. The murine sequence plasmids pcDBmuCSF53 and pcDBmuCSF10, designated herein pcDBmuCSF-S and pcDBmuCSF-L respectively, were deposited at ATCC on this date also and have CMCC Nos. 2892 and 2893, and ATCC Accession Nos. 67248 and 67249.

Additional deposits have been made on Apr. 14 1987, as follows:

| Strain | CMCC No. | ATCC No. |
|---|---|---|
| pPhoA-LCSF/C∇221 in MM94 | 3084 | 67391 |
| O/E pP$_L$LCSF/N∇221 in DG116 | 3095 | 67390 |
| O/E pP$_L$CSF-17asp$_{59}$/C∇150 in DG116 | 3044 | 67389 |
| pP$_L$CSF-17asp$_{59}$/C∇150 in DG116 | 2946 | 67383 |

These deposits were made under the provisions of the Budapest Treaty on the International recognition of the Deposit of Microorganisms for the Purposes of Patent Procedure and the Regulations thereunder (Budapest Treaty). This assures maintenance of a viable culture for 30 years from the date of deposit. The deposits will be made available by ATCC under the terms of the Budapest Treaty, and subject to an agreement between Applicants and ATCC which assures permanent and unrestricted availability upon issuance of the pertinent U.S. patent. The Assignee herein agrees that if the culture on deposit die or be lost or destroyed when cultivated under suitable conditions, it will be promptly replaced upon notification with a viable specimen of the same culture. Availability of the deposits is not to be construed as a license to practice the invention in contravention of the rights granted under the authority of any government in accordance with its patent laws.

These deposits were made for the convenience of the relevant public and do not constitute an admission that a written description would not be sufficient to permit practice of the invention or an intention to limit the invention to these specific constructs. Set forth hereinabove is a complete written description enabling a practitioner of ordinary skill to duplicate the constructs deposited and to construct alternative forms of DNA, or organisms containing it, which permit practice of the invention as claimed.

The scope of the invention is not to be construed as limited by the illustrative embodiments set forth herein, but is to be determined in accordance with the appended claims.

Bibliography

1. Dexter T. M., *Nature* (1984) 309:746
2. Vadas, M. A., et al., *J Immunol* (1983) 130:793
3. Metcalf, D. *Science* (1985) 229:16–22
4. Clark, S. C. et al, *Science* (1987) 236:1229–1237
5. Das, S. K., et al., *Blood* (1981) 58:630
6. Stanley, E. R., et al., *J Biol Chem* (1977) 252:4305
7. Waheed, A., et al., *Blood* (1982) 60:238
8. Ben-Avram, C. M., et al., *PNAS (USA)* (1985) 882:4486
9. Das, S. K., et al., *J Biol Chem* (1982) 257:13679
10. Wang, F. F., et al., *J Cell Biochem* (1983) 21:263
11. Waheed, A. et al., *Exp Hemat* (1984) 12:434
12. Wu, M., et al., *J. Biol Chem* (1979) 254:6226
13. Fojo, S. S., et al, *Biochemistry* (1978) 17:3109
14. Burgess, A. W., et al, *J Biol Chem* (1977) .252:1998
15. Lusis, A. J., et al., *Blood* (1981) 57:13
16. U.S. Pat. No. 4,601,978
17. Wu, M., et al, et al., *Biochemistry.* (1980)19:3846
18. Cough, et al., *Nature* (1984) 309:763–76
19. Fung, M. C., et al., *Nature* (1984) 307:233
20. Yang et al., *Cell* 47:3–10 (1986)
21. Dorssers et al., *Gene* (1987)
22. Yokota et al., *PNAS* 81:1070–1074 (1984)
23. Wong el al., *Science* 228:810–815 (1985)
24. Lee et al. *PNAS* 82:4360–4363 (1985)
25. Cantrell el al., *PNAS* 82:6250–6256 (1985)
26. Kawasaki, E. S., et al., *Science* (1985) 230:292–296
27. Wong, G. G., et al., *Science* (1987) 235:1504–1509
28. Ladher, M. D., et al *EMBO J* (1987) 6:2693–2698
29. Metcalf, D., *J Cell Physiol* (1970) 76:89
30. Moore, R., et al., *Science* (1984) 223:178
31. Stanley, E. R., *The Lymphokines* (1981), Stewart, W. E., II, et al., ed, Humana Press, Clifton, N.J., pp. 102–132
32. Byrne, P. V., et al., *Cell Biol* (1981) 91:848
33. Fieit, H. B., et al., *J Cell Physiol* 108:347 (1981)
34. Wing, E. J., et al. *J Clin Invest* 69:270 (1982)
35. Ralph, P., et al. *Cell Immunol* 76:10 (1983)
36. Nogawa, R. T., et al., *Cell Immunol* 53:116 (1980)
37. Bolivar, et al., *Gene* (1977) 2:95
38. Chang, et al., *Nature* (1977) 198:1056
39. Goeddel, et al., *Nucleic Acids Res* 8:4057 (1980)
40. Shimatake, et al., *Nature* (1981) 292:128
41. Broach, J. R., *Meth Enz* (1983) 101:307
42. Stinchcomb, et al., *Nature* (1979) 282:39
43. Tschempe, et al., *Gene* (1980) 10:157
44. Clarke, L., et al. *Meth Enz* (1983) 101:300
45. Hess, et al., *J Adv Enzyme Reg* (1968) 7:149
46. Holland, et al., *Biochemistry* (1978) 17:4900
47. Hitzeman, et al., *J Biol Chem* (1980) 255:2073
48. Holland, M. J., et al., *J Biol Chem* (1981) 256:1385
49. Broach, J., et al., *Gene* (1978) 8:121
50. Tissue Culture, Academic Press, Cruz and Patterson, editors (1973)
51. Fiers, et al., *Nature* (1978) 273:113
52. Depicker, A., el al., *J Mol Appl Gen* (1982) 1:561
53. Miller, D. W., el al., in *Genetic Engineering* (1986) Sefiow, J. K., et al., eds., Plenum Publishing, Vol. 8, pp. 277–297
54. Cohen, S. N., *Proc Natl Acad Sci (USA)* (1972) 69:2110
55. Shaw, C. H., et al., *Gene* (1983) 23:315
56. Graham et al. *Virology* (1978) 52:546
57. Van Solingen, P., et al., *J Bact* (1977) 130:946
58. Hsiao, C. L., et al., *Proc Natl Acad Sci (USA)* (1979) 76:3829
59. Maniatis, T., et al., *Molecular Cloning* (1982) Cold Spring Harbor Press, pp. 202–203)
60. Bailey, J. M., et al., *Anal Biochem* (1976) 70:75–85
61. Sehgal, P. B., et al., *Nature* (1980) 288:95–97
62. *Methods in Enzymology* (1980) 65:499–560
63. Matteucci, et al., (*J Am Chem Soc* (1981) 103:3185–3191
64. Clewell, D. B., et al., *Proc Natl Acad Sci (USA)* (1969) 62:1159
65. Clewell, D. B., *J Bacteriol* (1972) 110:667
66. Sanger et al. *PNAS (USA)* 74:5463 (1977)
67. Messing, et al., *Nucleic Acids Res* (1981) 9:309
68. Maxam, et al., *Methods in Enzymology* (1980) 65:499
69. Fieit, H. B., et al., *J Cell Physiol* (1981) 108:347
70. Ralph, et al., *Cell Immunol* (1987) 105:270–279
71. Wing, E. J., et al., *J Clin Invest* (1982) 69:270
72. Ralph, P. et al., *Cell Immunol* (1983) 76:10
73. Nogawa, R. T., et al., *Cell Immunol* (1980) 53:116
74. Stanley, E. R., *Methods Enzymol* (1985) 116:564
75. Gluzman, Y. *Cell* 23:175 (1981)
76. Ringold, G. I. *Mol. App. Genet.* (1982) 1:165
77. Berger, S. L., et al., *Biochemistry* (1979) 18:5143
78. Aviv, J., et al., *Proc Natl Acad Sci* (1972) 69:1408–1412
79. Moore, R. N., et al., *J Immunol* (1983) 131:2374
80. Prystowsky, M. B., et al. *Am J Pathol* (1984) 114:149
81. Huynh, T. V., et al., in *DNA Cloning Techniques: A Practical Approach* IRL Press, Oxford 1984, D. Glover, ed.

82. Okayama, H., et al, *Mol Cell Biol* (1983) 3:280–289
83. Wang, A. M., et al., *Science* (1985) 228:149
84. Okayama, H., et al., *Mol Cel Biol* (1983) 3:280–289
85. Stanley, E. R., et al., *J Lab Clin Med* (1972) 79:657
86. Gorman, C., et al., *Science* (1983) 221:551–553
87. Maxam, A., et al., *Methods in Enzymology* (1980) 68:521, Academic Press

---

We claim:

1. A CSF-1 polypeptide consisting of amino acids 4 to 224 of the sequence shown in or a carboxy truncated polypeptide thereof, wherein the carboxy truncated polypeptide contains at least amino acids 4–150 of SEQ ID NO: 2.

2. A CSF-1 polypeptide in accordance with claim 1, wherein amino acids at positions selected from the group consisting of 15–20, 51, 52, 75–84, and 489–491 are deleted or substituted with another amino acid.

3. A CSF-1 polypeptide in accordance with claim 1, wherein at least one of the amino acids at positions 52, 59, 150, and 159 is substituted and is Gln, Asp/Tyr, Gly, and Asp, respectively.

4. A CSF-1 polypeptide in accordance with claim 2, said polypeptide being a member selected from the group consisting of an N∇3 polypeptide of C∇150 CSF-1, C∇158 CSF-1, and C∇159 CSF-1, with the proviso that amino acid residues at positions 52, 59, 150, 158, and 159 are deleted or substituted with another amino acid.

5. A CSF-1 polypeptide in accordance with claim 1, wherein the glycosylation sites have been deleted or substituted with another amino acid.

6. A CSF-1 polypeptide composition in accordance with claim 1, further comprising one or more pharmaceutically acceptable formulants.

7. A CSF-1 polypeptide composition in accordance with claim 2, further comprising one or more pharmaceutically acceptable formulants.

8. A CSF-1 polypeptide composition in accordance with claim 3, further comprising one or more pharmaceutically acceptable formulants.

9. A CSF-1 polypeptide composition in accordance with claim 4, further comprising one or more pharmaceutically acceptable formulants.

10. A CSF-1 polypeptide composition in accordance with claim 1, further comprising one or more antitumor agents or lymphokines.

11. A CSF-1 polypeptide composition in accordance with claim 2, further comprising one or more antitumor agents or lymphokines.

12. A CSF-1 polypeptide composition in accordance with claim 3, further comprising one or more antitumor agents or lymphokines.

13. A CSF-1 polypeptide composition in accordance with claim 4, further comprising one or more antitumor agents or lymphokines.

14. A CSF-1 polypeptide in accordance with claim 4, wherein at least one of the amino acids at positions 52, 59, 150, 158 or 159 is substituted with Gln/Pro, Asp/Tyr, Gly, Pro, or Pro respectively.

* * * * *

UNITED STATES PATENT AND TRADEMARK OFFICE
CERTIFICATE OF CORRECTION

PATENT NO. : 5,643,563
DATED : July 1, 1997
INVENTOR(S) : Martha B. Ladner, *et al.*

It is certified that error appears in the above-indentified patent and that said Letters Patent is hereby corrected as shown below:

At column 4, line 56, please delete "intedeukin" and replace therefore --interleukin--.

At column 38, line 40, please delete "tires" and replace therefore --urea--.

At column 39, line 33, please delete "0.4°C" and replace therefore --4°C--.

At column 79, line 22, after "sequence shown in", insert --SEQ ID NO:2--.

Signed and Sealed this

Sixteenth Day of December, 1997

Attest:

BRUCE LEHMAN

Attesting Officer

Commissioner of Patents and Trademarks